US009659145B2

(12) United States Patent
Sayood et al.

(10) Patent No.: US 9,659,145 B2
(45) Date of Patent: May 23, 2017

(54) CLASSIFICATION OF NUCLEOTIDE SEQUENCES BY LATENT SEMANTIC ANALYSIS

(71) Applicants: Khalid Sayood, Lincoln, NE (US); Sam Way, Boulder, CO (US); Ozkan Ufuk Nalbantoglu, Lincoln, NE (US); George Garrity, Okemos, MI (US)

(72) Inventors: Khalid Sayood, Lincoln, NE (US); Sam Way, Boulder, CO (US); Ozkan Ufuk Nalbantoglu, Lincoln, NE (US); George Garrity, Okemos, MI (US)

(73) Assignees: NUtech Ventures, Lincoln, NE (US); NamesforLife, LLC, Lansing, MI (US)

( * ) Notice: Subject to any disclaimer, the term of this patent is extended or adjusted under 35 U.S.C. 154(b) by 0 days.

(21) Appl. No.: 13/954,925

(22) Filed: Jul. 30, 2013

(65) Prior Publication Data
US 2014/0121985 A1    May 1, 2014

Related U.S. Application Data

(60) Provisional application No. 61/677,316, filed on Jul. 30, 2012.

(51) Int. Cl.
*G01N 33/48* (2006.01)
*G06F 19/22* (2011.01)
*G06F 19/24* (2011.01)

(52) U.S. Cl.
CPC .............. *G06F 19/22* (2013.01); *G06F 19/24* (2013.01)

(58) Field of Classification Search
CPC ..................................................... G06F 19/24
USPC ........................................................ 702/20
See application file for complete search history.

(56) References Cited

U.S. PATENT DOCUMENTS

| 5,878,373 | A | 3/1999 | Cohen et al. |
| 2005/0164217 | A1 | 7/2005 | Yoshii |
| 2006/0112042 | A1 | 5/2006 | Platt et al. |
| 2009/0006002 | A1 | 1/2009 | Honisch et al. |
| 2009/0204333 | A1 | 8/2009 | Friend et al. |

OTHER PUBLICATIONS

International Search Report and Written Opinion in International Application No. PCT/US2013/052797, mailed Nov. 19, 2013, 18 pages.
"BAuA TRBA-466," Technical Rules for Biological Agents, Dec. 2010, 254 pages.
Bauer et al., "The Average Mutual Information Profile as a Genomic Signature," *BMC Bioinformatics*, 2008, 9:48, 11 pages.
Brady and Salzberg, "Phymm and Phymmbl: Metagenomic Phylogenetic Classification with Interpolated Markov Models," *Nature Methods*, 2009, 6:673-676.
Chung, et al., "Gut Immune Maturation Depends on Colonization with a Host-Specific Microbiota," *Cell*, 2012, 149(7):1578-1593.
Cole et al., "The Ribosomal Database Project: Improved Alignments and New Tools for RNA Analysis," *Nucleic Acids Research*, 2009, 37:D141-D145.
Collins et al., "The Human Genome Project: Lessons from Large-Scale Biology," *Science*, 2003, 300(5617):286-290.
Ding et al., "Convex and Semi-normegative Matrix Factorizations," *IEEE Trans. Pattern Anal. Mach Intell.*, Jan. 2010, 32(1):45-55.
Dumais et al., "Using Latent Semantic Analysis to Improve Access to Textual Information," *Proceeding of the SIGCHI Conference on Human Factors in Computing Systems*, 1988, 281-285.
Dumais, "Latent Semantic Analysis," *Annual Review of Information Science and Technology*, 2004, 38(1):188-230.
Felsenstein, "Evolutionary Trees from DNA Sequences: A Maximum Likelihood Approach," *J. Molecular Evolution*, 1981, 17:368-376.
Fox et al., "How Close is Close: 16s rRNA Sequence Identity May Not Be Sufficient to Guarantee Species Identity," *International J. of Systematic Bacteriology*, 1992, 42(1)166-170.
Furnas et al., "The Vocabulary Problem in Human-System Communication," *Comm. ACM*, 1987, 30(11):964-971.
Hasegawa et al., "Dating of the Human-Ape Splitting by a Molecular Clock of Mitochondrial DNA," *J. Molecular Evolution*, 1985, 22:160-174.
Holloway, "Pseudomonas," *Genetics and Taxonomy*, 1996, 22-32.
Huson et al., "Megan Analysis of Metagenomic Data," *Genome Research*, 2007, 17(3):377-386.
Jolliffe, "A Note on the Use of Principal Components in Regression," *Applied Statistics*, 1982, 31(3):300-303.
Jolliffe, *Principal Component Analysis*, Springer, 1986.
Jukes and Cantor, "Evolution of Protein Molecules," *Mammalian Protein Metabolism*, 1969, 21-132.
Katoh and Toh, "Parallelization of the MAFFT Multiple Sequence Alignment Program," *Bioinformatics*, 2010, 26(15):1899-1900.
Kim and Park, "Fast Non-negative Matrix Factorization: An Active-Set-Like Method and Comparisons," *SIAM J. Scientific Computing*, 2011, 33(6):3261-3281.
Kimura, "A Simple Method for Estimating Evolutionary Rates of Base Substitutions Through Comparative Studies of Nucleotide Sequences," *J. Molecular Evolution*, 1980, 16(2):111-120.
Krause et al., "Phylogenetic Classification of Short Environmental DNA Fragments," *Nucleic Acids Research*, 2008, 36(7):2230-2239.
Landauer et al., "An Introduction to Latent Semantic Analysis," *Discourse Processes*, 1998, 25(2-3):259-284.

(Continued)

*Primary Examiner* — Jerry Lin
(74) *Attorney, Agent, or Firm* — Fish & Richardson P.C.

(57) ABSTRACT

DNA sequences are analyzed using latent semantic analysis. A set of nucleotide sequences is received in which the set has a first number of sequences. A set of basis vectors is determined, in which the set has a second number of basis vectors, the second number being smaller than the first number. Each basis vector represents a specific combination of predetermined nucleotide segments. For each of the nucleotide sequences, an approximate representation of the nucleotide sequence is determined based on a combination of the basis vectors. For each pair of nucleotide sequences, a distance between the pair of nucleotide sequences is determined according the distance between the approximate representation of the pair of nucleotide sequences. The set of nucleotide sequences are classified based on the distances between the pairs of nucleotide sequences.

61 Claims, 24 Drawing Sheets

(56) References Cited

OTHER PUBLICATIONS

Lane et al., "Rapid Determination of 16S Ribosomal RNA Sequences for Phylogenetic Analyses," *Proceedings of the National Academy of Sciences*, 1985, 82(20):6955-6959.
Lee and Seung, "Learning the Parts of Objects by Non-negative Matrix Factorization," *Nature*, 1999, 401(6755):788-791.
Lee and Seung, "Unsupervised Learning by Convex and Conic Coding," *Advances in Neural Information Processing Systems 9*, 1997, 515-521.
Lempel and Ziv, "On the Complexity of Finite Sequences," *IEEE Transactions on Information Theory*, Jan. 1976, 22(1):75-81.
Li and Ngom, "Non-negative Matrix and Tensor Factorization Based Classification of Clinical Microarray Gene Expression Data," *IEEE International Conference on Bioinformatics and Biomedicine*, 2010, 438-443.
Li and Vitanyi, An Introduction to Kolmogorov Complexity and its Applications, Springer, 1997, 641-650.
Li et al., "De Novo Assembly of Human Genomes with Massively Parallel Short Read Sequencing," *Genome Research*, 2009.
Li, "Visualization of High Dimensional Data with Relational Perspective Map," *Information Visualization*, 2004, 3(1):49-59.
Lin, "Projected Gradient Methods for Non-negative Matrix Factorization," *Neural Computation*, 2007, 19:2756-2779.
Logothetis and Sheinberg, "Visual Object Recognition," *Annu. Rev. Neurosci.*, 1996, 94:4577-4621.
Mattoon and Schweitzer, "Profiling Protein Interaction Networks with Functional Protein Microarrays," *Protein Networks and Pathway Analysis, Methods in Molecular Biology*, 2009, 563:63-74.
Nalbantoglu et al., "RAIphy: Phylogenetic Classification of Metagenomics Samples Using Iterative Refinement of Relative Abundance Index Profiles," *BMC Bioinformatics*, 2011, 12:41.
Needleman and Wunsch, "A General Method Applicable to the Search for Similarities in the Amino Acid Sequence of Two Proteins," *J. Molecular Biology*, 1970, 48(3):443-453.
Otu and Sayood, "A New Sequence Distance Measure for Phylogenetic Tree Construction," *Bioinformatics*, 2003, 19(16):2122-2130.
Palmer, "Hierarchical Structure in Perceptual Representation," *Cognitive Psychology*, 1977, 9(4):441-474.
Payne et al., "Development of a recA Gene-Based Identification Approach for the Entire *Burkholderia* Genus," *Applied and Environmental Mirobiology*, 2005, 71(7):3917-3927.
PHYLIP (phylogeny inference package) Version 3.5c, Older versions of PHYLIP, Mar. 1993, retrieved Jan. 22, 2014, http://evolution.genetics.washington.edu/phylip/oldversions.html, 3 pages.
Russell et al., "Grammar-based Distance in Progressive Multiple Sequence Alignment," *BMC Bioinformatics*, 2008, 9.1:306.
Salton and Buckley, "Term-weighting Approaches in Automatic Text Retrieval," *Information Processing & Management*, 1988, 24(5):5133-523.
Schmidt, "Data Explosion: Bringing Order to Chaos with Bioinformatics," *Environ Health Perspect*, May 2003, 111(6):1-4.
Shendure and Ji, "Next-generation DNA Sequencing," *Nature Biotechnology*, 2008, 26(10):1135-1145.
Smith and Waterman, "Identification of Common Molecular Subsequences," *J. Molecular Biology*, 1981, 147(1):195-197.
Somorjai et al., "Mapping High-Dimensional Data onto a Relative Distance Plane—An Exact Method for Visualizing and Characterizing High-dimensional Patterns," *J. Biomedical Informatics*, 2004, 37(5):366-379.
Stoughton, "Application of DNA Microarrays in Biology," *Annual Review of Biochemistry*, 2005, 74(1)53-82.
Tamura and Nei, "Estimation of the Number of Nucleotide Substitutions in the Control Region of Mitochondrial DNA in Humans and Chimpanzees," *Molecular Biology and Evolution*, 1993, 10(3):512-526.
Tamura, "Estimation of the Number of Nucleotide Substitutions When There Are Strong Transition-Transversion and G+C-content biases," *Molecular Biology and Evolution*, 1992, 9(4):678-687.
Tavare, "Some Probabilistic and Statistical Problems in the Analysis of DNA Sequences," Amer. Mathematical Society, 1986, 17:57-86.
Turk and Pentland, "Eigenfaces for Recognition," *J. Cognitive Neuroscience*, 1991, 3(1):71-86.
Tzafestas et al., "Performance Evaluation and Dynamic Node Generation Criteria for 'Principal Component Analysis' Neural Networks," *Mathematics and Computers in Simulation*, 2000, 51(34):145-156.
Van der Maaten et al., "Dimensionality Reduction: A Comparative Review," Jan. 11, 2008, 22 pages.
Venna, "Dimensionality Reduction for Visual Exploration of Similarity Structures," *PhD Thesis*, Helsinki University of Technology, 2007, 81 pages.
Wachsmuth et al., "Recognition of Objects and their Component Parts: Responses of Single Units in the Temporal Cortex of the Macaque," *Cerebral Cortex*, 1994, 4(5):509-522.
Wetterstrand, "DNA Sequencing Costs: Data from the NHGRI Large-Scale Genome Sequencing Program," National Human Genome Research Institute, posted on or before Feb. 20, 2011, retrieved Jan. 17, 2014, http://genome.gov/sequencingcosts/, 3 pages.
Widmer et al., "A Highly Selective PCR Protocol for Detecting 16S rRNA Genes of the Genus *Pseudomonas* (Sensu Stricto) in Environmental Samples," *Applied Environmental Microbiology*, 1998, 64(7):2545-2553.
Woese, "Bacterial Evolution," *Microbiological Reviews*, 1987, 51(2):221-271.
Xu et al., "Document Clustering Based on Non-Negative Matrix Factorization," *Proceedings of the 26th Annual International ACM SIGIR Conference on Research and Development in Information Retrieval*, 2003, 267-273.

CLASSIFICATION OF NUCLEOTIDE SEQUENCES BY LATENT SEMANTIC ANALYSIS

CROSS-REFERENCE TO RELATED APPLICATIONS

This application is claims priority to U.S. provisional application 61/677,316, filed on Jul. 30, 2012, which is incorporated herein by reference in its entirety.

STATEMENT AS TO FEDERALLY SPONSORED RESEARCH

This invention was made with government support under grants NIH AI068151 and DOE DE-FG02-07ER86321. The government has certain rights in the invention.

TECHNICAL FIELD

This subject matter is generally related to analyses of sequences, such as nucleotide sequences and protein sequences.

BACKGROUND

Evolutionary distance measures provide a way of identifying and organizing related organisms by comparing their genomic sequences. Techniques that quantify the level of similarity between deoxyribonucleic acid (DNA) sequences are useful in our efforts to decipher the genetic code in which they are written. In some examples, the evolutionary distance separating two genomic sequences can be estimated by first aligning the sequences then comparing the aligned sequences. This preliminary aligning step may impose a large computational burden.

In some examples, massively parallel DNA sequencing uses automated, high-throughput technologies that produce a large amount of sequence data. It is useful to have efficient techniques for classifying and organizing genomic sequences such that they may be quickly identified and retrieved.

SUMMARY

In general, in one aspect, a method for analyzing nucleotide sequences is provided. The method includes receiving a first set of nucleotide sequences, the first set having a first number of nucleotide sequences; determining, by a data processor, a set of basis vectors, the set having a second number of basis vectors, in which the second number is smaller than the first number, and each basis vector represents a specific combination of predetermined nucleotide segments; for each of the first set of nucleotide sequences, determining an approximate representation of the nucleotide sequence based on a combination of the basis vectors; for each pair of a plurality of pairs of nucleotide sequences, determining distances between the pair of nucleotide sequences according distances between the approximate representations of the pair of nucleotide sequences; and classifying the first set of nucleotide sequences based on the distances between the pairs of nucleotide sequences.

Implementations of the method may include one or more of the following features. A first portion of the first set of nucleotide sequences belong to known species of at least one of prokaryotes, eukaryotes, or viruses, a second portion of the first set of nucleotide sequences are obtained from a patient, and the method comprises, for each nucleotide sequence in the second portion, determining whether the nucleotide sequence is associated with one of the known species of the at least one of prokaryotes, eukaryotes, or viruses based on the classification of the first set of nucleotide sequences.

The predetermined nucleotide segments are k-mers each having k nucleobases, k being a positive integer, and each basis vector represents a specific combination of the k-mers.

Determining a set of basis vectors comprises forming a k-mer-sequence matrix in which rows of the matrix represent the k-mers and columns of the matrix represent the nucleotide sequences, k being a positive integer, and each element in the matrix represents a repetition frequency of the segment represented by the corresponding row within the sequence represented by the corresponding column, and applying a dimension reduction process to the k-mer-sequence matrix to determine the basis vectors.

Applying a dimension reduction process comprises applying at least one of non-negative matrix factorization or singular value decomposition to the segment-sequence matrix to determine the basis vectors.

Determining a set of basis vectors comprises forming a segment-sequence matrix in which rows of the matrix represent the nucleotide segments and columns of the matrix represent the sequences, each element in the matrix representing a repetition frequency of the segment represented by the corresponding row within the sequence represented by the corresponding column, and applying a dimension reduction process to the segment-sequence matrix to determine the basis vectors.

Applying a dimension reduction process comprises applying at least one of non-negative matrix factorization or singular value decomposition to the segment-sequence matrix to determine the basis vectors.

Determining an approximate representation of the nucleotide sequence based on a combination of the basis vectors comprises determining an approximate representation of the nucleotide sequence based on a linear combination of the basis vectors.

Determining an approximate representation of the nucleotide sequence comprises determining coefficients for a linear combination of the basis vectors that represents an approximation of the nucleotide sequence.

The distance between the approximate representations of the pair of nucleotide sequences is determined according at least one of (i) Euclidean distance between the approximate representations of the pair of nucleotide sequences or (ii) correlation between the approximate representations of the pair of nucleotide sequences.

The method comprises determining the distance between every pair of nucleotide sequences, and classifying the first set of nucleotide sequences based on the distances between all of the pairs of nucleotide sequences.

A first portion of the first set of nucleotide sequences belong to known species, species of a second portion of the first set of nucleotide sequences initially being unknown, and the method comprises for each nucleotide sequence in the second portion, determining whether the nucleotide sequence belongs to one of the known species based on the classification of the first set of nucleotide sequences.

In general, in another aspect, a method for analyzing nucleotide sequences is provided. The method includes receiving a first set of nucleotide sequences, the first set having a first number of nucleotide sequences; forming a segment-sequence matrix in which rows of the matrix represent the nucleotide segments and columns of the matrix represent the sequences, each element in the matrix representing a repetition frequency of the segment represented by the corresponding row within the sequence represented by the corresponding column; determining, by a data processor, a set of basis vectors that can be used to approximately represent the first set of nucleotide sequences, the set having a second number of basis vectors, in which the second number is smaller than the first number, and each basis vector represents a specific combination of predetermined nucleotide segments, in which the determining a set of basis vectors comprises applying at least one of non-negative matrix factorization or singular value decomposition to the segment-sequence matrix to determine the basis vectors.

Implementations of the method may include one or more of the following features. The method comprises determining a projection matrix based on the basis vectors, and projecting segment-sequence vectors into a feature space based on the projection matrix.

The method comprises receiving a second set of nucleotide sequences that includes nucleotide sequences from a host and nucleotide sequences from a plurality of species different from the host; projecting the second set of nucleotide sequences into the feature space; clustering the projected sequences in the feature space; and identifying one or more clusters that are primarily associated with the host.

The method comprises receiving a second set of nucleotide sequences that includes nucleotide sequences from a host and nucleotide sequences from a plurality of known species different from the host; receiving a third set of nucleotide sequences that includes nucleotide sequences from either the host or other species without information on which nucleotide sequences in the third set belong to the host; projecting the second and third sets of nucleotide sequences into the feature space; clustering the projected sequences in the feature space; identifying one or more clusters that are primarily associated with the host; and removing sequences from the third set that are in the one or more clusters primarily associated with the host.

The plurality of known species comprises known species of at least one of prokaryotes, eukaryotes, or viruses, and the third set of nucleotide sequences are obtained from the host.

The method comprises, for each of the first set of nucleotide sequences, determining an approximate representation of the nucleotide sequence based on a combination of the basis vectors; for each pair of a plurality of pairs of nucleotide sequences, determining distances between the pair of nucleotide sequences according distances between the approximate representations of the pair of nucleotide sequences; and classifying the first set of nucleotide sequences based on the distances between the pairs of nucleotide sequences.

The distance between the approximate representations of the pair of nucleotide sequences is determined according at least one of (i) Euclidean distance between the approximate representations of the pair of nucleotide sequences or (ii) correlation between the approximate representations of the pair of nucleotide sequences.

The method comprises determining the distance between every pair of nucleotide sequences, and classifying the first set of nucleotide sequences based on the distances between all of the pairs of nucleotide sequences.

A first portion of the first set of nucleotide sequences belong to known species of at least one of prokaryotes, eukaryotes, or viruses, a second portion of the first set of nucleotide sequences are obtained from a patient, and the method comprises, for each nucleotide sequence in the second portion, determining whether the nucleotide sequence is associated with one of the known species of the at least one of prokaryotes, eukaryotes, or viruses based on the classification of the first set of nucleotide sequences.

Determining an approximate representation of the nucleotide sequence based on a combination of the basis vectors comprises determining an approximate representation of the nucleotide sequence based on a linear combination of the basis vectors.

Determining an approximate representation of the nucleotide sequence comprises determining coefficients for a linear combination of the basis vectors that represents an approximation of the nucleotide sequence.

A first portion of the first set of nucleotide sequences belong to known species, species of a second portion of the first set of nucleotide sequences initially being unknown, and the method comprises for each nucleotide sequence in the second portion, determining whether the nucleotide sequence belongs to one of the known species based on the classification of the first set of nucleotide sequences.

The predetermined nucleotide segments are k-mers each having k nucleobases, k being a positive integer, and each basis vector represents a specific combination of the k-mers.

In general, in another aspect, a method for analyzing nucleotide sequences is provided. The method comprises receiving a first set of nucleotide sequences that includes nucleotide sequences from a host and nucleotide sequences from a plurality of known species different from the host; receiving a second set of nucleotide sequences that includes nucleotide sequences from either the host or other species without information on which nucleotide sequences in the second set belong to the host; generating a segment-sequence vector for each of the nucleotide sequences in the first and second sets of nucleotide sequences, the segment-sequence vector providing information on nucleotide segments included in the nucleotide sequence; projecting, by a data processor, the segment-sequence vectors for the first and second sets of nucleotide sequences into a feature space; clustering the nucleotide sequences in the feature space; identifying one or more clusters that are primarily associated with the nucleotide sequences from the host; and removing nucleotide sequences from the second set of nucleotide sequences that are in the one or more clusters primarily associated with the nucleotide sequences from the host.

Implementations of the method may include one or more of the following features. The method comprises forming a segment-sequence matrix in which rows of the matrix represent the nucleotide segments and columns of the matrix represent known nucleotide sequences from a third set of nucleotide sequences, in which each element in the matrix represents a repetition frequency of the segment represented by the corresponding row within the sequence represented by the corresponding column, and the third set of nucleotide sequences includes nucleotide sequences from the host and nucleotide sequences from one or more of the plurality of known species different from the host; and determining a set of basis vectors that can be used to approximately represent the third set of nucleotide sequences, each basis vector representing a specific combination of predetermined nucleotide segments; wherein projecting the segment-sequence vectors for the first and second sets of nucleotide sequences into a feature space comprises applying a projection matrix to the segment-sequence vectors to project the segment-sequence vectors into the feature space, the projection matrix being determined based on the basis vectors.

The third set of nucleotide sequences is different from the first set of nucleotide sequences.

The nucleotide sequences remaining in the second set of nucleotide sequences form a third set of nucleotide sequences, and the method comprises projecting the segment-sequence vectors for the first and third set of nucleotide sequences into the feature space; clustering the nucleotide sequences in the feature space; identifying one or more clusters that are primarily associated with the nucleotide sequences from the host; and removing nucleotide sequences from the third set of nucleotide sequences that are in the one or more clusters primarily associated with the nucleotide sequences from the host.

In general, in another aspect, a method for analyzing nucleotide sequences is provided. The method comprises receiving a set of nucleotide sequences, the set having a first number of nucleotide sequences; determining, by a data processor, a set of basis vectors, the set having a second number of basis vectors, in which the second number is smaller than the first number, and each basis vector represents a specific combination of predetermined nucleotide segments; and for each of the basis vectors, determining a segment that is more strongly associated with the basis vector than the other segments.

Implementations of the method may include one or more of the following features. The method comprises providing a microarray having probes that are selected based on the nucleotide segments that are more strongly associated with the basis vectors.

The set of nucleotide sequences belong to known species of at least one of prokaryotes, eukaryotes, or viruses.

The predetermined nucleotide segments are k-mers each having k nucleobases, k being a positive integer, and each basis vector represents a specific combination of the k-mers.

Determining a set of basis vectors comprises forming a k-mer-sequence matrix in which rows of the matrix represent the k-mers and columns of the matrix represent the nucleotide sequences, and each element in the matrix represents a repetition frequency of the segment represented by the corresponding row within the sequence represented by the corresponding column, and applying at least one of non-negative matrix factorization or singular value decomposition to the k-mer-sequence matrix to determine the basis vectors.

Determining a set of basis vectors comprises forming a segment-sequence matrix in which rows of the matrix represent the nucleotide segments and columns of the matrix represent the sequences, each element in the matrix representing a repetition frequency of the segment represented by the corresponding row within the sequence represented by the corresponding column, and applying at least one of non-negative matrix factorization or singular value decomposition to the segment-sequence matrix to determine the basis vectors.

Determining an approximate representation of the nucleotide sequence based on a combination of the basis vectors comprises determining an approximate representation of the nucleotide sequence based on a linear combination of the basis vectors.

In general, in another aspect, a method for analyzing protein sequences is provided. The method comprises receiving a first set of protein sequences, the first set having a first number of protein sequences; determining, by a data processor, a set of basis vectors, the set having a second number of basis vectors, in which the second number is smaller than the first number, and each basis vector represents a specific combination of predetermined protein segments; for each of the first set of protein sequences, determining an approximate representation of the protein sequence based on a combination of the basis vectors; for each pair of a plurality of pairs of protein sequences, determining distances between the pair of protein sequences according distances between the approximate representations of the pair of protein sequences; and classifying the first set of protein sequences based on the distances between the pairs of nucleotide sequences.

Implementations of the method may include one or more of the following features. A first portion of the first set of protein sequences belong to known species of at least one of prokaryotes, eukaryotes, or viruses, a second portion of the first set of protein sequences are obtained from a patient, and the method comprises, for each protein sequence in the second portion, determining whether the protein sequence is associated with one of the known species of the at least one of prokaryotes, eukaryotes, or viruses based on the classification of the first set of protein sequences.

The predetermined protein segments are k-mers each having k amino acids, k being a positive integer, and each basis vector represents a specific combination of the k-mers.

Determining a set of basis vectors comprises forming a k-mer-sequence matrix in which rows of the matrix represent the k-mers and columns of the matrix represent the protein sequences, and each element in the matrix represents a repetition frequency of the segment represented by the corresponding row within the sequence represented by the corresponding column, and applying a dimension reduction process to the k-mer-sequence matrix to determine the basis vectors.

Applying a dimension reduction process comprises applying at least one of non-negative matrix factorization or singular value decomposition to the segment-sequence matrix to determine the basis vectors.

Determining a set of basis vectors comprises forming a segment-sequence matrix in which rows of the matrix represent the protein segments and columns of the matrix represent the sequences, each element in the matrix representing a repetition frequency of the segment represented by the corresponding row within the sequence represented by the corresponding column, and applying a dimension reduction process to the segment-sequence matrix to determine the basis vectors.

Applying a dimension reduction process comprises applying at least one of non-negative matrix factorization or singular value decomposition to the segment-sequence matrix to determine the basis vectors.

Determining an approximate representation of the protein sequence based on a combination of the basis vectors comprises determining an approximate representation of the protein sequence based on a linear combination of the basis vectors.

Determining an approximate representation of the protein sequence comprises determining coefficients for a linear combination of the basis vectors that represents an approximation of the protein sequence.

The distance between the approximate representations of the pair of protein sequences is determined according at least one of (i) Euclidean distance between the approximate representations of the pair of protein sequences or (ii) correlation between the approximate representations of the pair of protein sequences.

The method comprises determining the distance between every pair of protein sequences, and classifying the first set of protein sequences based on the distances between all of the pairs of protein sequences.

A first portion of the first set of protein sequences belong to known species, species of a second portion of the first set of protein sequences initially being unknown, and the method comprises for each protein sequence in the second portion, determining whether the protein sequence belongs to one of the known species based on the classification of the first set of protein sequences.

In general, in another aspect, a method for analyzing protein sequences is provided. The method comprises receiving a first set of protein sequences, the first set having a first number of protein sequences; forming a segment-sequence matrix in which rows of the matrix represent the protein segments and columns of the matrix represent the sequences, each element in the matrix representing a repetition frequency of the segment represented by the corresponding row within the sequence represented by the corresponding column; determining, by a data processor, a set of basis vectors that can be used to approximately represent the first set of protein sequences, the set having a second number of basis vectors, in which the second number is smaller than the first number, and each basis vector represents a specific combination of predetermined protein segments, in which the determining a set of basis vectors comprises applying at least one of non-negative matrix factorization or singular value decomposition to the segment-sequence matrix to determine the basis vectors.

Implementations of the method may include one or more of the following features. The method comprises determining a projection matrix based on the basis vectors, and projecting segment-sequence vectors into a feature space based on the projection matrix.

The method comprises receiving a second set of protein sequences that includes protein sequences from a host and protein sequences from a plurality of species different from the host; projecting the second set of protein sequences into the feature space; clustering the projected sequences in the feature space; and identifying one or more clusters that are primarily associated with the host.

The method comprises receiving a second set of protein sequences that includes protein sequences from a host and protein sequences from a plurality of known species different from the host; receiving a third set of protein sequences that includes protein sequences from either the host or other species without information on which protein sequences in the third set belong to the host; projecting the second and third sets of protein sequences into the feature space; clustering the projected sequences in the feature space; identifying one or more clusters that are primarily associated with the host; and removing sequences from the third set that are in the one or more clusters primarily associated with the host.

The plurality of known species comprises known species of at least one of prokaryotes, eukaryotes, or viruses, and the third set of protein sequences are obtained from the host.

The method comprises, for each of the first set of protein sequences, determining an approximate representation of the protein sequence based on a combination of the basis vectors; for each pair of a plurality of pairs of protein sequences, determining distances between the pair of protein sequences according distances between the approximate representations of the pair of protein sequences; and classifying the first set of protein sequences based on the distances between the pairs of protein sequences.

The distance between the approximate representations of the pair of protein sequences is determined according at least one of (i) Euclidean distance between the approximate representations of the pair of protein sequences or (ii) correlation between the approximate representations of the pair of protein sequences.

The method comprises determining the distance between every pair of protein sequences, and classifying the first set of protein sequences based on the distances between all of the pairs of protein sequences.

A first portion of the first set of protein sequences belong to known species of at least one of prokaryotes, eukaryotes, or viruses, a second portion of the first set of protein sequences are obtained from a patient, and the method comprises, for each protein sequence in the second portion, determining whether the protein sequence is associated with one of the known species of the at least one of prokaryotes, eukaryotes, or viruses based on the classification of the first set of protein sequences.

Determining an approximate representation of the protein sequence based on a combination of the basis vectors comprises determining an approximate representation of the protein sequence based on a linear combination of the basis vectors.

Determining an approximate representation of the protein sequence comprises determining coefficients for a linear combination of the basis vectors that represents an approximation of the protein sequence.

A first portion of the first set of protein sequences belong to known species, species of a second portion of the first set of protein sequences initially being unknown, and the method comprises for each protein sequence in the second portion, determining whether the protein sequence belongs to one of the known species based on the classification of the first set of protein sequences.

The predetermined protein segments are k-mers each having k amino acids, k being a positive integer, and each basis vector represents a specific combination of the k-mers.

In general, in another aspect, a method for analyzing protein sequences is provided. The method comprises receiving a first set of protein sequences that includes protein sequences from a host and protein sequences from a plurality of known species different from the host; receiving a second set of protein sequences that includes protein sequences from either the host or other species without information on which protein sequences in the second set belong to the host; generating a segment-sequence vector for each of the protein sequences in the first and second sets of protein sequences, the segment-sequence vector providing information on protein segments included in the protein sequence; projecting, by a data processor, the segment-sequence vectors for the first and second sets of protein sequences into a feature space; clustering the protein sequences in the feature space; identifying one or more clusters that are primarily associated with the protein sequences from the host; and removing protein sequences from the second set of protein sequences that are in the one or more clusters primarily associated with the protein sequences from the host.

Implementations of the method may include one or more of the following features. The method comprises forming a segment-sequence matrix in which rows of the matrix represent the protein segments and columns of the matrix represent known protein sequences from a third set of protein sequences, in which each element in the matrix represents a repetition frequency of the segment represented by the corresponding row within the sequence represented by the corresponding column, and the third set of protein sequences includes protein sequences from the host and protein sequences from one or more of the plurality of known species different from the host; and determining a set of basis vectors that can be used to approximately represent the third set of protein sequences, each basis vector representing a specific combination of predetermined protein segments; wherein projecting the segment-sequence vectors for the first and second sets of protein sequences into a feature space comprises applying a projection matrix to the segment-sequence vectors to project the segment-sequence vectors into the feature space, the projection matrix being determined based on the basis vectors.

The third set of protein sequences is different from the first set of protein sequences.

The protein sequences remaining in the second set of protein sequences form a third set of protein sequences, and the method comprises projecting the segment-sequence vectors for the first and third set of protein sequences into the feature space; clustering the protein sequences in the feature space; identifying one or more clusters that are primarily associated with the protein sequences from the host; and removing protein sequences from the third set of protein sequences that are in the one or more clusters primarily associated with the protein sequences from the host.

In general, in another aspect, an apparatus for analyzing nucleotide sequences comprises a memory to store data representing a first set of nucleotide sequences, the first set having a first number of nucleotide sequences; and a data processor configured to process the data and determine a set of basis vectors, the set having a second number of basis vectors, in which the second number is smaller than the first number, and each basis vector represents a specific combination of predetermined nucleotide segments; for each of the first set of nucleotide sequences, determine an approximate representation of the nucleotide sequence based on a combination of the basis vectors; for each pair of a plurality of pairs of nucleotide sequences, determine a distance between the pair of nucleotide sequences according a distance between the approximate representations of the pair of nucleotide sequences; and classify the first set of nucleotide sequences based on the distances between the pairs of nucleotide sequences.

Implementations of the apparatus may include one or more of the following features. A first portion of the first set of nucleotide sequences belong to known species of at least one of prokaryotes, eukaryotes, or viruses, a second portion of the first set of nucleotide sequences are obtained from a patient, and the data processor is further configured to, for each nucleotide sequence in the second portion, determine whether the nucleotide sequence is associated with one of the known species of the at least one of prokaryotes, eukaryotes, or viruses based on the classification of the first set of nucleotide sequences.

The predetermined nucleotide segments are k-mers each having k nucleobases, k being a positive integer, and each basis vector represents a specific combination of the k-mers.

Determine a set of basis vectors comprises form a k-mer-sequence matrix in which rows of the matrix represent the k-mers and columns of the matrix represent the nucleotide sequences, k being a positive integer, and each element in the matrix represents a repetition frequency of the segment represented by the corresponding row within the sequence represented by the corresponding column, and apply at least one of non-negative matrix factorization or singular value decomposition to the k-mer-sequence matrix to determine the basis vectors.

Determine a set of basis vectors comprises form a segment-sequence matrix in which rows of the matrix represent the nucleotide segments and columns of the matrix represent the sequences, each element in the matrix representing a repetition frequency of the segment represented by the corresponding row within the sequence represented by the corresponding column, and apply at least one of non-negative matrix factorization or singular value decomposition to the segment-sequence matrix to determine the basis vectors.

Determine an approximate representation of the nucleotide sequence based on a combination of the basis vectors comprises determine an approximate representation of the nucleotide sequence based on a linear combination of the basis vectors.

Determine an approximate representation of the nucleotide sequence comprises determine coefficients for a linear combination of the basis vectors that represents an approximation of the nucleotide sequence.

The distance between the approximate representations of the pair of nucleotide sequences is determined according at least one of (i) Euclidean distance between the approximate representations of the pair of nucleotide sequences or (ii) correlation between the approximate representations of the pair of nucleotide sequences.

The data processor is further configured to determine the distance between every pair of nucleotide sequences, and classify the first set of nucleotide sequences based on the distances between all of the pairs of nucleotide sequences.

A first portion of the first set of nucleotide sequences belong to known species, species of a second portion of the first set of nucleotide sequences initially being unknown, and the data processor is further configured to for each nucleotide sequence in the second portion, determine whether the nucleotide sequence belongs to one of the known species based on the classification of the first set of nucleotide sequences.

The apparatus comprises a graphical user interface to provide a graphical presentation of classification of the first set of nucleotide sequences.

In general, in another aspect, an apparatus for analyzing nucleotide sequences comprises a data storage to store data representing a first set of nucleotide sequences, the first set having a first number of nucleotide sequences; and a data processor configured to process the data and form a segment-sequence matrix in which rows of the matrix represent the nucleotide segments and columns of the matrix represent the sequences, each element in the matrix representing a repetition frequency of the segment represented by the corresponding row within the sequence represented by the corresponding column; determine a set of basis vectors that can be used to approximately represent the first set of nucleotide sequences, the set having a second number of basis vectors, in which the second number is smaller than the first number, and each basis vector represents a specific combination of predetermined nucleotide segments, in which the determine a set of basis vectors comprises apply at least one of non-negative matrix factorization or singular value decomposition to the segment-sequence matrix to determine the basis vectors.

Implementations of the apparatus may include one or more of the following features. The data processor is configured to determine a projection matrix based on the basis vectors, and project segment-sequence vectors into a feature space based on the projection matrix.

The data storage is configured to store a second set of nucleotide sequences that includes nucleotide sequences from a host and nucleotide sequences from a plurality of species different from the host; and the data processor is configured to project the second set of nucleotide sequences into the feature space; cluster the projected sequences in the feature space; and identify one or more clusters that are primarily associated with the host.

The apparatus comprises a graphical user interface to provide a graphical presentation of clustering of the projected sequences in the feature space.

The data storage is configured to store a second set of nucleotide sequences that includes nucleotide sequences from a host and nucleotide sequences from a plurality of known species different from the host; and a third set of nucleotide sequences that includes nucleotide sequences from either the host or other species without information on which nucleotide sequences in the third set belong to the host; and the data processor is configured to project the second and third sets of nucleotide sequences into the feature space; cluster the projected sequences in the feature space; identify one or more clusters that are primarily associated with the host; and remove sequences from the third set that are in the one or more clusters primarily associated with the host.

The plurality of known species comprises known species of at least one of prokaryotes, eukaryotes, or viruses, and the third set of nucleotide sequences are obtained from the host.

The data processor is configured to, for each of the first set of nucleotide sequences, determine an approximate representation of the nucleotide sequence based on a combination of the basis vectors; for each pair of a plurality of pairs of nucleotide sequences, determine a distance between the pair of nucleotide sequences according a distance between the approximate representations of the pair of nucleotide sequences; and classify the first set of nucleotide sequences based on the distances between the pairs of nucleotide sequences.

The distance between the approximate representations of the pair of nucleotide sequences is determined according at least one of (i) Euclidean distance between the approximate representations of the pair of nucleotide sequences or (ii) correlation between the approximate representations of the pair of nucleotide sequences.

The data processor is configured to determine the distance between every pair of nucleotide sequences, and classify the first set of nucleotide sequences based on the distances between all of the pairs of nucleotide sequences.

A first portion of the first set of nucleotide sequences belong to known species of at least one of prokaryotes, eukaryotes, or viruses, a second portion of the first set of nucleotide sequences are obtained from a patient, and the data processor is configured to, for each nucleotide sequence in the second portion, determine whether the nucleotide sequence is associated with one of the known species of the at least one of prokaryotes, eukaryotes, or viruses based on the classification of the first set of nucleotide sequences.

Determine an approximate representation of the nucleotide sequence based on a combination of the basis vectors comprises determine an approximate representation of the nucleotide sequence based on a linear combination of the basis vectors.

Determine an approximate representation of the nucleotide sequence comprises determine coefficients for a linear combination of the basis vectors that represents an approximation of the nucleotide sequence.

A first portion of the first set of nucleotide sequences belong to known species, species of a second portion of the first set of nucleotide sequences initially being unknown, and the data processor is configured to, for each nucleotide sequence in the second portion, determine whether the nucleotide sequence belongs to one of the known species based on the classification of the first set of nucleotide sequences.

The predetermined nucleotide segments are k-mers each having k nucleobases, k being a positive integer, and each basis vector represents a specific combination of the k-mers.

In general, in another aspect, an apparatus for analyzing nucleotide sequences comprises a data storage to store first data representing a first set of nucleotide sequences that includes nucleotide sequences from a host and nucleotide sequences from a plurality of known species different from the host, and second data representing a second set of nucleotide sequences that includes nucleotide sequences from either the host or other species without information on which nucleotide sequences in the second set belong to the host; and a data processor configured to process the data and generate a segment-sequence vector for each of the nucleotide sequences in the first and second sets of nucleotide sequences, the segment-sequence vector providing information on nucleotide segments included in the nucleotide sequence; project the segment-sequence vectors for the first and second sets of nucleotide sequences into a feature space; cluster the nucleotide sequences in the feature space; identify one or more clusters that are primarily associated with the nucleotide sequences from the host; and remove nucleotide sequences from the second set of nucleotide sequences that are in the one or more clusters primarily associated with the nucleotide sequences from the host.

Implementations of the apparatus may include one or more of the following features. The data processor is configured to form a segment-sequence matrix in which rows of the matrix represent the nucleotide segments and columns of the matrix represent known nucleotide sequences from a third set of nucleotide sequences, in which each element in the matrix represents a repetition frequency of the segment represented by the corresponding row within the sequence represented by the corresponding column, and the third set of nucleotide sequences includes nucleotide sequences from the host and nucleotide sequences from one or more of the plurality of known species different from the host; and determine a set of basis vectors that can be used to approximately represent the third set of nucleotide sequences, each basis vector representing a specific combination of predetermined nucleotide segments; wherein project the segment-sequence vectors for the first and second sets of nucleotide sequences into a feature space comprises apply a projection matrix to the segment-sequence vectors to project the segment-sequence vectors into the feature space, the projection matrix being determined based on the basis vectors.

The third set of nucleotide sequences is different from the first set of nucleotide sequences.

The nucleotide sequences remaining in the second set of nucleotide sequences form a third set of nucleotide sequences, and the data processor is configured to project the segment-sequence vectors for the first and third set of nucleotide sequences into the feature space; cluster the nucleotide sequences in the feature space; identify one or more clusters that are primarily associated with the nucleotide sequences from the host; and remove nucleotide sequences from the third set of nucleotide sequences that are in the one or more clusters primarily associated with the nucleotide sequences from the host.

In general, in another aspect, an apparatus for analyzing nucleotide sequences comprises a data storage to store a set of nucleotide sequences, the set having a first number of nucleotide sequences; and a data processor configured to process the data and determine a set of basis vectors, the set having a second number of basis vectors, in which the second number is smaller than the first number, and each basis vector represents a specific combination of predetermined nucleotide segments; and for each of the basis vectors, determine a segment that is more strongly associated with the basis vector than the other segments.

Implementations of the apparatus may include one or more of the following features. The data processor is configured to provide information about the nucleotide segments that are more strongly associated with the basis vectors.

The set of nucleotide sequences belong to known species of at least one of prokaryotes, eukaryotes, or viruses.

The predetermined nucleotide segments are k-mers each having k nucleobases, k being a positive integer, and each basis vector represents a specific combination of the k-mers.

Determine a set of basis vectors comprises form a k-mer-sequence matrix in which rows of the matrix represent the k-mers and columns of the matrix represent the nucleotide sequences, and each element in the matrix represents a repetition frequency of the segment represented by the corresponding row within the sequence represented by the corresponding column, and apply at least one of non-negative matrix factorization or singular value decomposition to the k-mer-sequence matrix to determine the basis vectors.

Determine a set of basis vectors comprises form a segment-sequence matrix in which rows of the matrix represent the nucleotide segments and columns of the matrix represent the sequences, each element in the matrix representing a repetition frequency of the segment represented by the corresponding row within the sequence represented by the corresponding column, and apply at least one of non-negative matrix factorization or singular value decomposition to the segment-sequence matrix to determine the basis vectors.

Determine an approximate representation of the nucleotide sequence based on a combination of the basis vectors comprises determine an approximate representation of the nucleotide sequence based on a linear combination of the basis vectors.

In general, in another aspect, an apparatus comprises a microarray having probes that are configured to detect a plurality of nucleotide segments that are associated with a plurality of basis vectors, in which each of the basis vectors represents a specific combination of predetermined nucleotide segments, and the basis vectors are derived from a plurality of nucleotide sequences by forming a segment-sequence matrix in which rows of the matrix represent the nucleotide segments and columns of the matrix represent the sequences, each element in the matrix representing a repetition frequency of the segment represented by the corresponding row within the sequence represented by the corresponding column, and applying a dimension reduction process to the segment-sequence matrix to determine the basis vectors.

Implementations of the apparatus may include one or more of the following features. Applying a dimension reduction process comprises applying at least one of non-negative matrix factorization or singular value decomposition to the segment-sequence matrix to determine the basis vectors.

The details of one or more of the above aspects ad implementations are set forth in the accompanying drawings and the description below. Other features, aspects, and advantages will become apparent from the description, the drawings, and the claims.

DESCRIPTION OF DRAWINGS

FIGS. 12-17 are graphs.

Like reference symbols in the various drawings indicate like elements.

DETAILED DESCRIPTION

Figure 1:
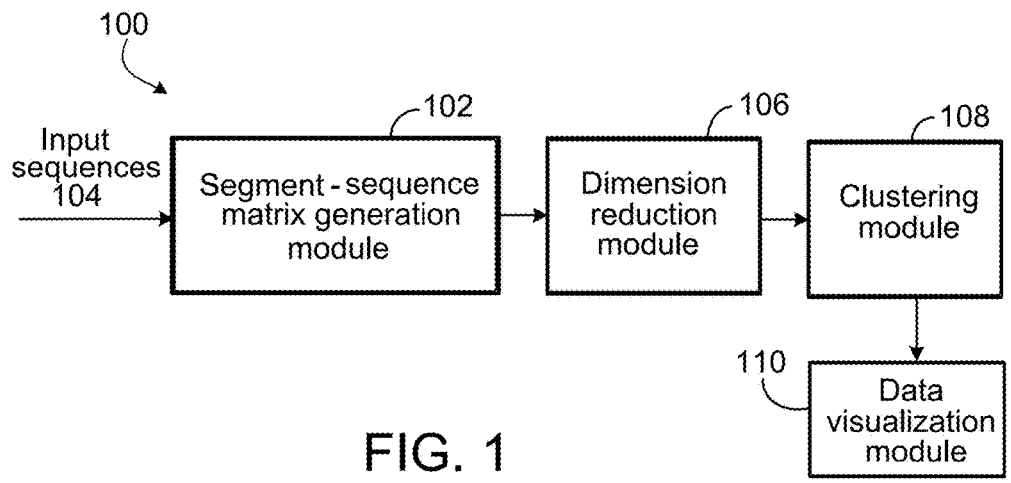
FIGS. 1 and 2 are block diagrams of exemplary systems that use latent semantic analysis for analyzing DNA sequences.
Figure 2:
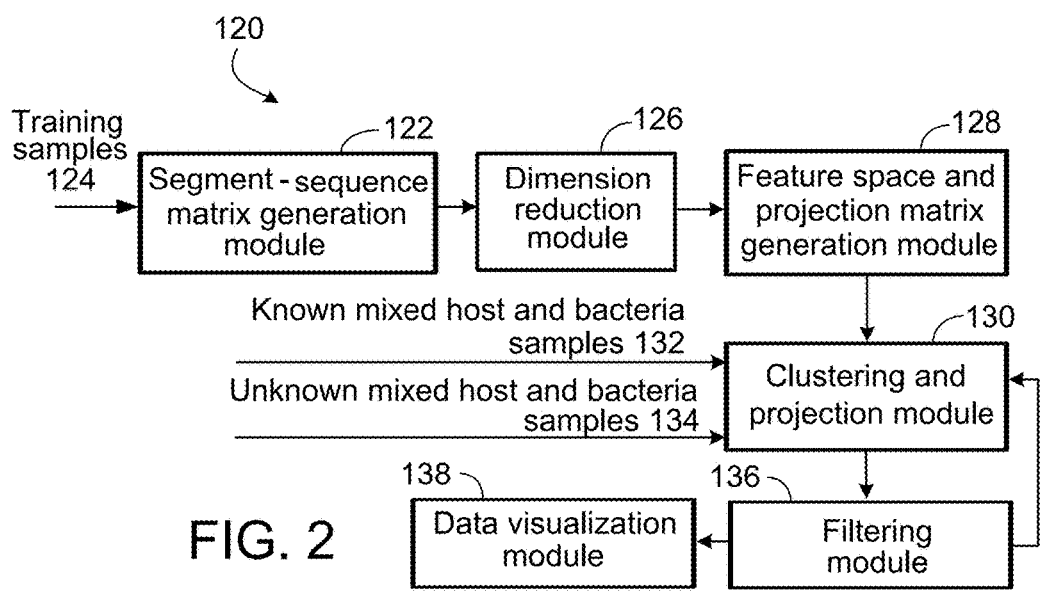
Figure 3:
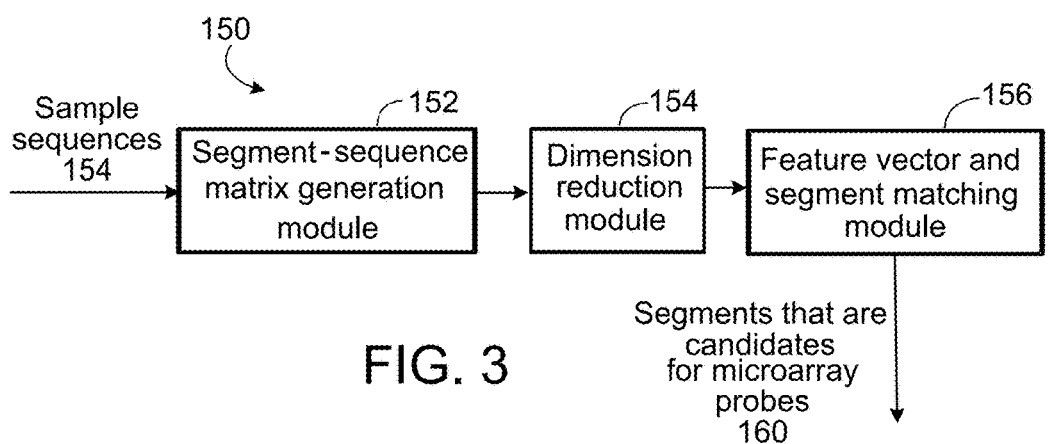
FIG. 3 is a block diagram of an exemplary system that use latent semantic analysis for designing microarray probes.

This disclosure provides a novel approach for identifying similar DNA sequences using latent semantic analysis (LSA). FIGS. 1-3 are diagrams of systems that can analyze DNA sequences using latent semantic analysis. A description of the systems is provided, followed by a more detailed explanation of how latent semantic analysis is implemented in these systems.

Referring to FIG. 1, in some implementations, a system 100 that uses latent semantic analysis for analyzing DNA sequences includes a segment-sequence matrix generation module 102 that receives a set of DNA sequences 104 to be analyzed and generates a corresponding segment-sequence matrix. DNA segments are used as basic components or vocabulary for analyzing the DNA sequences. In some examples, the DNA segments are k-mers. The segment-sequence matrix provides information on which sequences have which segments. A dimension reduction module 106 applies dimension reduction to the segment-sequence matrix to determine a set of basis vectors or feature vectors. For example, the dimension reduction module 106 can use non-negative matrix factorization or singular value decomposition algorithm in the process of dimension reduction. The number of basis vectors is less than the number of segments. Each basis vector represents a combination or collection of DNA segments, and each DNA sequence can be approximately represented by a combination (e.g., linear combination) of the basis vectors.

Profile vectors that represent the linear combination coefficients provide information on the characteristics of the DNA sequences. The profile vectors can be regarded as providing coordinates of the DNA sequences in a feature space having dimensions defined by the basis vectors. A clustering module 108 clusters the profile vectors in the feature space such that similar DNA sequences are clustered closely in the feature space, and DNA sequences that are different are spaced apart in the feature space. The distance or correlation of the profile vectors of two DNA sequences provide information on how similar or different the sequences are. A data visualization module 110 allows a user to visualize the clustering of the sequences.

For example, based on the clustering, the user can determine which species are more closely related. If the input sequences 104 include known samples and unknown samples, the user can determine whether the unknown samples are related to one or more of the known samples. By changing the number of dimensions in the dimension reduction module 106, the user can change the number of clusters, effectively moving up or down the taxonomic hierarchy. For example, by choosing a smaller number of dimensions, the system 100 can produce a smaller number of clusters, allowing the user to classify the sequences according to a higher taxonomy level. By choosing a larger number of dimensions, the system 100 can produce a larger number of clusters, allowing the user to classify the sequences according to a lower taxonomy level.

Because the dimensions of the profile vectors can be small (e.g., less than 10), the system 100 can determine the distances between DNA sequences easily by determining the distances between the corresponding profile vectors. The system 100 can analyze a large number of DNA sequences quickly to identify clusters of sequences, providing information on which sequences are similar and which sequences are different. DNA sequences from known species can be used to establish a feature space, profile vectors corresponding to DNA sequences from unknown species can be projected into the feature space, and the unknown species can be classified based on the projections. For example, an unknown sample of a bacterium sample can be quickly analyzed to determine whether it is similar to a cluster of benign bacteria or a cluster of high risk bacteria.

Referring to FIG. 2, in some implementations, a system 120 that uses latent semantic analysis can analyze samples taken from an environment, such as bacterial samples taken from the body of a host animal. The number of bacterial DNA sequence samples to be analyzed may be small compared to the number of DNA sequence samples from the host animal.

A segment-sequence matrix generation module 122 receives a set of training DNA sequences 124 that includes sample sequences from the host animal and sample sequences of one or more bacteria to be analyzed, and generates a corresponding segment-sequence matrix. A dimension reduction module 126 applies dimension reduction to the segment-sequence matrix to determine a set of basis vectors or feature vectors. For example, the dimension reduction module 104 can use non-negative matrix factorization or singular value decomposition algorithm. Using the basis vectors, a feature space and projection matrix generation module 128 defines a feature space. A projection matrix is generated to enable an unknown sample to be projected into the feature space.

A clustering and projection module 130 receives information about the feature space and the projection matrix from the feature space and projection matrix generation module 128. The clustering and projection module 130 receives a first set of known samples of mixed host and bacterial DNA sequences 132, and a second set of unknown samples of mixed host and bacterial DNA sequences 134. The clustering and projection module 130 projects the first set of known samples into the feature space and clusters the projected samples in the feature space. Some of the clusters are primarily associated with the host sequences, and some of the clusters are primarily associated with the bacterial samples.

The clustering and projection module 130 projects the second set of unknown samples into the feature space and clusters the unknown samples along with the known samples. A filtering module 136 removes the unknown samples that are grouped with the clusters associated with the host samples from the second set. This provides a filtering mechanism for filtering the host DNA sequences such that the remaining unknown samples in the second set has a much higher percentage of bacterial samples. The filter process can be repeated to further reduce the amount of host samples. A data visualization module 138 allows a user to visualize the clustering of the sequences.

Microarray probes can be designed based on the results of latent semantic analysis of DNA sequences. Suppose a microarray is designed to detect the DNA sequences of a set of M species. By applying latent semantic analysis, a set of M feature vectors can be determined in which each feature vector roughly corresponds to one of the species. By analyzing the level of association between a feature vector and all of the segments, it may be possible to determine which segment is more strongly associated with the feature vector. If an unknown DNA sequence includes a particular segment, there is a high likelihood that the DNA sequence is associated with a particular feature vector associated with the segment, and thus belongs to the species associated with the feature vector. The segments that have high levels of associations with the feature vectors can be used to design the probes for the microarrays.

Referring to FIG. 3, in some implementations, a system 150 uses latent semantic analysis to design microarray probes for use in microarray chips intended to detect a predetermined set of DNA sequences. The system 150 includes a segment-sequence matrix generation module 152 that receives sample sequences belonging to the set of DNA sequences, and generates a corresponding segment-sequence matrix. A dimension reduction module 154 applies dimension reduction to the segment-sequence matrix to determine a set of basis vectors or feature vectors. For example, the dimension reduction module 104 can use non-negative matrix factorization or singular value decomposition algorithm. Each basis vector represents a combination or collection of DNA segments, and each DNA sequence can be approximately represented by a linear combination of the basis vectors.

A feature vector and segment matching module 156 analyzes the level of association between each feature vector and the segments to determine which segment is more strongly associated with the feature vector. For each feature vector, the segment that is most strongly associated with the feature vector is identified. The segments that are strongly associated with the feature vectors are output as candidates for microarray probes 160.

The following describes the principles of systems 100 (FIG. 1), 120 (FIG. 2), and 150 (FIG. 3) in more detail.

Biology Background

To facilitate the discussion of using latent semantic analysis for comparing DNA sequences, the following provides a brief background on what the DNA sequences are and some definitions of the terms used in this description. DNA is regarded as a genetic code or blueprint used to construct living things.

DNA is an acronym for deoxyribonucleic acid and is a double-stranded macromolecule that includes four basic structural units called nucleotides. Nucleotides are the building blocks for generating DNA sequences, and much like how sentences can be formed using strings of letters from the alphabet, a DNA sequence can be formed of a string of nucleotides.

A nucleotide molecule includes three main parts: a five-carbon sugar, a phosphate group, and a nitrogenous base or nucleobase. There are four different nucleotides, each differing only in the nucleobase. The four nucleobases are adenine (A), guanine (G), thymine (T), and cytosine (C). When referring to a nucleotide, we typically mean to indicate the attached base, which we denote using its one letter abbreviation. Accordingly, this set of four letters forms the basis for our "DNA alphabet".

Certain bases naturally pair or bind to one another. Specifically, adenine pairs with thymine (A-T), and guanine with cytosine (G-T). These complementary nucleotides are held together by hydrogen bonds that link the two molecules, forming a base pair (bp). Because DNA includes a string of these pairs, we typically express the length of a sequence in terms of its number of base pairs. These chemical properties ensure that each nucleotide bonds only to its pair, which we refer to as its complementary base or simply its complement.

The DNA macromolecule includes two, complementary strands of nucleotides which are held together by hydrogen bonds. Each strand has so-called 5' (read as "five prime") and 3' ends. The chemical structure of the macromolecule provides directionality in the way that DNA is constructed. When we talk about reading a DNA sequence, we name off the bases from the 5' end towards the 3' end on one of the strands.

In order differentiate between the two complementary strands of DNA, we typically label one as the forward strand and refer to the other as the reverse strand. Conventionally, for a given segment of DNA, we refer to the corresponding portion of the opposite strand as the reverse complement. For example, a segment AGT is the reverse complement of a segment ACT. Due to the opposite or antiparallel orientation of the two strands of the DNA macromolecule, and the stacking forces between nucleobases, the DNA macromolecule twists around itself, forming a double-helix structure.

The primary function of an organism's genome (or complete DNA sequence) is to store the genetic code or set of instructions that determine how the organism is to be built. Portions of the genome, called genes, contain specific instructions for how to create proteins and can also be used to send signals within the cell or even control other genes.

Proteins can be thought of as the machinery inside cells of living things. They perform various functions from converting food into energy to defending our bodies from harmful bacteria. The word "protein" itself comes from the Greek word "prota" meaning "of primary importance."

Because of the macromolecule's double-helix structure, DNA sequences are in general well-protected, and the likelihood of a change occurring is low. When a change or mutation does occur, it can have a wide variety of impact on the organism. Often, mutations have little impact and are either ignored or corrected by error-checking proteins inside the cell. Less frequently, a mutation will significantly affect some function within the organism. This change could be advantageous, or as is the case with certain types of cancer, the mutation could be lethal. If the mutation is advantageous or has little to no impact on the organism, it stands a chance of being permanently incorporated into the organism's genome and being passed on to future generations.

When a change is incorporated into a genome, particularly one that benefits the organism, we say that the organism has evolved in some capacity. These changes, however slowly, contribute to the level of genetic diversity between species. From this, assuming that all forms of life have evolved from a common ancestor, it follows that the level of similarity in the genomic sequences for two species provides an indication of their evolutionary distance and, thus, functional similarity.

This disclosure provides computationally efficient techniques for estimating the evolutionary distance between DNA sequences. By clustering or grouping sequences together based on evolutionary similarity, we are able to identify and investigate the similarities and differences between related organisms. In turn, this ability to compare sequences provides us with a way to decipher the genetic code in which they are written.

Comparing DNA Sequences Using Latent Semantic Analysis

Latent semantic analysis is a collection of techniques that can be used to identify and partition similar text documents. For example, latent semantic analysis can use words in dictionaries to analyze the content of text documents. One difficulty in applying latent semantic analysis in analyzing DNA sequences is that DNA sequences do not have readily available dictionaries that include words suitable for analyzing DNA sequences. Thus, we need to generate our own "words" or vocabulary for analyzing the DNA sequences.

In some implementations, latent semantic analysis involves four steps:

(1) Formation of a term-document matrix.
(2) Transformation/modified weighting of term-document matrix.
(3) Dimensionality reduction.
(4) Clustering of documents in the reduced space.

We first describe the use of latent semantic analysis in analyzing text documents, then describe how latent semantic analysis can be used in analyzing DNA sequences. When analyzing text documents, the latent semantic analysis starts with the formation of a term-document matrix, which uses a vector space model to describe the text documents based on the words they contain. For example, imagine for a moment that we have a language L, consisting of the set of words $$L=\{\text{"good","nice","play","The","was"}\}. \quad \text{(Equ. 1)}$$

We can construct a few sentences using this language, such as the following sentences:

S1="The play was good"
S2="The play was nice"

We can represent sentences S1 and S2 with binary vectors whose elements indicate the presence or absence of every word in the language L. This representation is known as a "bag-of-words model" in which a sentence or entire text document is characterized by an unordered collection of words. Using the language L, we can describe S1 with the vector $v_{S_1}$=<good?, nice?, play?, The?, was?>=<1, 0, 1, 1, 1>
and S2 with
$v_{S_2}$=<0, 1, 1, 1, 1>.

These vectors are compiled into a matrix called a "term-document matrix" in which the rows represent individual terms or words, and the columns represent our collection of documents. This matrix forms the starting point for the latent semantic analysis techniques from which we can begin comparing document vectors.

In some examples, a binary weighting used to denote the presence or absence of individual terms may not be enough information to distinguish between two documents. Moreover, at least in the case of natural languages, we expect certain words to appear in every document. For instance, words like "and", "a", and "the" are statistically very likely to occur in every document that we are comparing. As a result, in order to highlight the differences between documents, frequently occurring "stop words" can be removed. In addition, the binary weighting scheme can be replaced with a more detailed measure.

For example, an alternative to binary weighting is the "term frequency" (tf) weighting scheme. This weighting counts the number of occurrences for every term in the language and normalizes the term-document vector by the total number of words in the document. After normalization, each element in the vector indicates the fraction of the document represented by the corresponding term.

An extension to the tf weighting is the "term frequency-inverse document frequency" or tf-idf measure. This weighting attempts to emphasize the presence of words that occur infrequently and deemphasize words that appear throughout the corpus. To compute the inverse document frequency for a term $t_i$, we define $n_i$ to be the number of documents in the corpus that contain $t_i$. If the total number of documents is N, the inverse document frequency for $t_i$ is given by $$idf_i = \log \frac{N}{n_i}. \quad \text{(Equ. 2)}$$

By multiplying each element of a term-document vector by the corresponding term's inverse document frequency, we reduce the strength of terms that appear frequently throughout the corpus. In doing so, we identify terms that can be used to differentiate our documents. A nice property of this technique is that, because stop words occur so frequently, they are essentially removed by the weighting, eliminating the need to manually detect and remove stop words.

An important issue is the choice of words in latent semantic analysis. Multiple words may share the same meaning (referred to as synonymy). Consider sentences S1 and S2 in the example above. By searching for a "good play," a system based solely on lexical matching may return S1 but may leave out S2, despite its similar positive review. Single words can have multiple meanings, referred to as polysemy. In sentences S1 and S2 above, a person may interpret these sentences as describing some theatrical production. However, it is possible that S1 is referring to a play in the first half of a football game, and S2 is referring to something completely different.

To overcome problems due to synonymy and polysemy, latent semantic analysis uses dimensionality reduction techniques to identify sets of correlated words that are used to describe a similar topic. In doing so, we achieve a way of comparing and retrieving documents that is less affected by discrepancies in word choice.

Dimensionality Reduction Techniques

Latent semantic analysis involves dimensionality reduction, such as mapping term-document vectors into a lower-dimensional space. This has two advantages. First, dimensionality reduction reduces the size of data to be analyzed. A language may contain a large number of words, and it would be more computationally efficient if we can avoid vectors of this length. Dimensionality reduction provides us with a method of grouping correlated words into a single dimension. This helps us to address issues that arise out of linguistic ambiguities, or difference in word choice.

For example, there are two methods for dimensionality reduction: singular value decomposition (SVD) and non-negative matrix factorization (NMF). To indicate which dimensionality reduction routine is used, we use the notation "LSA-SVD" or "LSA-NMF" to denote latent semantic analysis that uses singular value decomposition or non-negative matrix factorization, respectively.

Singular Value Decomposition

For example, in latent semantic analysis, we can begin with a t×d term-document matrix X, in which t represents the number of terms in the language and rows in X, and d is the number of documents in the corpus. Using singular value decomposition, we can find an approximation for X that groups collections of correlated terms into a small number of dimensions. Using singular value decomposition, we transform the data into a new set of fewer variables that capture the majority of the variance in the original variables, highlighting the primary characteristics of the data. The following describes a mathematical derivation for singular value decomposition and its application to latent semantic analysis.

Using singular value decomposition, a t×d matrix X is factorized as $$X = U\Sigma V^T. \quad \text{(Equ. 3)}$$

Here, U is a t×n unitary matrix in which the columns represent orthonormal eigenvectors of $XX^T$, where n≤d and typically d<<t. Similarly, the rows of $V^T$ are orthonormal eigenvectors of $X^TX$, forming an n×d matrix, and E is an n×n diagonal matrix having entries sorted in descending order. The diagonal entries of E are called the singular values or principal values of X, and they represent the real, non-negative square roots of the eigenvalues of $X^TX$ and $XX^T$.

The factorization is based on the notion that we can construct n eigenpairs $\{\lambda_i, v_i\}_{i=1 \ldots n}$ for the matrices $X^TX$ and $XX^T$, in which $v_i$ is an eigenvector having corresponding eigenvalue $\lambda_i$. The eigenpair $\{\lambda_i, v_i\}$ is defined such that the following equation holds:

$$Av_i = \lambda_i v_i \quad \text{(Equ. 4)}$$

By transforming or multiplying vector $v_i$ by the matrix A, we obtain a scalar multiple ($\lambda_i$) of the vector itself. Replacing A in Equation 4 with the matrix $X^TX$, we notice the following property:

$$(X^TX)v_i = \lambda_i v_i$$

$$X(X^TX)v_i = X\lambda_i v_i$$

$$(XX^T)Xv_i = \lambda_i Xv_i \quad \text{(Equ. 5)}$$

From Equation 5, we see that for an eigenvector $v_i$ of $X^TX$, $Xv_i$ is an eigenvector of $XX^T$ having the same eigenvalue $\lambda_i$. We can construct the singular value decomposition of X by finding the eigenvectors of $X^TX$ and $XX^T$ and arranging them into matrices U and $V^T$ such that the i-th column of U and i-th row of $V^T$ correspond to the same singular value $\sigma_i$ in $\Sigma$. For convenience, we arrange these matrices such that the singular values of $\Sigma$ are listed in descending order of magnitude.

For example, some algorithms and implementations of singular value decomposition compute the eigenpairs by first reducing a matrix X to a bidiagonal matrix, which is reduced to a diagonal matrix containing the singular values. To enhance performance, QR factorization is added as a preliminary step before bidiagonalization, resulting in the following steps for singular value decomposition:

(1) Compute QR factorization of X. (X=QR)
(2) Reduce R into a bidiagonal matrix using orthogonal transformations. ($R = U_1 B V_1$)
(3) Reduce B to a diagonal matrix $\Sigma$ using an iterative approach.

After computing these steps, the original matrix X is factorized as $X = U\Sigma V^T$. This leaves us with an encoding for our original set of documents that uses an orthogonal basis set to capture the majority of the variance in X. The diagonal matrix $\Sigma$ provides us with an indication of which of these basis vectors correspond to dimensions having the most variance. These vectors correspond to the highest singular values in $\Sigma$, and by ignoring dimensions with relatively low variance, we achieve a way of dimensionality reduction that captures the underlying structure of the data while reducing the impact of correlated words.

Dimensionality Reduction by Singular Value Decomposition

After performing singular value decomposition on a term-document matrix X, the set of document vectors are approximated by linear combinations of orthogonal basis vectors or "pseudo-documents." Some of these basis vectors are considered to be more important than others in the sense that they capture more of the variance in X and are therefore more important in reconstructing its rows and columns. As a result, if we take only the k most important vectors, corresponding to the k largest singular values in $\Sigma$, we are left with a "truncated singular value decomposition" that can be used to approximate X.

$$X \approx U_k \Sigma_k V_k^T. \quad \text{(Equ. 6)}$$

This truncated singular value decomposition forms a least squares approximation for X that uses k dimensions to describe a majority of the variance in the original matrix. Through this process, correlated dimensions in the original term-space are collapsed into a single dimension in the reduced "LSA space." As a result, we are left with the rows $U_k$ forming a collection of uncorrelated, basis vectors that can be used to reconstruct term-vectors in the reduced space. Similarly, the columns of $V_k^T$ form a basis set for reconstructing document vectors.

By expressing text documents as linear combinations of the basis vectors, the impact of linguistic disparities, such as synonymy and polysemy, is greatly reduced, and nearby vectors in the latent semantic analysis space are related based on their conceptual content. An information retrieval system can be defined by projecting a query vector into this space and gathering or clustering nearby documents.

Non-Negative Matrix Factorization

The set of matrices produced by the singular value decomposition of a term-document matrix has an interesting property. When approximating a document vector in a latent semantic analysis space, the contribution of a basis vector (which indicates the presence of a group of one or more correlated terms) is allowed to take on a negative value. This is due to the requirements for orthogonality in the basis set.

In some implementations for dimensionality reduction, the reconstruction of items uses only non-negative multiples of a set of basis vectors. In this way, vectors either possess a certain quality or not. A collection of algorithms implementing this type of decomposition is known as "non-negative matrix factorization." Non-negative matrix factorization operates by approximating a non-negative matrix X (which can be a collection of term-document vectors) as the product of two non-negative factors A and Y, $$X \approx AY \quad \text{(Equ. 7)}$$

where A is a t×k matrix of basis elements, and Y is a k×d matrix of coefficients/encodings. Here, d indicates the number of vectors being approximated, t is the size of these vectors, and k is the number of elements in the basis set. Each column in X is therefore approximated by a linear combination of k basis vectors, using the weights found in the corresponding column of Y. As indicated, non-negative matrix factorization imposes a non-negativity constraint on the matrices A and Y. The result of this constraint is that basis elements are not allowed to have a negative contribution in the approximation of a vector, and as a result, we are left with a set of "feature vectors" as our basis set.

The approach of finding reduced rank non-negative factors to approximate the non-negative matrix X, can be stated generically as the non-negative matrix factorization problem:

"Given a non-negative matrix $X \in R^{t \times d}$ and a positive integer $k < \min\{t, d\}$ find non-negative matrices $A \in R^{t \times k}$ and $H \in R^{k \times d}$ to minimize the functional":

$$\min_{A, Y} f(A, Y) \equiv \frac{1}{2} \|X - AY\|_F^2, \quad \text{(Equ. 8)}$$

such that $A, Y \geq 0$ where $\|\cdot\|_F$ is the Frobenius norm and A, Y≥0 means that every element of A and Y is non-negative. The product AY is a k-dimensional approximation for X, and in some examples k<<min(t, d). The choice for k has an impact on the quality of the approximation, and will depend on application and data.

For example, algorithms for computing the non-negative matrix factorization of a matrix can be based on alternating least squares (ALS) methods. This class of algorithms begins by constructing a random or otherwise initialized set of basis vectors and continues by applying pairs of "alternating" least squares steps to iteratively refine the starting matrix. These methods are based on the fact the optimization problem presented in Equation 8 is convex in either A or Y separately but not simultaneously. Given one matrix, these methods optimize the other matrix using a simple least squares computation in alternating fashion.

The following pseudocode can be used to describe a basic algorithm for computing non-negative matrix factorization using alternating least squares.

Algorithm 1: Basic non-negative matrix factorization algorithm using alternating least squares

```
A = rand(t, k) ;                        /* randomize/initialize A */
for i = 1 to numIterations do
    Solve for Y using A^T AY = A_T X;   /* (Least squares step 1) */
    Set negative entries of Y to zero;  /* (Enforce non-negativity) */
    Solve for A using YY_T A^T = YX^T ; /* (Least squares step 2) */
    Set negative entries of A to zero;  /* (Enforce non-negativity) */
end
```

As can be seen in Algorithm 1 above, non-negative matrix factorization by alternating least squares is a simple procedure. Because of their simplicity, alternating least squares algorithms lend themselves to fast implementations and have been found to outperform other non-negative matrix factorization techniques and even singular value decomposition.

For information retrieval, by using non-negative matrix factorization on a term-document matrix, the resulting set of basis vectors defines a k-dimensional latent semantic space in which each axis signifies a particular topic. We can now represent text documents as a linear combination of a set of base topics, and we can identify related documents as neighboring vectors in the latent sematic space.

A DNA sequence can be characterized by a statistical interpretation of k-mers included in the sequence. A k-mer refers to an oligonucleotide ("oligo") or polymer of length k that denotes a portion or subsequence of some larger sequence. For example, a segment gagacagt is a k-mer of length eight or an "8-mer." The segment gagacagt contains 3-mers (or "trigrams") gag, aga, gac, aca, cag, and agt. Because we have four bases in the alphabet, these trigrams are a small subset of the $4^k$ or, in this case, $4^3 = 64$ possible k-mers.

The k-mers can be used as a basis for a distance metric for comparing DNA sequences. We can expect sequences having similar composition to have a large number of k-mers in common. For example, if we define the sequences $$Q = gagacagt,$$
$$R = gagacat,$$
and
$$T = tcgctta.$$

The set of 3-mers contained within each sequence are denote using Z as follows:

$$ZQ = \{gag, aga, gac, aca, cag, agt\}$$
$$ZR = \{gag, aga, gac, aca, cat\}$$
$$ZT = \{tcg, cgc, gct, ctt, tta\}$$

Because the set of 3-mers in $Z_Q$ is more similar to the set of 3-mers in $Z_R$ than that of $Z_T$, it can be inferred that Q is more similar to R than T.

A sequence can be modeled as an unordered collection of distinct k-mers or a "bag-of-k-mers." Just as latent semantic analysis can use the bag-of-words model for representing text documents, we can treat k-mers as the words in the genetic language. As a result, we can replace the notion of term-document matrices with k-mer-sequence matrices.

In the following, we describe the use of LSA-NMF to identify evolutionarily similar sequences. By using non-negative matrix factorization to profile sequences, we anticipate the set of basis vectors to be indicative of some type of "biological signals" that can be used to differentiate organisms.

Note that other latent semantic analysis techniques, such as LSA-SVD, can also be used to analyze DNA sequences to differentiate organisms.

In the experiments described below, we will project k-mer-sequence vectors into high-dimensional latent semantic spaces (referred to as "feature spaces"). In some implementations, in order to evaluate the closeness of sequences in the feature spaces, we visualize the high-dimensional data in fewer dimensions, such as in a three-dimensional space. In some implementations, a graphical user interface, such as nSpect tool described below, can be used as a visualization tool for analyzing and inspecting high-dimensional data in three dimensions.

Visualizing High-Dimensional Datasets

Visualization provides valuable insight into the overall structure and defining characteristics of a system by reorganizing and mapping data to a visual reference. In order to represent high-dimensional data, we reduce the dimensionality of the dataset such that as much information as possible can be represented graphically, using two or three dimensions.

The following describes visualization of data that can be described using a dissimilarity matrix (proximity data). A dissimilarity matrix (or distance matrix) is a square, symmetric matrix containing scores which indicate the similarity of each pair of objects in a collection. Because most applications typically involve more than two or three items, in order to visualize the dissimilarity matrix, we will use some form of dimensionality reduction.

The collection of techniques used to embed an N×N dissimilarity matrix into a lower-dimensional space is called multidimensional scaling (MDS). These techniques attempt to map high-dimensional data to a low-dimensional representation while preserving pairwise distances as best as possible. A multidimensional scaling technique called principal component analysis (PCA) attempts to reduce the dimensionality of a dataset consisting of a large number of interrelated variables by transforming the data to a new set of uncorrelated variables called principal components. Principal components are ordered or ranked such that the first few variables capture most of the variation present in the original set of attributes. Dimensionality reduction is typically accomplished using the assumption that these first few components convey the majority of the information contained in the original data, and, thus, the remaining components can be ignored.

Another multidimensional scaling algorithm is relational perspective mapping (RPM), which arranges objects on a closed surface in accordance with their pairwise similarity measures. The algorithm treats each item in the dissimilarity matrix as an object in a force-directed, multi-particle system with mutual repulsive forces between each pair of objects. Items with larger relational distances between them exhibit larger repulsive forces, which propel the two objects away from each other on the surface of a torus. Once the objects have reached a stable configuration, the torus is unwrapped to create a two-dimensional relationship mapping. Because this model assigns repulsive forces between every pair of objects in the dataset, the resulting visualization incorporates information from all of the original N dimensions.

The following describes nSpect, an exploratory visualization tool which uses a repulsive force-driven system to visualize high-dimensional proximity data in three dimensions. The nSpect tool treats each element in the visualization as a particle in a three-dimensional free space. The resulting visualization allows users to view and interact with the 3D model as it progresses in real-time.

The nSpect tool receives as input a dissimilarity matrix in the standard, PHYLogeny Inference Package (PHYLIP) format. This matrix serves as a table of values indicating the distances between every pair of objects in the visualization. An entry, $t_{i,j}$, denotes the relative, ideal distance separating the ith and jth elements. The value of $t_{i,j}$ ranges from 0.0 to 1.0, in which 1.0 indicates maximum dissimilarity, and 0.0 suggests equivalency.

Using these distances, nSpect computes repulsive forces between the collection of objects such that the movement produced by the forces results in a new, more appropriate configuration at the next time instance. In order to compute the force between two objects, nSpect first evaluates the error in actual displacement versus a scalar multiple of the ideal distance, $t_{i,j}$, separating the pair.

$$e_{i,j} = (S \times t_{i,j}) - d_{i,j} \qquad \text{(Equ. 9)}$$

Here, the scalar S has been empirically chosen to produce an appropriate size for the visualization. Using this equation, we see that the error indicates the quality of the current arrangement of objects. We define the repulsive force separating two items with the following equation.

$$f_{i,j} = e_{i,j} \times x_{i,j} \qquad \text{(Equ. 10)}$$

Using the error as a weighting, the force vector $f_{i,j}$ acts to repel the ith and jth elements along the three-dimensional direction vector $x_{i,j}$ which separates the two objects. A force equal in magnitude and opposite in direction is applied in the second element. Finally, the net force acting upon the ith element is computed as $$f_i = \Sigma_j f_{i,j} \quad \text{(Equ. 11)}$$

This force vector is calculated for each object in the visualization and is used to determine an appropriate direction and velocity with which to move the particle during the next time instance. The velocity of an object is calculated by $$v_i^{(n+1)} = \alpha(v_i^{(n)} + \beta \times f_i^{(n)}) \quad \text{(Equ. 12)}$$

Here, the superscripts denote the time iteration in the visualization. As is shown, the velocity vector at the next time instance $v_i^{(n+1)}$ is determined by the object's current velocity plus some additional amount induced by its force vector.

$$I_i^{(n+1)} = I_i^{(n)} + \gamma v_i^{(n+1)} \quad \text{(Equ. 13)}$$

The object's new location $I_i^{(n+1)}$ is determined using its current location and computed velocity vector $v_i^{(n+1)}$. In the equations above, the constant $\alpha$ introduces a drag force or decay in velocity. If chosen to be too strong, the drag force could keep objects from escaping local minima, and if too weak, the system is slow to converge. The parameter $\beta$ is similarly chosen to calculate an appropriate velocity for an object given the amount of force applied to it. If chosen to be too strong, the system will not reach a stable condition. If too weak, the rate of convergence suffers considerably. Finally, $\gamma$ represents a default step size, which determines how far an object should move. If the step size is chosen to be too large, the system will not be able to reach a stable condition. If too small, the system will be slow to converge. These constants were experimentally determined to provide a good tradeoff between the rate of convergence and jitter.

As the visualization progresses and objects move into a stable arrangement, one must consider the possibility of objects settling in local minima. To address this issue, objects are randomly displaced by a series of perturbations occurring when the average velocity of the system falls below a threshold. These perturbations diminish in intensity until their effect is negligible.

The nSpect tool can provide a graphical user interface that allows a user to visualize the three-dimensional feature space. Using various controls, the user can explore the feature space by rotating, panning, and zooming in or out.

Because the objects in the visualization are given randomized starting locations and perturbations, the orientation of the final arrangement is also non-deterministic. Acknowledging this fact, the user has the ability to restart the visualization by "jumbling" or randomizing the starting locations of the objects. In addition, the user can manually issue perturbations or shakes to the collection of items. Using nSpect, high-dimensional proximity data can be visually approximated in a simulated, three-dimensional free space.

Clustering of 16s Ribosomal Genes

The following describes an example of using LSA-NMF to partition a collection of 16S ribosomal genes. The term "16S sequence" (or, more formally, a "16S rDNA sequence") refers to a specific gene associated with a structural element of prokaryotic ribosomes. Ribosomes are responsible for assembling proteins. The genes used to produce ribosomes are universal (present in all species), highly conserved, and similar across species, and any differences in these genes can be used as a way of differentiating between the species.

The 16S gene itself is fairly small at around 1,500 bases in length. Although short, this length is sufficient for constructing functional statistical characterizations. Another attractive property of this particular sequence is that there are methods of sequencing it directly and therefore quickly and relatively inexpensively. This short and informative sequence is easy to obtain and inexpensive to store. For these reasons, the 16S sequences are very popular for constructing phylogenies and taxonomic databases. Ribosomal sequence databases, such as Ribosomal Database Project (RDP), are among the largest collections available for comparing related organisms.

In this example, we will apply LSA-NMF to a set of 16S sequences from a collection that includes 268 sequences taken from species belonging to 5 genera: *Bulkholderia, Chryseobacterium, Desulfovibrio, Nocardioides,* and *Shewanella*. We begin with the formation of a k-mer-sequence matrix, X. In some implementations, a k-mer size of 7 is used. This provides a good trade-off between specificity and profile size for this dataset. Lowering the k-mer size may reduce the amount of information being used to compare sequences, effectively lowering the resolution. Going higher than 7 may provide additional resolution, but it may also require increased memory and computation power. In this example, we use k-mers of 7 bases long. The k-mer-sequence vectors are $4^7 = 16,384$ elements long, and X is a $16,384 \times 268$ matrix. After obtaining k-mer frequency counts for each of the 268 sequences, tf-idf weighting was applied to the matrix X in order to deemphasize any similarities and highlight any differences between the k-mer counts.

In some examples, dimensionality reduction can be applied by using the NMF MATLAB Toolbox by Li and Ngom. This toolbox provides a collection of standard non-negative matrix factorization routines. In this example, we use the routine based on an alternating non-negative least squares algorithm. Other techniques for non-negative factorization can also be used.

In this example, because we already know the number of distinct groups in our dataset—there are five genera, we can start by approximating the matrix X using 5 basis vectors. Using the standard, least squares-based algorithm, we obtain the factorization $$X \approx AY, \quad \text{(Equ. 14)}$$

in which A is a set of basis vectors compiled into a matrix of size $16,384 \times 5$, and Y is a $5 \times 268$ matrix of encodings (or coefficients) from which we can reconstruct the original k-mer-sequence vectors using the basis set A.

The encodings in the matrix Y are short profiles that represent the original set of vectors and can be used as a basis for comparing them. As a result, we can form a distance measure by computing the Euclidean distance or correlation coefficient for each pair of vectors in the matrix Y. This can be used as the LSA-NMF-based distance metric. Distance matrices were constructed by computing the Euclidean distance and correlation coefficient of each pair of sequences, i.e., computing the Euclidean distance and correlation coefficient of each pair of vectors in the matrix Y.

Figure 4:
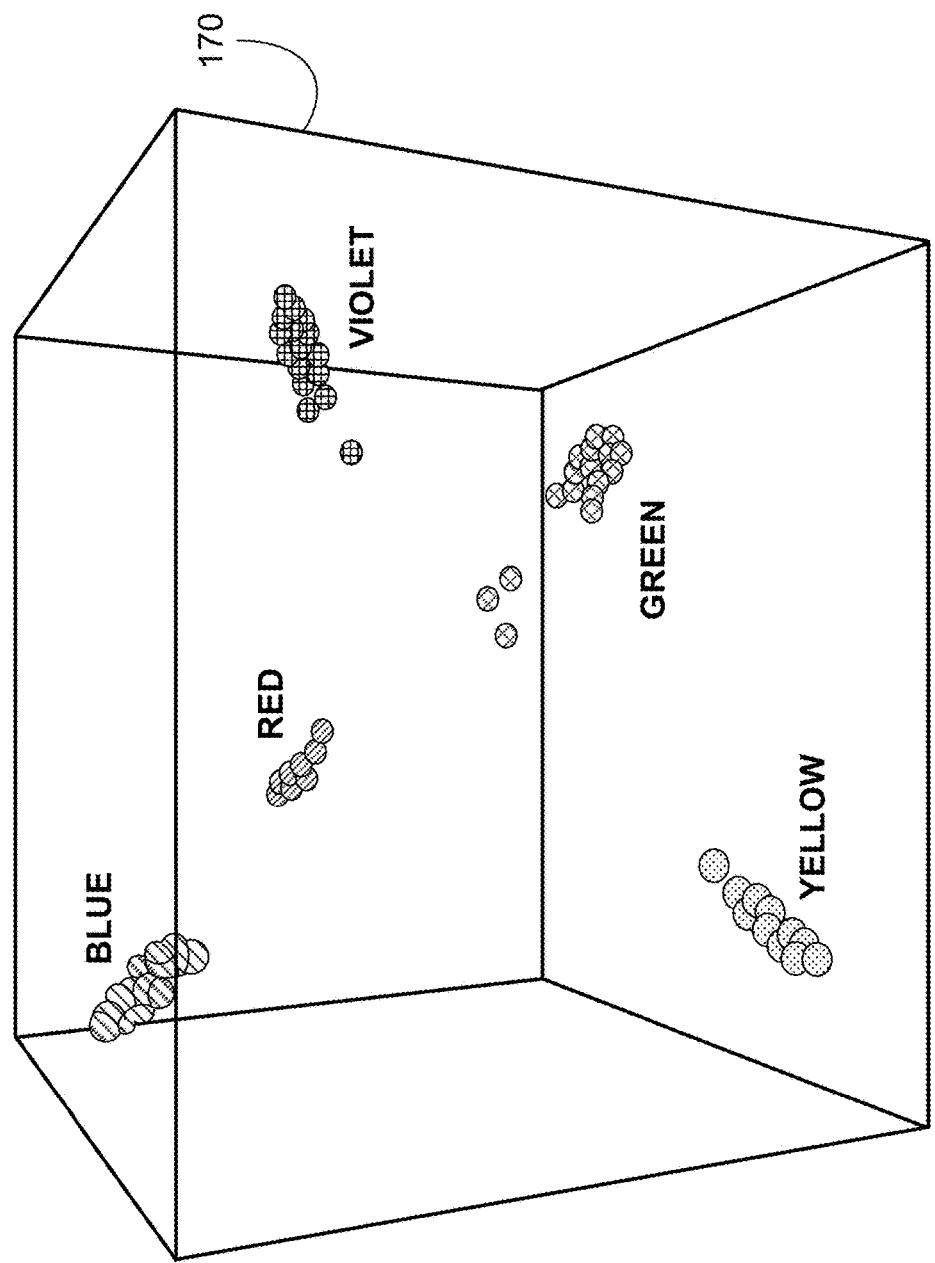
FIGS. 4-10 are graphs.
Figure 5:
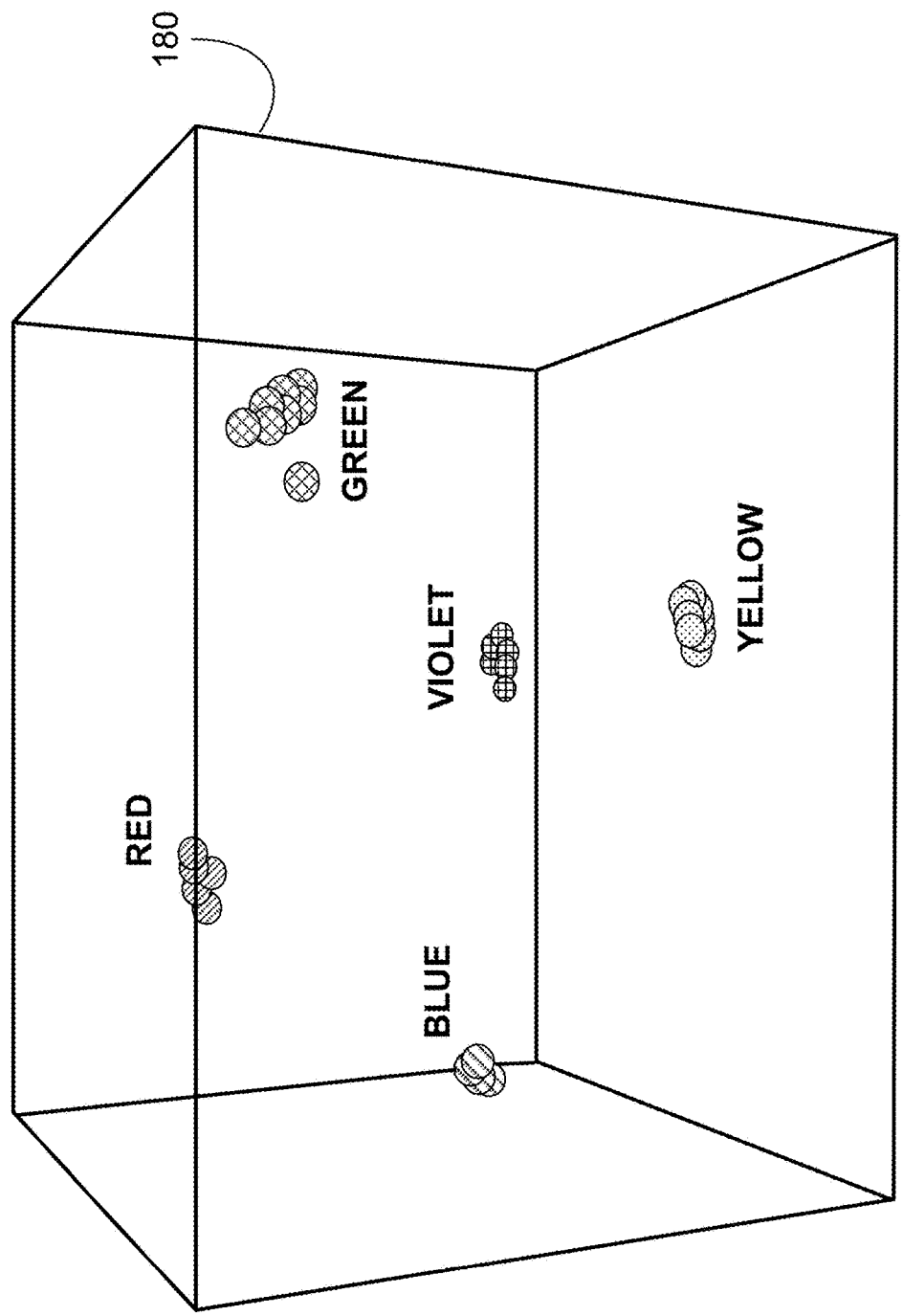

Referring to FIG. 4, a graph 170 produced using the nSpect tool shows approximately how the profiles cluster in high-dimensional space. In graph 170, the distance matrix was constructed by computing the Euclidean distance of each pair of sequences. Referring to FIG. 5, a graph 180 produced using the nSpect tools shows another example of approximately how the profiles cluster in high-dimensional space. In graph 180, the distance matrix was constructed by computing the correlation coefficient of each pair of sequences. The original graphs 170 and 180 generated by the nSpect tool are rendered in color, though the graphs are shown in gray scale in the figures. The colors of the objects in the figures indicate the genus to which each sequence belongs. For example, red=*Burkholderia*, blue=*Chryseobacterium*, green=*Desulfovibrio*, yellow=*Nocardioides*, and violet=*Shewanella*. In each of the graphs 170 and 180, there is considerable separation of the clusters in the 5-dimensional feature space.

In FIGS. 4 and 5, the clusters are well-defined. The dimensionality reduction stage in the latent semantic analysis procedure attempts to identify basis vectors that capture the majority of the variance in the genetic data. As a result, vectors that are heavily correlated, such as ones representing organisms from the same genus, appear to be very similar when projected into the feature space.

In the field of information retrieval, dimensionality reduction allowed us to recognize related documents in spite of large differences in word choice due to the authors' vocabulary and writing style. Here, this same effect provides a level of "noise-reduction" that makes the technique described here less sensitive to small differences between genomic sequences. In the examples shown in FIGS. 4 and 5, non-negative matrix factorization can identify a set of basis vectors that correspond to the centroid of each of the five genera. These basis vectors represent sets of k-mers whose presence denotes a feature in the projected space. The features may indicate the genus of the organism.

Figure 6:
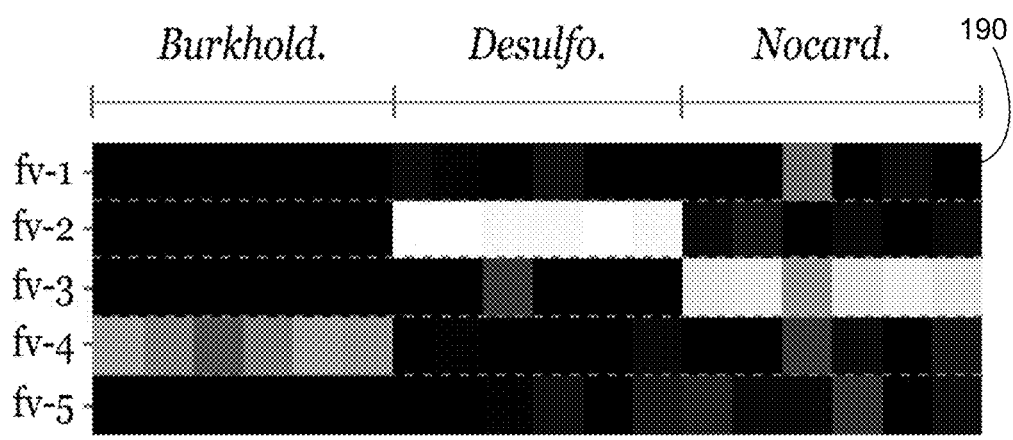

FIG. 6 is a graph 190 showing a sample of elements from the encoding matrix, Y. Each column in the graph 190 presents a grayscale rendering of a column in the matrix Y. White indicates a maximum level of contribution for the feature vector, and black indicates a minimum level of contribution. The graph 190 shows that most sequences from a particular genus associate strongly with just one feature vector. On the other hand, a few columns from the genus *Nocardioides* are not well-defined by any single feature. These columns correspond to outliers that may have been misclassified or mislabeled.

In the examples used to generate graphs 170 and 180 in FIGS. 4 and 5, we know how many genera are present in the dataset. When the number of feature vectors is modified, the number of clusters may also change.

Figure 7:
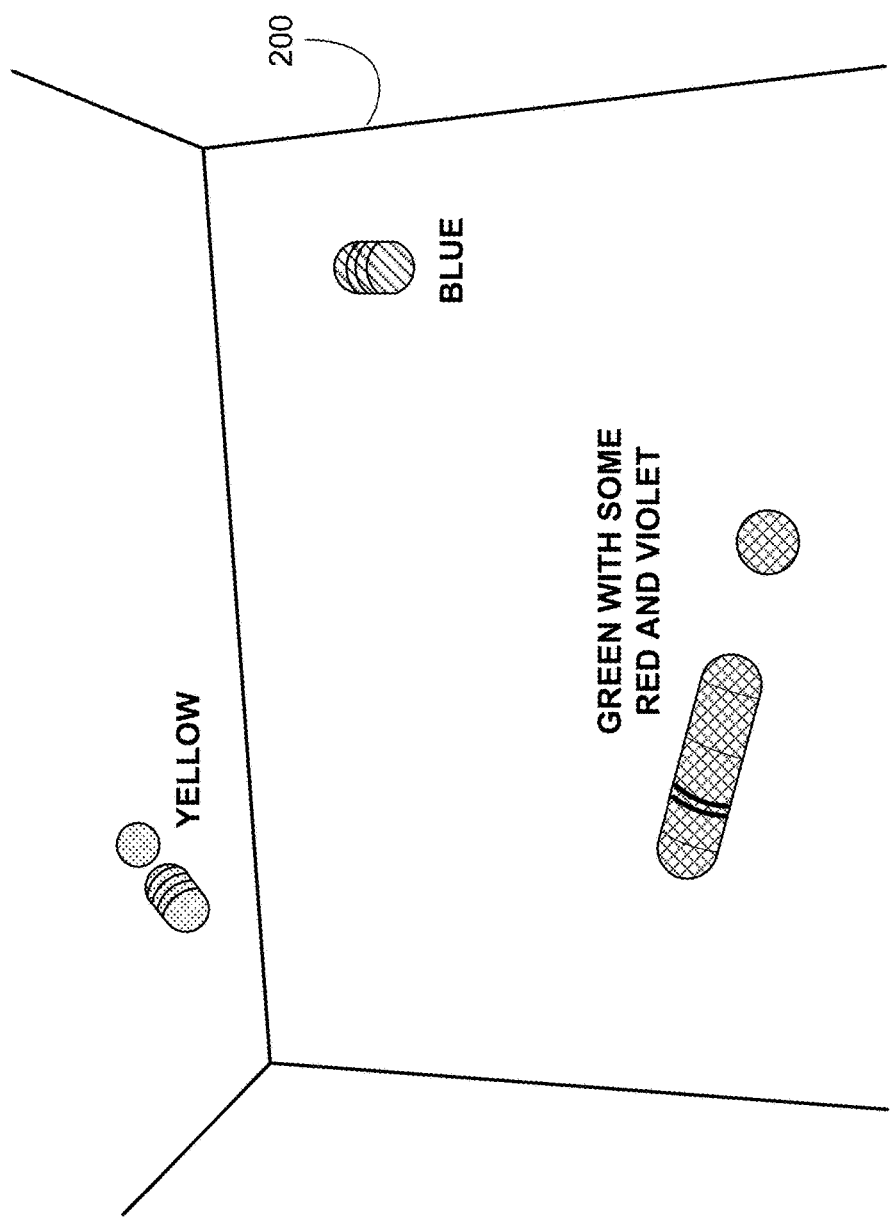

Referring to FIG. 7, for example, if we lower the number of feature vectors to k=3, a graph 200 shows that there will be three clusters. Using this new set of three basis vectors, we see that our genera have been divided into three relatively distinct groups that correspond to the phyla to which they belong. The largest of these three groups contains the three genera *Burkholderia* (red), *Desulfovibrio* (green), and *Shewanella* (violet), while the other two genera *Chryseobacterium* (blue) and *Nocardioides* (yellow) appear to correspond to their own feature vectors.

Upon inspection, the genera *Burkholderia*, *Desulfovibrio*, and *Shewanella* are all Gram-negative genera in the phylum of *Proteobacteria*. On the other hand, *Chryseobacterium* and *Nocardioides*, the remaining genera, belong to the phyla of *Bacteroidetes* and *Actinobacteria*, respectively. Thus, it appears that our new set of feature vectors loosely correspond to three taxa at the phylum level.

If the number of feature vectors in the basis set is increased, the clusters that corresponded to individual genera may be split into smaller subgroups.

Figure 8:
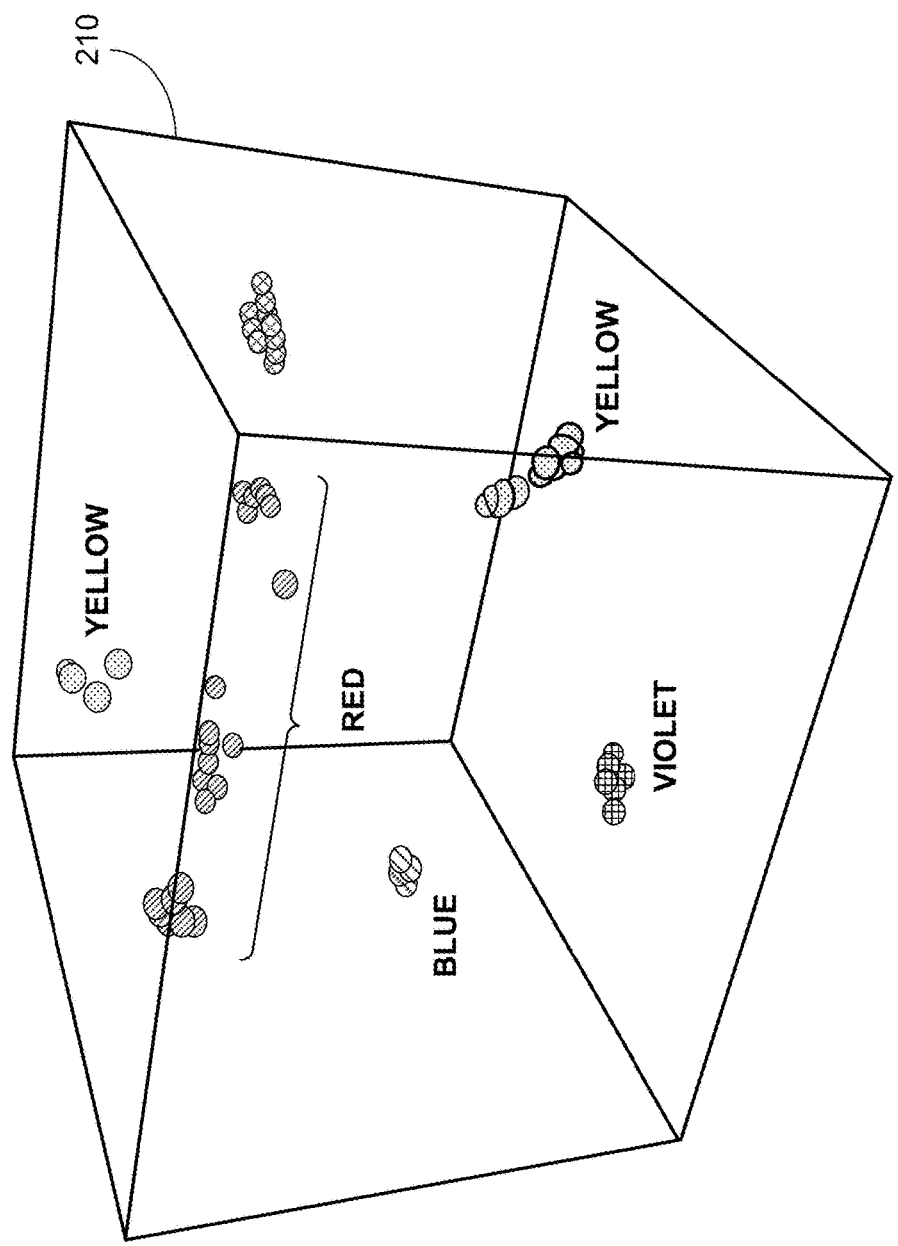

Referring to FIG. 8, a graph 210 shows the clustering of the samples that is achieved by generating a set of feature vectors with k=7 elements in the basis set. As shown in the graph 210, by increasing the number of feature vectors, we further divide the collection of sequences. For instance, *Burkholderia* samples (shown in red) that were deemed similar in less-detailed feature spaces have now been separated by this new set of basis vectors.

Figure 9:
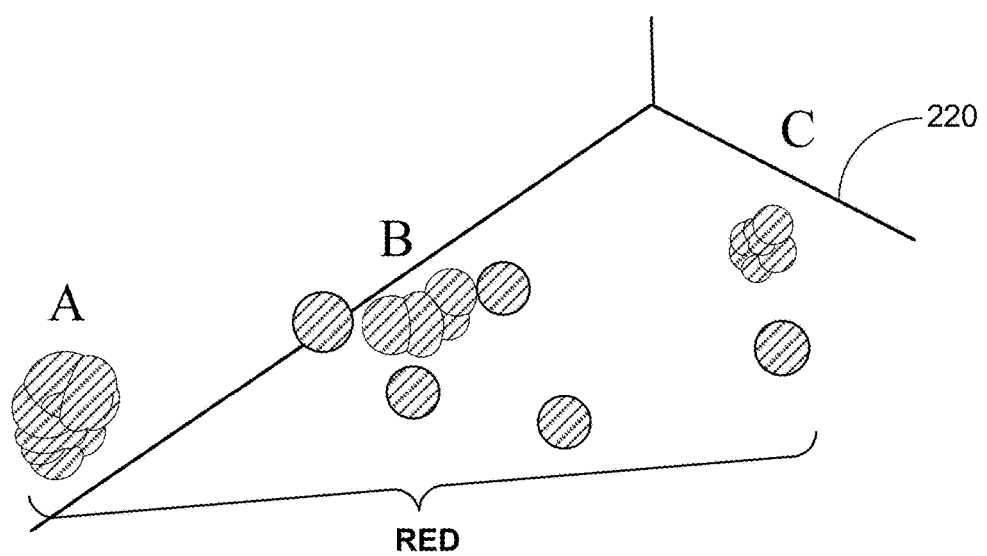

Referring to FIG. 9, a graph 220 shows an enlarged version of the cluster shown in red for the *Burkholderia* samples. There appears to be three distinct clusters (labeled A, B, and C) within this genus. Inspecting the three clusters, we find that these groupings are consistent with an earlier study that constructed a phylogenetic tree for the entire *Burkholderia* genus using the Jukes-Cantor model to measure variations in the recA gene. The results of FIGS. 7-9 show that the latent semantic analysis based method works well in differentiating between organisms at varying levels of evolutionary similarity, especially when there is a rough estimate of how many groups into which to partition the data. This approach can be used to construct a phylogenetic tree.

Figure 10:
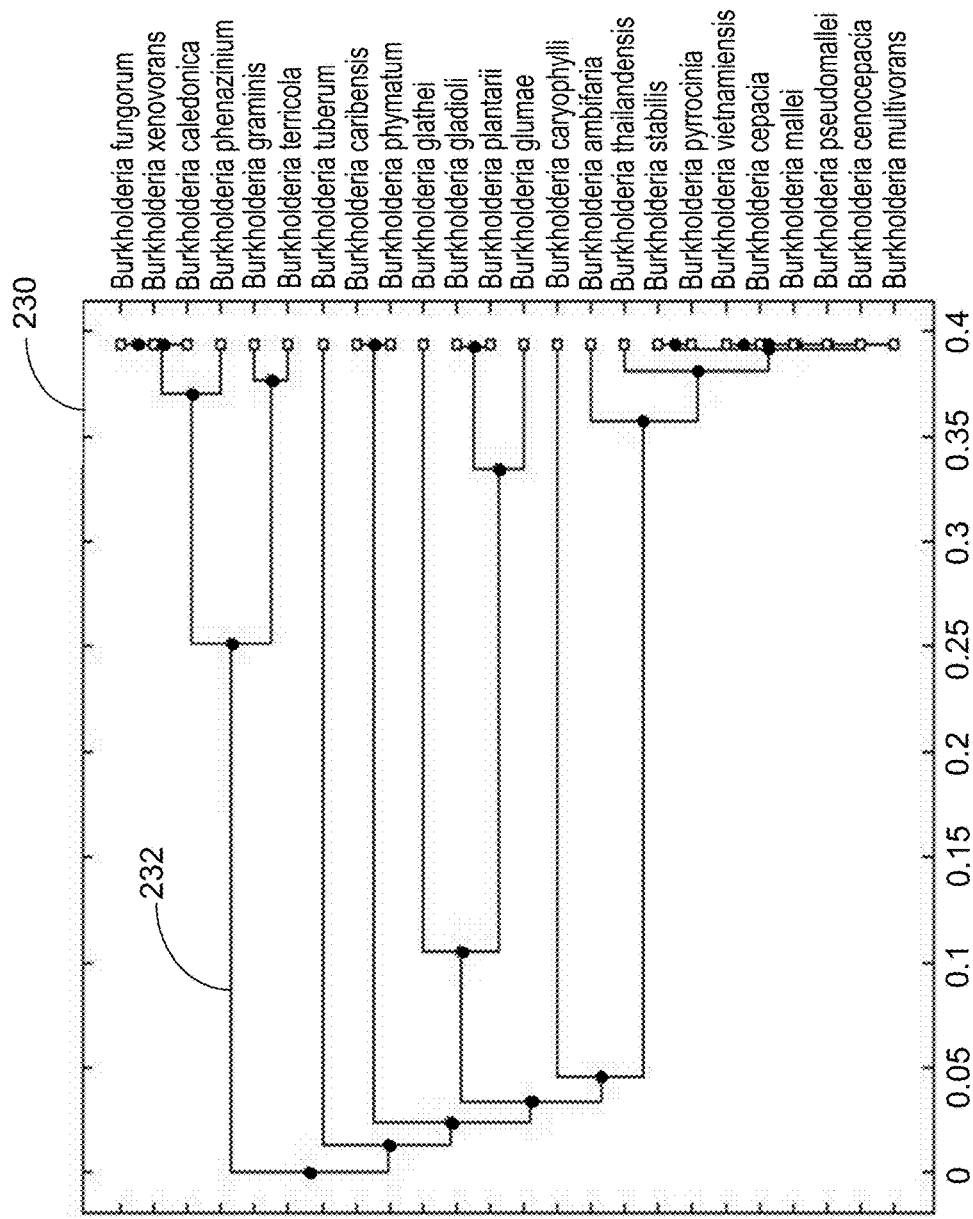

Referring to FIG. 10, a graph 230 shows a phylogenetic tree 232 constructed for the set of *Burkholderia* species that were analyzed in FIG. 5 by correlating the encoding vectors used to represent sequences in an LSA-NMF feature space. In general, the latent semantic analysis based method performs well and has captured the overall structure of the genus. The tree was constructed using 5 feature vectors. The lower portion of the tree 232 shows that species such as *Burkholderia cepacia* and *Burkholderia vietnamiensis* appear misleadingly similar despite the fact that they can be separated. This issue may be resolved by constructing the tree using a larger number of feature vectors.

Consider that the genus of *Burkholderia* contains a large number of pathogenic species, many of which are antibiotic resistant and are considered to be especially dangerous. Some of the more hazardous species are feared as potential biological warfare agents and must be handled with extreme caution. The lists of species within clusters A and C from FIG. 9 indicate that some clusters correspond to species associated with high risk factors, while some clusters correspond to species associated with low risk factors.

Table 1 below shows the risk factor associated with each of the species found in *Burkholderia* cluster A of FIG. 9. Table 2 below shows the risk factor associated with each of the species found in *Burkholderia* cluster C of FIG. 9. These risk factors are taken from the Technical Rules for Biological Agents (TRBA) from the German Federal Institute for Occupational Safety and Health (BAuA), and the levels indicate the risk of infection for an extensive list of species. On the BAuA's scale, a risk factor of 1 denotes an agent with a relatively low risk of infection, whereas agents having risk factors of 2 or higher are particularly virulent. Tables 1 and 2 show that cluster C is, in general, more dangerous than cluster A.

TABLE 1

*Burkholderia* cluster A with risk scores

| Genus | Species | Risk Score |
|---|---|---|
| *Burkholderia* | *Burkholderia bryophila* | 1 |
| *Burkholderia* | *Burkholderia caledonica* | 1 |
| *Burkholderia* | *Burkholderia caribensis* | 1 |
| *Burkholderia* | *Burkholderia ferrariae* | 1 |
| *Burkholderia* | *Burkholderia fungorum* | 1 |
| *Burkholderia* | *Burkholderia ginsengisoli* | 1 |
| *Burkholderia* | *Burkholderia graminis* | 1 |
| *Burkholderia* | *Burkholderia heleia* | ? |
| *Burkholderia* | *Burkholderia hospita* | 1 |
| *Burkholderia* | *Burkholderia kururiensis* | 1 |
| *Burkholderia* | *Burkholderia megapolitana* | 1 |

TABLE 1-continued

Burkholderia cluster A with risk scores

| Genus | Species | Risk Score |
|---|---|---|
| Burkholderia | Burkholderia mimosarum | 1 |
| Burkholderia | Burkholderia nodosa | 1 |
| Burkholderia | Burkholderia phenazinium | 1 |
| Burkholderia | Burkholderia phenoliruptrix | 1 |
| Burkholderia | Burkholderia phymatum | 1 |
| Burkholderia | Burkholderia phytofirmans | 1 |
| Burkholderia | Burkholderia sabiae | ? |
| Burkholderia | Burkholderia sacchari | 1 |
| Burkholderia | Burkholderia sartisoli | 1 |
| Burkholderia | Burkholderia sediminicola | 1 |
| Burkholderia | Burkholderia silvatlantica | 1 |
| Burkholderia | Burkholderia terrae | 1 |
| Burkholderia | Burkholderia terricola | 1 |
| Burkholderia | Burkholderia tropica | 1 |
| Burkholderia | Burkholderia tuberum | 1 |
| Burkholderia | Burkholderia unamae | 1 |
| Burkholderia | Burkholderia xenovorans | 1 |

TABLE 2

Burkholderia cluster C with risk scores

| Genus | Species | Risk Score |
|---|---|---|
| Burkholderia | Burkholderia ambifaria | 2 |
| Burkholderia | Burkholderia arboris | 2 |
| Burkholderia | Burkholderia cenocepacia | 2 |
| Burkholderia | Burkholderia cepacia | 2 |
| Burkholderia | Burkholderia cocovenenans | ? |
| Burkholderia | Burkholderia diffusa | 2 |
| Burkholderia | Burkholderia gladioli | ? |
| Burkholderia | Burkholderia glumae | 1 |
| Burkholderia | Burkholderia lata | ? |
| Burkholderia | Burkholderia latens | 2 |
| Burkholderia | Burkholderia mallei | 3 |
| Burkholderia | Burkholderia metallica | 2 |
| Burkholderia | Burkholderia multivorans | 2 |
| Burkholderia | Burkholderia oklahomensis | 2 |
| Burkholderia | Burkholderia plantarii | 1 |
| Burkholderia | Burkholderia pseudomallei | 3 |
| Burkholderia | Burkholderia pyrrocinia | 1 |
| Burkholderia | Burkholderia seminalis | 2 |
| Burkholderia | Burkholderia stabilis | 2 |
| Burkholderia | Burkholderia thailandensis | 1 |
| Burkholderia | Burkholderia ubonensis | 1 |
| Burkholderia | Burkholderia vandii | ? |
| Burkholderia | Burkholderia vietnamiensis | 2 |

Figure 11:
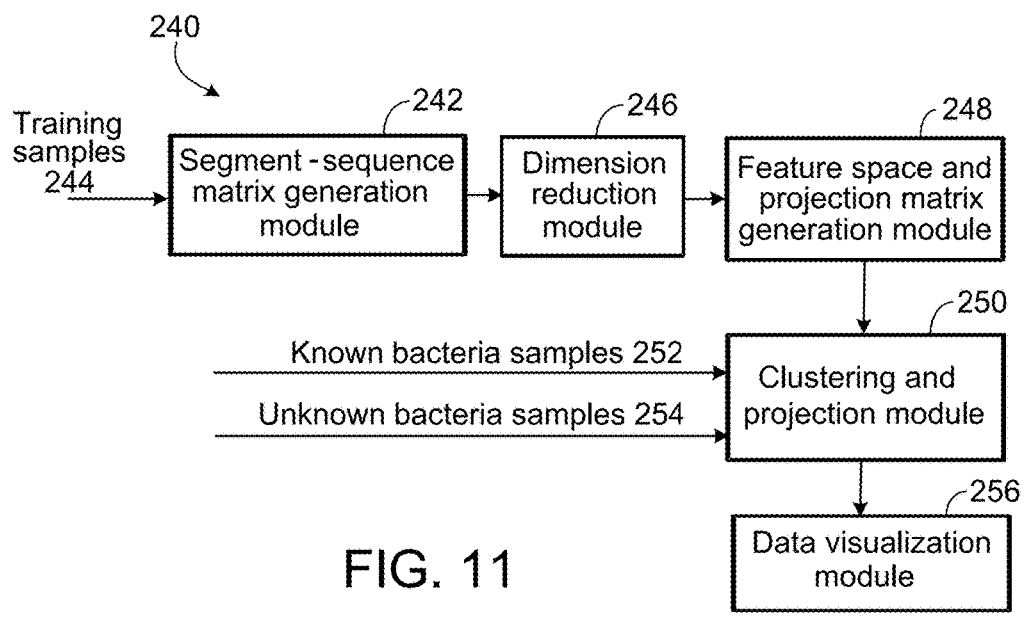
FIG. 11 is a block diagram of an exemplary system that use latent semantic analysis for classifying unknown samples.

Referring to FIG. 11, a system 240 can be used to classify an unknown sample and estimate the unknown sample's risk as an infectious agent. The system 240 includes a segment-sequence matrix generation module 242 that receives a set of training DNA sequences 244 that includes sample sequences from the various bacteria having known risk factors. The module 242 generates a corresponding segment-sequence matrix. A dimension reduction module 246 applies dimension reduction to the segment-sequence matrix to determine a set of basis vectors or feature vectors. For example, the dimension reduction module 246 can use non-negative matrix factorization or singular value decomposition algorithm. Using the basis vectors, a feature space and projection matrix generation module 248 defines a feature space. A projection matrix is generated to enable an unknown sample to be projected into the feature space.

A clustering and projection module 250 receives information about the feature space and the projection matrix from the feature space and projection matrix generation module 248. The clustering and projection module 250 receives a first set of known bacterial samples 252, and a second set of unknown bacteria samples 254. The clustering and projection module 250 projects the first set of known samples into the feature space and clusters the projected samples in the feature space. Some of the clusters are primarily associated with the bacteria having low risk factors, and some of the clusters are primarily associated with the bacteria having high risk factors.

The clustering and projection module 250 projects the second set of unknown samples into the feature space and clusters the unknown samples along with the known samples. A data visualization module 256 highlights the unknown samples that are grouped with the clusters associated with bacteria having high risk factors.

The system 240 identifies a set of basis vectors that have been trained to recognize a set of features that are indicative of harmful agents. The system 240 queries or projects profile vectors of new sequences into a predetermined feature space and avoids recalculating the non-negative matrix factorization for every test.

Identification and Removal of Host DNA Fragments from Metagenomics Datasets

The following describes the principles of the system 120 in FIG. 2 in more detail. LSA-NMF can be used to construct high-dimensional feature spaces in which the dimensions indicate the presence of specific biological "feature" present in a genomic sequence. Predefined feature spaces can be used to filter out unwanted samples of DNA.

An example where such a "DNA filter" can be useful is in the field of metagenomics. Metagenomics is an area of study that focuses on sequencing genetic material that has been taken from environment samples. In some examples, sequencing an organism begins with the isolation and amplification of the organism's cells. However, for a large number of organisms, the cells cannot be cultured in isolation. Metagenomic studies do not attempt to remove an organism from its natural environment, but instead, sequence it directly along with anything else that is in the set of samples collected from the environment. Thus, metagenomic studies may involve identifying and assembling genomic sequences from a microbial community containing a diverse mixture of organisms.

A common problem in metagenomic studies is that many of the microbial cells to be analyzed are found inside other living organisms. When a sample is taken from, for example, the gut of an animal or a human, the sample will also contain DNA from the host organism. The host may have a large and complex genome that when sequenced may contain portions that look similar to the bacterial samples to be analyzed. A large percentage of the sequenced data may belong to the host.

It is useful to be able to remove at least a portion of the host DNA from a sequenced metagenomic sample. We can filter out unwanted DNA fragments by constructing feature spaces that have been trained to distinguish the host DNA from the bacterial samples that we wish to keep.

We can generate a metagenomic dataset synthetically. The following describes an example in which the results of sequencing a gut sample from *Mus musculus*, the common house mouse, is simulated. The bacteria in this example are divided into three primary phyla: *Bacteroidetes, Firmicutes*, and *Proteobacteria*. In the experiment, the two most dominant genera from each phylum were included in the mixture. These genera are *Alistipes* and *Bacteroides* from *Bacteroidetes*; *Bacillus* and *Clostridium* from *Firmicutes*; and *Acinetobacter* and *Enterobacter* from *Proteobacteria*.

The complete genomes for each of these bacteria and all chromosomes from *Mus musculus* were collected and randomly sampled to generate 1 kbp fragments, simulating shotgun sequencing. The fragments from each organism were combined to form a collection of nearly 10,000 fragments, made up of approximately 90% mouse DNA and 10% bacterial DNA. The number of samples taken from each group of bacteria was chosen based on their average relative abundance amounts. For the mouse, an equal number of samples were taken from each chromosome.

Table 3 lists the amount of samples from each major group of organisms. Table 4 lists the amount of samples from various bacterial genera.

TABLE 3

Amount of samples from each major group of organisms

| Group | Sample Count | % of Total |
|---|---|---|
| Host (*Mus musculus*) | 8,771 | 89.74% |
| Bacteroidetes | 693 | 7.09% |
| Firmicutes | 260 | 2.66% |
| Proteobacteria | 50 | 0.51% |

TABLE 4

Amount of samples from bacterial genus

| Phylum | Genus | Sample Count | % of Bacteria Total |
|---|---|---|---|
| Bacteroidetes | *Alistipes* | 343 | 34.20% |
| Bacteroidetes | *Bacteroides* | 350 | 34.90% |
| Firmicutes | *Bacillus* | 65 | 6.48% |
| Firmicutes | *Clostridium* | 195 | 19.44% |
| Proteobacteria | *Acinetobacter* | 25 | 2.49% |
| Proteobacteria | *Enterobacter* | 25 | 2.49% |

After the synthetic dataset is assembled, we can design a filter. We assume that, whether in whole or in part, we have access to the host organism's genome. We also assume that we know of and have access to genomic sequences for at least one of the bacteria in the microbiome. These sequences will be used to construct the feature spaces for determining which fragments to keep and which to discard.

As described above, sequences can be clustered in feature spaces that are obtained by performing non-negative matrix factorization on the entire collection of sequence profiles. Because a metagenomic dataset may contain millions of sequences, it is preferable to avoid this computation-intensive step. A set of training data can be used to define a feature space, and a projection matrix can be used to map k-mer-sequence vectors into this space.

We define a feature space that can be used to differentiate between host fragments and samples that belong to the microbial cell. We perform non-negative matrix factorization on a small set of known samples taken from the host's DNA and the bacteria that is assumed to be the mixture. In this example, we trained an initial feature space using a collection of just under 1,000 sequences, half of which were taken from *Mus musculus*. The other half were obtained by randomly sampling *Bacteroides fragilis*, which is an organism from the most dominant genus in the mouse's gut microbiome.

These sequences were profiled as k-mer frequency vectors using a k-mer size of 7, and the results were compiled into a k-mer-sequence matrix, $X_K$, representing the profiles of the known set. We apply tf-idf weighting followed by the same standard, non-negative least squares implementation of non-negative matrix factorization on $X_K$ to obtain the approximation $$X_K \approx A_K Y_K.$$  (Equ. 15)

In anticipation of a diverse set of samples in the mixture, we chose to use k=25 basis vectors for the factorization. The matrix $A_K$ includes the set of basis vectors which define a high-dimensional feature space, and the matrix $Y_K$ is a collection of encodings that can be used to reconstruct the original set of vectors using this basis set. The following describes a method of projecting new samples into a feature space that has been obtained through non-negative matrix factorization. A user can project new samples into the feature space and determine whether or not the new samples appear to be from the mouse genome.

Given an unknown sample x, its approximation in the feature space defined by the set of basis vectors A can be written as $$x \approx Ay,$$  (Equ. 16)

in which y is the encoding used to reconstruct x using the elements of A. The vector y is a k-dimensional profile (a "feature profile") that characterizes x, so it is useful to have a way to transform x into y. Solving for y in Equation 16, we obtain the projection matrix B as follows:

$$x \approx Ay$$

$$A^T x \approx (A^T A) y$$

$$(A^T A)^{-1} A^T x \approx (A^T A)^{-1} (A^T A) y$$

$$(A^T A)^{-1} (A^T x) \approx y$$

$$(A^T A)^{-1} A^T x \triangleq Bx \approx y$$  (Equ. 17)

Now, given an unknown sample x, we can perform a simple matrix multiplication to project x's k-mer-sequence vector into a predetermined feature space. For example, we can project an item into the feature space defined by $A_K$ using the projection matrix $$B = (A^T A_K)^{-1} A_K^T$$

Once samples are in the feature space, similar objects can be identified, including determining whether or not a sequence appears to have been taken from the host's genome. Having known sequences from both the host and the microbial colony, there are a number of ways in which the feature space can be partitioned in order to identify samples that should be removed. One approach is to project and cluster known fragments along with the set of unknown samples. By noting how the known sequences cluster, it is possible to determine which groups of sequences should be filtered out. In some examples, the system 120 uses k-means clustering to group elements in the feature space. Other ways of clustering the elements can also be used. A process for filtering a host's DNA from a sequenced metagenomic sample can include the following steps:

(1) Construct a projection matrix B using known samples.
(2) Project known and unknown samples into the feature space using projection matrix B.
(3) Cluster the feature profiles.
(4) Eliminate groups containing known-host samples.
(5) Repeat steps 1-4 as needed, using same or different known samples.

The system 120 was used to construct a k-mer-sequence matrix using a set of roughly 1,000 known fragments randomly chosen from the host's genome and the microbial community. The matrix was used to train an initial feature space with corresponding projection matrix $B_0$. A collection of 200 known-host fragments, 200 known-bacterial fragments, and the entire set of approximately 10,000 unknown samples were projected into the feature space defined by $B_0$.

In this example, the 200 known-host and known-bacterial fragments were different than those used to train $B_0$.

Once in the feature space, the projected samples were clustered into 20 groups using k-means clustering to identify sequences having similar feature profiles. The compositions of these clusters are presented in Table 5, which shows round 1 clustering of mouse metagenomic data. There are columns denoting the clustering of known and unknown samples. The "Known" columns provide information on which clusters are primarily associated with host sequences, and which clusters are primarily associated with bacteria sequences. This information can be used to determine whether or not to remove the cluster. For example, clusters 1-3, 5-9, 11, 12, and 14-17 are primarily associated with host sequences. This means that among the unknown samples, the samples that are grouped with clusters 1-3, 5-9, 11, 12, and 14-17 can be removed because they are likely sequences from the host.

A set of predetermined criteria may be set for the removal of host samples. For example, a cluster can be considered to be associated with the host if the cluster includes a large majority of known-host samples, in which the percentage is greater than a preset value. In addition, a cluster can be a target for removal if the known bacteria samples is not more than a preset maximum number. For example, a cluster can be considered to be associated with the host if the number of the known host samples is more than four-times the number of the known bacteria samples, and the cluster has not more than 10 known bacteria samples.

For example, in clusters 1-3, 5-9, 11, 12, and 14-17, the number of known host samples is greater than 4 times the number of known bacteria samples, and the number of known bacteria samples is not more than 10. Thus, clusters 1-3, 5-9, 11, 12, and 14-17 are considered to be associated with the host. Unknown samples grouped in clusters 1-3, 5-9, 11, 12, and 14-17 are predicted to be associated with the host and can be removed. The removal predictions are shown in the right-most column.

TABLE 5

Round 1 clustering of mouse metagenomic data.

| | Known Samples | | Unknown Samples | | |
|---|---|---|---|---|---|
| Cluster | Host | Bacteria | Host | Bacteria | Remove? |
| 1 | 45 | 0 | 2060 | 0 | Y |
| 2 | 2 | 0 | 15 | 0 | Y |
| 3 | 12 | 0 | 537 | 0 | Y |
| 4 | 0 | 99 | 5 | 280 | N |
| 5 | 14 | 1 | 553 | 0 | Y |
| 6 | 3 | 0 | 111 | 0 | Y |
| 7 | 7 | 0 | 257 | 0 | Y |
| 8 | 10 | 0 | 192 | 0 | Y |
| 9 | 2 | 0 | 78 | 0 | Y |
| 10 | 0 | 68 | 2 | 243 | N |
| 11 | 1 | 0 | 54 | 0 | Y |
| 12 | 6 | 0 | 280 | 0 | Y |
| 13 | 31 | 17 | 1182 | 145 | N |
| 14 | 8 | 0 | 273 | 0 | Y |
| 15 | 3 | 0 | 209 | 0 | Y |
| 16 | 5 | 0 | 152 | 0 | Y |
| 17 | 51 | 9 | 2720 | 0 | Y |
| 18 | 0 | 6 | 22 | 168 | N |
| 19 | 0 | 0 | 6 | 167 | N |
| 20 | 0 | 0 | 64 | 0 | N |

Table 5 shows the number of unknown samples that are removed in this round of filtering. In the first round of clustering and filtering, 7,491 of the unknown mouse fragments were removed without removing any unknown bacterial samples. In just one pass of the filter, over 85 percent of the host DNA was removed, leaving 1,280 samples. In this example, some clusters have 0 known host and bacterial samples. It is possible that by using a larger set of known samples, additional clusters may be determined to be associated with the host, and thus more samples may be removed. If the maximum number of known bacterial samples is increased, it may be possible to eliminated additional host DNA. For example, if cluster 13 is considered to be associated with the host, and the unknown samples grouped with cluster 13 are removed, that will result in leaving 98 samples or 1.1% of the host DNA while retaining 85% of the bacterial samples.

After the first round of clustering and filtering, there are three options: (1) decide that this is good enough and stop; (2) repeat the same set of steps, but using a different projection matrix; or (3) place everything that remains along with the known samples back into the feature space and repeat the clustering and removal process. In this example, choosing option (3) and repeating the clustering with the same set of known samples, the results of round 2 filtering are presented in Table 6.

TABLE 6

Round 2 clustering of mouse metagenomics data

| | Known Samples | | Unknown Samples | | |
|---|---|---|---|---|---|
| Cluster | Host | Bacteria | Host | Bacteria | Remove? |
| 1 | 78 | 1 | 0 | 0 | Y |
| 2 | 1 | 0 | 0 | 0 | Y |
| 3 | 7 | 0 | 29 | 0 | Y |
| 4 | 0 | 0 | 0 | 135 | N |
| 5 | 10 | 0 | 6 | 0 | Y |
| 6 | 16 | 4 | 75 | 0 | Y |
| 7 | 0 | 34 | 0 | 226 | N |
| 8 | 0 | 84 | 9 | 34 | N |
| 9 | 1 | 54 | 2 | 203 | N |
| 10 | 0 | 0 | 63 | 0 | N |
| 11 | 1 | 0 | 0 | 0 | N |
| 12 | 3 | 4 | 32 | 94 | N |
| 13 | 9 | 1 | 294 | 2 | Y |
| 14 | 0 | 1 | 0 | 141 | N |
| 15 | 10 | 7 | 273 | 43 | N |
| 16 | 0 | 2 | 0 | 117 | N |
| 17 | 33 | 8 | 470 | 7 | Y |
| 18 | 4 | 0 | 24 | 0 | Y |
| 19 | 10 | 0 | 0 | 0 | Y |
| 20 | 17 | 0 | 4 | 0 | Y |

In the second round, another 902 host fragments have been eliminated, with the loss of 9 bacterial fragments. After round 2, there are 378 samples or 4% of the original amount of host DNA, and over 99% of the original 1,003 bacterial samples remaining. Continuing to filter the samples in this manner for a few more rounds, the results are shown in Table 7. In this table, a "*" next to the round number indicates that a projection matrix, trained on a new group of host and bacterial samples was computed prior to this stage. With each of these rounds, a new set of known samples was chosen to be clustered in this and subsequent rounds.

TABLE 7

Several rounds of filtering mouse metagenomics data

| Round | Remaining Host Samples | Remaining Host % | Remaining Bacterial Samples | Remaining Bacterial % |
|---|---|---|---|---|
| (Start) | 8771 | 100.0 | 1003 | 100 |
| 1* | 1280 | 14.59 | 1003 | 100 |
| 2 | 378 | 4.30 | 994 | 99.1 |
| 3 | 235 | 2.68 | 985 | 98.2 |

TABLE 7-continued

Several rounds of filtering mouse metagenomics data

| Round | Remaining Host Samples | Remaining Host % | Remaining Bacterial Samples | Remaining Bacterial % |
|---|---|---|---|---|
| 4* | 68 | 0.775 | 974 | 97.1 |
| 5 | 65 | 0.741 | 973 | 97.0 |

Figure 12:
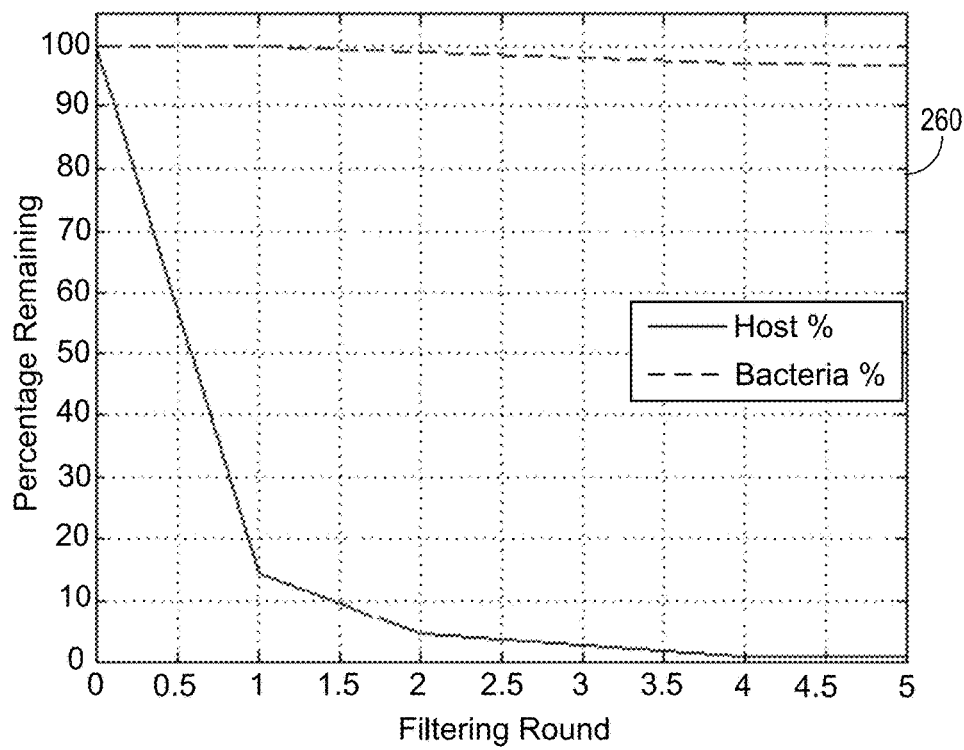

FIG. 12 is a graph 260 that shows the number of host and bacterial samples remaining after each round of filtering. If the filtering process is stopping after either round 4 or 5, the final percentage of host samples remaining is less than one percent of its starting amount, while preserving about ninety-seven percent of the original unclassified bacterial samples. In addition, throughout this process, the composition of the mixture went from 90% host DNA down to about 6% in the final set.

A process for filtering host DNA from a sequenced metagenomics dataset has been described. The amount of host DNA in the mixture can be reduced significantly. If the criteria is selected such that sacrificing a larger number of bacterial samples is allowed, it may be possible to eliminate more host fragments.

There are a number of ways to partition a feature space in order to recognize and eliminate fragments which appear to be very similar to the host's DNA. In some examples, k-means clustering can be used to accomplish this partitioning, but other clustering methods can also be used.

Under LSA-NMF, a sample either exhibits a particular feature or not. In some examples, the strength with which a sample associates with a given feature vector can be used in the clustering process. A crude method of clustering can be achieved by noting the feature vector with the greatest contribution for a collection of samples, and clustering items by their strongest feature. However, this method may be too crude for many applications. This process can be modified as follows. By observing the contributions of each feature vector in the reconstruction of a sequence, it appears that a few dimensions have very large components, and the rest die off rather quickly.

Figure 13:
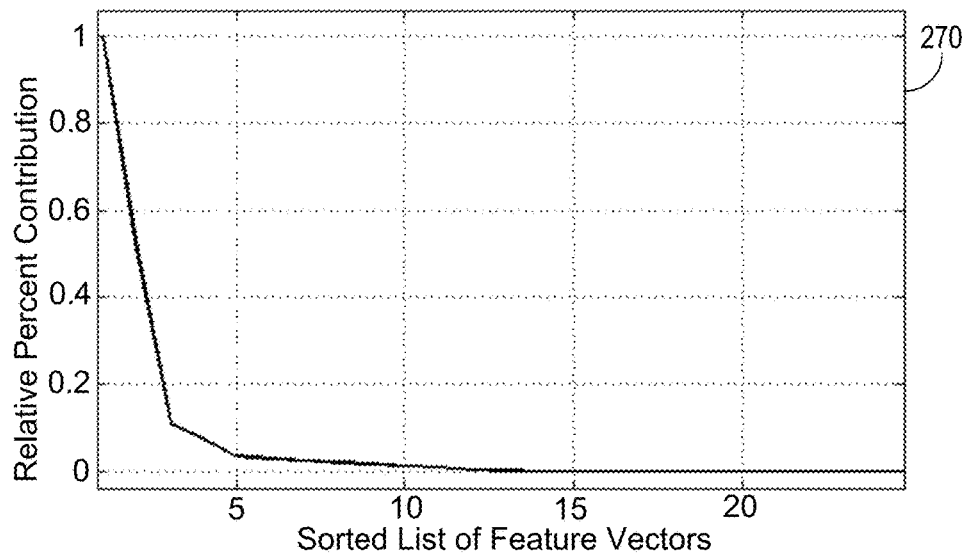

FIG. 13 is a graph 270 that shows the average level of contribution for a collection of 500 feature profiles of length 25 that have been sorted by their magnitude. The graph 270 shows that a large percentage of the sequences are almost completely characterized by five or fewer components. An efficient way of clustering samples is to express sequences as a combination of features. Similar to the way that a semantic topic may be a combination of multiple subtopics in the realm of information retrieval, a sequence can be expressed as a combination of a set of biological features. As a result, feature profiles can serve as a type of hyper-spectral coloring that can be used to distinguish between highly similar sequences with low computational overhead.

Using LSA-NMF to Design Microarray Probes

In some implementations, latent semantic analysis by non-negative matrix factorization can be used to design microarray probes. As described above, LSA-NMF can be used to construct high-dimensional feature spaces in which genomic sequences are classified into various clusters. The feature vectors can be useful in the design of DNA microarray probes.

A DNA microarray uses a large collection of short DNA probes to detect the presence of specific sequences in a mixture. The probes are short pieces of complementary DNA that bind or hybridize to a matching sequence if it is found in the mixture.

In some examples, DNA microarrays can be used for gene expression profiling. When a gene is transcribed or copied by the enzymes inside a cell, a piece of messenger RNA (mRNA) is created. The mRNA includes a set of instructions that directs the cell to perform some function. By convention, when a gene is transcribed into mRNA, the gene is said to be expressed. If a particular gene is used to perform a routine task, it may be expressed very frequently or in large amounts. If the gene is used only under special conditions, it may have a relatively low rate of expression.

A set of probes can be designed for use in a DNA microarray to measure the expression of an entire collection of genes simultaneously. By noting when and how many genes are expressed, an organism's "gene expression profile" can be observed. This profile differs between individuals and even in different parts of the body. By comparing a set of expression profiles, it may be possible to obtain information that can be used for a variety of purposes, such as predicting a gene's function or evaluating the status of a disease.

In addition to gene expression profiling, DNA microarrays are also frequently used to detect pathogenic species in an environmental sample. By designing a set of probes that indicate the presence of certain organisms, microarrays can be used to diagnose infectious diseases or monitor the safety of food, water, and air. The role that microarray probes play in each of these applications is similar to the use of feature vectors to identify and differentiate between organisms. The following describes a novel method for designing microarray probes by reverse engineering the feature vectors in an LSA-NMF space.

The feature vectors or dimensions of an LSA-NMF space can be regarded as corresponding to biological features that are exhibited by a genomic sequence. In the examples shown in FIGS. 4-10, the features are indicators of the genus or some other taxonomic group to which the organism belonged. The presence of a feature is signaled by the presence of a set of one or more k-mers in a k-mer-sequence vector. By investigating which k-mers are found in these sets, it is possible to identify a collection of distinct k-mers that together can be used to indicate a biological feature.

A process for determining which k-mers are mapped to each feature vector is described below. Individual k-mers can be projected into a predetermined space, and the strength to which the k-mers associate with a particular feature can be recorded. In an information retrieval system, this method is the equivalent of querying a semantic space with individual words and noting how strongly they indicate a semantic group. In effect, this process identifies potential keywords or distinct k-mers whose presence is indicative of a semantic group or biological feature.

By varying the choice of k-mer size and the number of dimensions in the factorizations, it may be possible to devise a method for establishing collections of variable-length oligonucleotides that can be used to design efficient sets of microarray probes. Using a feature space of lower dimensions results in a less-specific partitioning of the collection of elements. In detecting the presence of a distinct organism, a series of feature spaces can be used to search for a species at varying levels of precision.

The 5-genus dataset described above is used to evaluate the process for designing microarray probes. A metagenomic dataset can contain a more diverse mixture of species. By training a feature space of five dimensions on this collection of sequences, the elements in the resulting basis set roughly correspond to the five genera found in the mixture.

Figure 14:
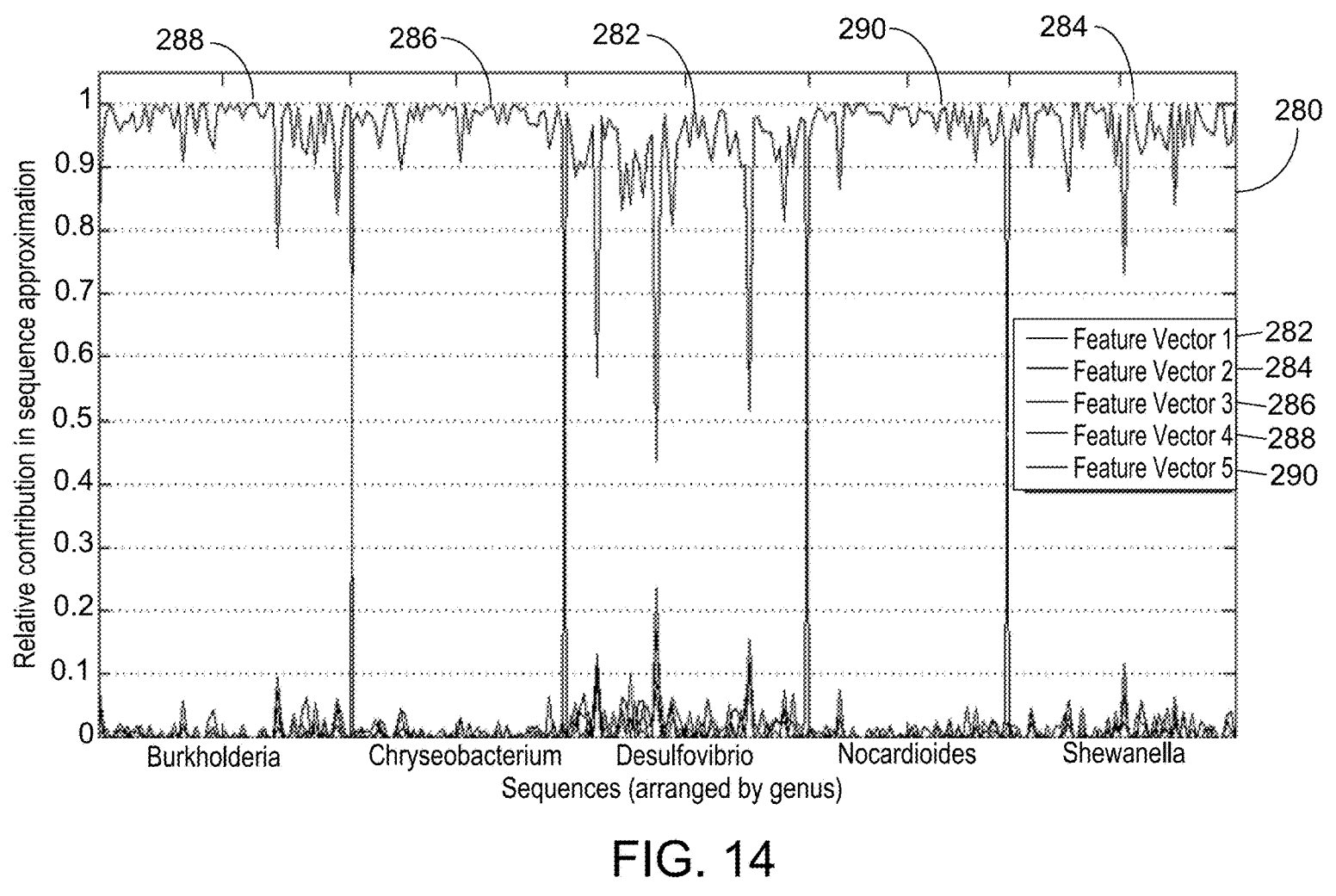

Referring to FIG. 14, a graph 280 shows the amount of contribution for each of the five feature vectors in reconstructing each sequence in the collection. A value of 1.0 in this figure means that a sample is best approximated using only one of the elements from the basis set. For example, lines 282, 284, 286, 288, and 290 represent the amount of contribution for feature vectors 1, 2, 3, 4, and 5, respectively in reconstructing each sequence in the collection.

FIG. 14 shows that the set of feature vectors can be used to predict the genus of a sample. When a basis vector is used in the reconstruction or approximation of a sample, it indicates that the sample's DNA sequence contains some distinct collection of k-mers. As a result, by determining which k-mers are in the collections, the k-mers can be used to construct a set of microarray probes that can detect this same set of features.

To determine which oligos best represent a particular feature (considered to be "keywords"), individual k-mers can be projected into the feature space, and how well they associate with the corresponding basis vector can be recorded. This is equivalent to observing the columns of the projection matrix $B=(A^T A)^{-1} A^T$ for a basis set A. In this matrix, the magnitude of each element $B_{i,j}$ provides an indication of the strength with which the $j^{th}$ k-mer implies the $i^{th}$ feature.

Figure 15A:
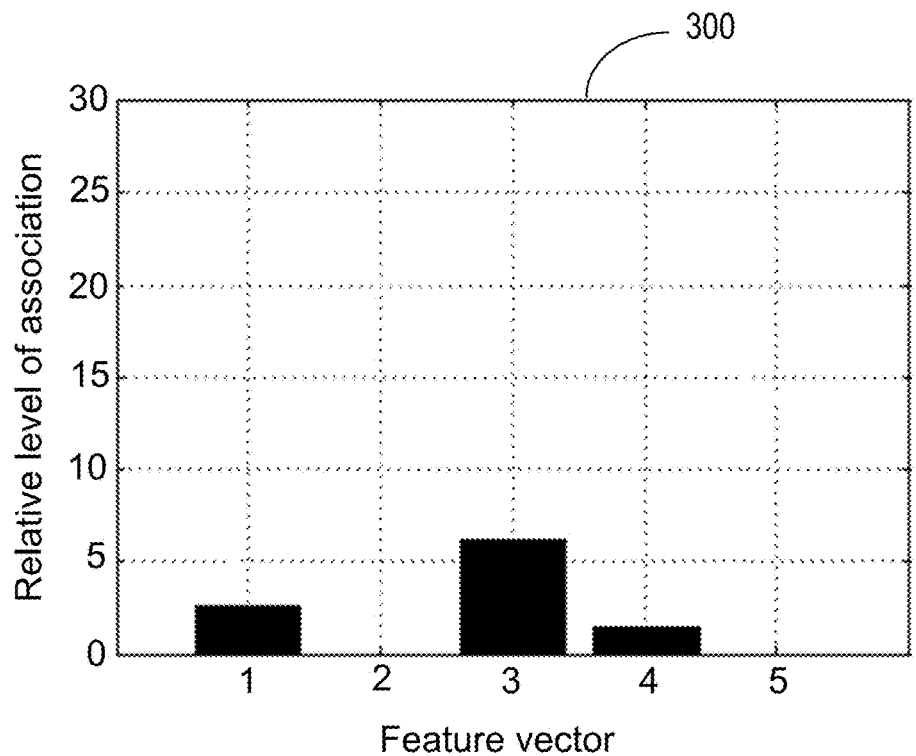
Figure 15B:
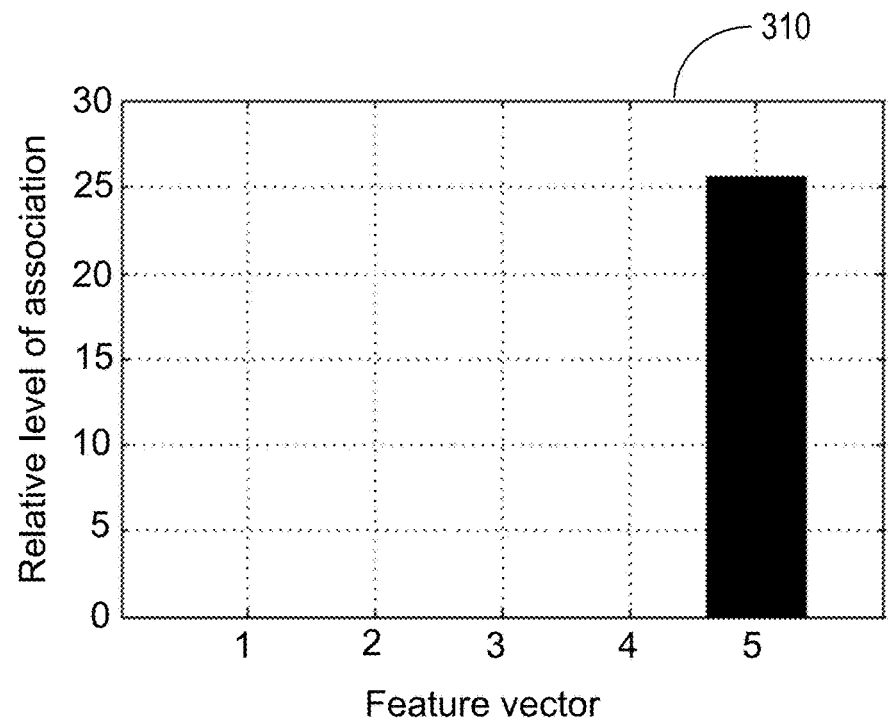

FIG. 15A is a graph 300 that shows the relative levels of association for the k-mer ctgtta with each of the five basis vectors in FIG. 14. FIG. 15B is a graph 310 that shows the relative levels of association for the k-mer tgggtc with each of the five basis vectors in FIG. 14. In FIGS. 15A and 15B, the "relative level of association" indicates the amount that each feature vector contributes in the approximation of the k-mer, relative to the average contribution amount (the mean of B). This measure can be used as an indication of the k-mer's association with each feature. The graph 300 of FIG. 15A shows that the segment ctgttat is a weak indicator of features 1, 3, and 4. The graph 310 of FIG. 15B shows that the segment tggggtc appears to be a clear indication of feature vector 5 and, thus, the genus *Nocardioides*.

Figure 16:
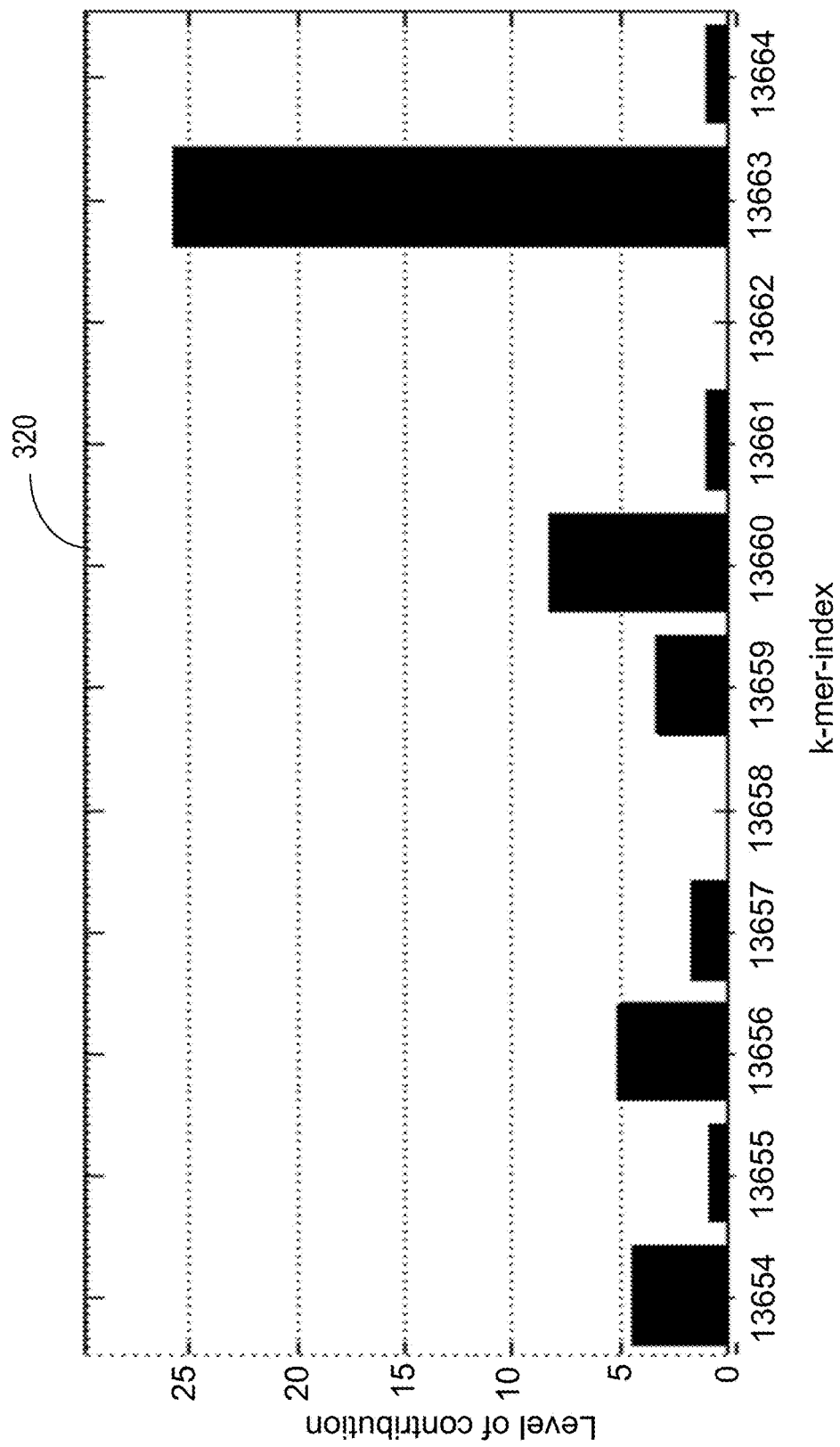

Referring to FIG. 16, a graph 320 shows the levels of association for feature vector 5 over a range of the 16,384 possible 7-mers. Shown in the right, index number 13,663 corresponds to the k-mer tggggtc, which as described above is a strong representative of the feature vector 5. The examples in FIGS. 15A, 15B, and 16 indicates that it is possible construct a set of microarray probes by finding the collection of k-mers with the highest levels of association for each of the features that corresponds to the genetic sequence to be detected. For example, a set of candidate microarray probes for *Nocardioides* is selected by sorting the list of k-mers by their level of association and picking the top five.

TABLE 8

Candidate probe oligos (* indicates the previous round was repeated with the reverse complement of the k-mer.)

| Rank | k-mer | Level of Assoc. | TP | FP | TN | FN |
|---|---|---|---|---|---|---|
| 1 | gacccca | 25 | 47 | 0 | 221 | 0 |
| 2 | tggggtc | 25 | 47 | 1 | 220 | 0 |
| 3 | agcaacg | 22 | 47 | 3 | 218 | 0 |
| 4 | cgttgct | 22 | 3 | 0 | 221 | 44 |
| 4* | agcaacg | 22 | 47 | 3 | 218 | 0 |
| 5 | gcatgcg | 21 | 46 | 0 | 221 | 1 |

Table 8 above shows the results of searching for each candidate oligo in the collection of 268 samples. The number of true positives (TP) indicates the number of the 47 possible *Nocardioides* species that contain the k-mer in question and thus should hybridize to the probe. The number of false positives (FP) indicates the number of species outside of *Nocardioides* that also contained the oligo. Table 8 shows that this collection of probes works well in detecting only the target sequences.

When constructing the k-mer-sequence vectors, the fact that DNA contains two complementary strands is taken into account by counting k-mers and their reverse complements when profiling the sequence. In Table 8, the 4-th probe cgttgct is the reverse complement of the probe that is useful. By using the probe's complement in row 4*, a much better performance is obtained, and the results are consistent with the rest of the table.

To detect sequences other than double-stranded genetic material, such as using RNA probes, profile sequences can be used without counting reverse complements as the sequence is profiled. Table 9 below shows results for analyzing the same k-mers using this method of profiling.

TABLE 9

Candidate probe oligos found by using alternative profiling method (without counting reverse complements in k-mer profile)

| Rank | k-mer | Level of Assoc. | TP | FP | TN | FN |
|---|---|---|---|---|---|---|
| 1 | cgcagat | 35 | 47 | 1 | 220 | 0 |
| 2 | cagcaac | 34 | 47 | 3 | 218 | 0 |
| 3 | ttgggcg | 34 | 47 | 3 | 218 | 0 |
| 4 | agcaacg | 34 | 47 | 3 | 218 | 0 |
| 5 | cgtcacg | 33 | 46 | 0 | 221 | 1 |

Table 9 shows that this approach yields similar results but with slightly higher levels of association. This may be due to not counting reverse complements in the profile, so there is a lower chance of two unrelated sequences containing the same k-mer. Despite using a different profiling scheme, both approaches produce similar sets of candidate oligos, with agcaacg being found in the top five for both.

The results from the two examples shown in Tables 8 and 9 enables identification of a unique set of k-mers that reliably detect the presence of the target collection of *Nocardioides* samples. By using a microarray that contains a combination of these probes, a high level of detection can be maintained while further reducing the small number of false positives.

The following describes an example in which the process of identifying microarray probes is applied to a larger dataset that contains a total of 750 16s sequences, in which 75 sequences are taken from each of the following, randomly selected genera: *Bacillus, Burkholderia, Corynebacterium, Enterococcus, Halomonas, Nocardia, Pseudomonas, Streptococcus*, and *Vibrio*. The process begins by training a projection matrix for this collection of sequences, using 10 feature vectors to define the LSA-NMF space.

Figure 17:
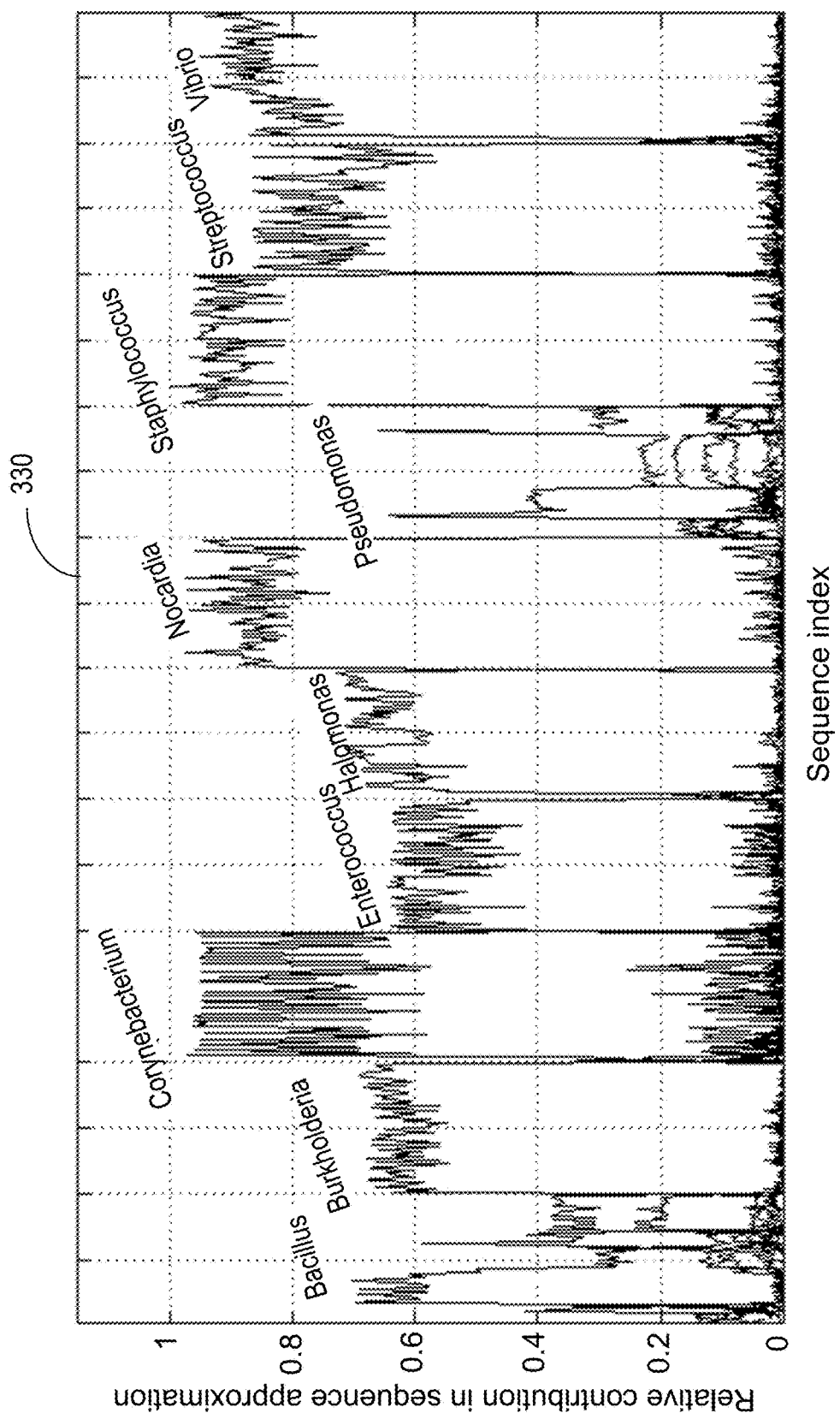

Referring to FIG. 17, a graph 330 shows which feature vectors are used in the approximation of each sample in the collection. The graph 330 shows that the feature vectors roughly correspond to the ten genera, though the correspondence is not perfect. The encodings corresponding to genera *Bacillus* and *Pseudomonas* are unpredictable and do not seem to associate well with any one particular feature vector.

This is consistent with biological research that indicates a high level of diversity in the 16S sequences for *Bacillus* and *Pseudomonas*. A number of species from *Psuedomonas* have even been relocated into other genera, such as *Burkholderia*.

The graph 330 in FIG. 17 indicates that it is possible select the oligos for the microarray probes by using feature vectors that best indicate each of the 20 species. Table 10 shows candidate probe oligos for *Streptococcus*.

TABLE 10

Candidate probe oligos for *Streptococcus*

| Rank | k-mer   | Level of Assoc. | TP | FP | TN  | FN |
|------|---------|-----------------|----|----|-----|----|
| 1    | ctgaagt | 37              | 64 | 1  | 674 | 11 |
| 2    | taggtcc | 35              | 73 | 1  | 674 | 2  |
| 3    | tcggtga | 35              | 68 | 86 | 589 | 7  |
| 4    | aagggac | 33              | 74 | 1  | 674 | 1  |
| 5    | aggtccc | 33              | 73 | 0  | 675 | 2  |
| 6    | gtgctag | 33              | 75 | 1  | 674 | 0  |
| 7    | aggtgtt | 33              | 74 | 2  | 673 | 1  |
| 8    | gttgtat | 33              | 71 | 0  | 675 | 4  |
| 9    | gtaggtc | 33              | 74 | 2  | 673 | 1  |
| 10   | ctttccg | 32              | 71 | 0  | 675 | 4  |

Table 10 shows the ten oligos having the highest levels of association for the *Streptococcus* feature vector. This set of probes reliably detects the presence of the target samples, while producing a low number of false positives. By requiring a combination of these k-mers, the likelihood of false positives can be further reduced.

The process for selecting candidate oligos for the probes uses a k-mer's "relative level of association" with each feature vector. The subset of oligos with the highest levels of association is chosen. A weighting can be applied to deemphasize k-mers that are highly associated with multiple features.

In a large, diverse dataset, it is possible that no oligo is highly representative of a feature. By increasing the k-mer size, the number of possible keywords that can be used to define a feature can be increased. By keeping track of the relative levels of association for a dataset, it is possible to determine whether or not the k-mer size should be increased. While 7-mers are used in the above example, larger probe sizes can be used to keep false positive rates low. By increasing the length of the probes, higher specificity can be achieved. By doing so only when and where necessary, it is possible to design an efficient set of microarray probes of minimal length.

Latent semantic analysis is a useful collection of techniques for differentiating and classifying genomic sequences by modeling them as unordered sets of distinct, fixed-length words. Dimensionality reduction can be performed using non-negative matrix factorization to identify sets of basis vectors to approximate sequences in high-dimensional LSA-NMF spaces. The basis vectors, due to the non-negativity constraints of non-negative matrix factorization, represent collections of oligonucleotides whose collective presence indicates latent biological features.

By projecting sequences into the high-dimensional feature spaces, the encodings or contributions of each element in the basis set provides a short profile that can be used to identify groups of sequences with similar biological features. By computing the distance or correlation coefficient between pairs of these profiles, a new form of evolutionary distance measure can be used to construct phylogenetic trees, cluster 16S ribosomal genes, and remove unwanted host DNA fragments from a metagenomic sample. The feature vectors themselves can provide a collection of biological keywords, or sets of oligonucleotides whose collective presence is indicative of some biological feature.

Each of the applications described above relies on linear algebra techniques to rotate, scale, or otherwise transform elements in a vector space. The elements are sparse, so the techniques described above can be implemented using simple yet highly efficient methods. Many practical applications can be designed around pre-computed projection matrices to further minimize their level of computational burden.

Latent semantic analysis provides a collection of techniques that can be greatly beneficial in dividing and organizing large amounts of biological information. Latent semantic analysis based techniques provide efficient methods for retrieving and interpreting data in ways that enhance efforts for decoding the genetic language.

LSA-NMF may be used to construct high-dimensional feature spaces capable of distinguishing between relatively short (about 1 kbp) genomic sequences. This approach can be extended to allow for the classification of longer and even whole-genome sequences.

In the examples above, a k-mer size of 7 bp was chosen, resulting in k-mer-sequence profiles of 16,384 elements. When comparing sequences that are several billion bases in length, in order to effectively distinguish between longer sequences, larger k-mer sizes can be used.

LSA-NMF can be used to classify short sequences, it may be possible to use a sliding window approach to sample a whole genome, classify each windowed region, and use a list of the classified elements as a profile to characterize the sequence. For example, consider that certain genes such as the 16S ribosomal sequences are similar across species, a set of feature vectors can be trained to detect such genes. Sequences can be classified not by unordered collections of k-mers but by unordered collections of genes.

Classifying sequences by unordered collection of genes can be applied to the construction of phylogenetic trees. The 16S ribosomal gene alone may not be enough to perfectly reconstruct phylogenies. If other genes that carry phylogenetic signals (such as the recA gene that was used to differentiate between species of *Burkholderia*) can be detected and extracted, samples can be characterized using a combination of several genes in order to construct more accurate phylogenies. Such a system can classify an unknown sample using each gene separately and combine the results to identify the species.

Thus, a series of classifications or clusterings may be used to profile a genomic sequence. When projecting a sample into an LSA-NMF space, due to the non-negativity constraints, a crude form of clustering may be achieved by recording the feature vector (or subset of feature vectors) having the largest contribution in the reconstruction. A series of classifications may be achieved by pre-computing a collection of projection matrices.

LSA-NMF can be applied in a series of projection matrices to partition and search large collections of sequences. For example, given an unknown sample, it is useful to find the most similar item in a large database of known organisms. Using the method described above, a collection of projection matrices can be constructed to classify a sequence at various levels of taxonomic specificity, providing a hashing function into the database.

Figure 18:
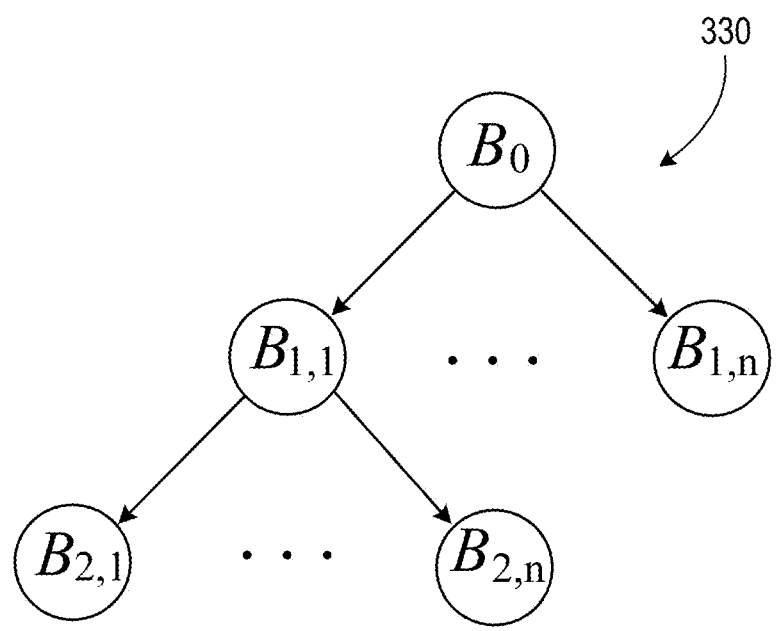
FIG. 18 is a diagram showing projection matrices.

Referring to FIG. 18, a diagram 330 shows how an incoming sample can be profiled using several projection matrices. For example, an incoming sample nucleotide sequence can be converted to a k-mer-sequence profile vector. The profile vector is projected into an initial feature space using a projection matrix $B_0$, which has been designed to differentiate organisms at, e.g., the phylum level. Suppose the sample is identified as belonging to phylum m, and the corresponding projection matrix $B_{1,m}$ breaks this phylum into smaller subgroups, corresponding to one or more classes within the phylum. The profile vector is projected into the feature space using the projection matrix $B_{1,m}$ to determine which subgroup the sample belongs to. This process is repeated for as many steps are necessary to classify the sample, providing a divide and conquer strategy for searching large sequence collections.

Each of the techniques described above can use, e.g., linear algebra methods for factorizing and multiplying matrices. These operations, such as the LSA-NMF based operations, can be implemented efficiently using parallel computing platforms.

Characterization of Protein Sequences Using Latent Semantic Analysis

The following describes the use of latent semantic analysis in the characterization of protein sequences.

A protein sequence can be expressed as a sequence of amino acids. The techniques for analyzing DNA sequences can also be applied to analyzing protein sequences, in which the nucleobases are replaced by amino acids. In this set of analyses, non-negative matrix factorization approach is used as described above. A matrix $\Phi(X)$ having nonnegative entries can be factorized to two matrices having nonnegative entries:

$$\Phi(X)=AY,$$

$$\Phi(X), A, Y \geq 0. \quad \text{(Equ. 18)}$$

In latent semantic analysis terminology, each column of $\Phi(X)$ is decomposed by the dictionary atoms represented by each column of the matrix A and codes represented by each column of the matrix Y.

Here, each column of $\Phi(X)$ is assumed to be a vector representing a protein sequence having an implicit mathematical characterization in a high dimensional metric space. The inner product of any two implicit protein vectors gives the similarity of those two corresponding protein sequences. Therefore, $$S=\Phi(X)^T\Phi(X). \quad \text{(Equ. 19)}$$

Combining Equations 18 and 19 results in the following:

$$S = \Phi(X)^T\Phi(X) \quad \text{(Equ. 20)}$$
$$= \Phi(X)^T AY,$$
$$= A_K Y$$
$$S, A_K, Y \geq 0.$$

The non-negative matrix factorization in Equation 20 results in the identical coding matrix with Equation 18. This provides the property that in order to decompose protein sequences into dictionary codings, it is not necessary to know the implicit characterization, but a similarity matrix is sufficient. The resulting decomposition is referred to as kernel non-negative matrix factorization (KNMF).

To compute the similarity matrix S of a set of protein sequences, the relative complexity measure is used. After kernel non-negative matrix factorization is applied, each protein is represented as a numeric vector that is the dictionary coding provided in the matrix Y. These codes can be used in visualization and classification tasks. The nSpect tool and heatmaps are used for visualizing the data. The classification algorithms that are used include nearest neighbor (1NN), support vector machines (SVM), artificial neural networks (ANN), and random forest (RF) algorithms.

Three categories of protein sequence data are retrieved from the Protein Classification Benchmark collection for machine learning:

1. Classification of 3-phosphoglycerate kinase (3PGK) protein sequences into domains of life (Archaea, Bacteria, Eukaryota) based on phyla: 117 3PGK proteins from 10 phyla are provided from the 3 domains.
2. Functional annotation of unicellular eukaryotic and prokaryotic protein sequences in the COG database: 17973 unicellular eukaryotic and prokaryotic protein sequences from 117 different functional annotation groups are provided.
3. Classification of protein domain sequences and structures into homology (H) groups, based on similarity (S) groups (CATH95 v.3.0.0): 11373 protein sequences from 165 homology groups are provided. All sequences are selected from Protein sequences and structures from CATH (>95% sequence identity) database.

The following describes results of classification of 3-phosphoglycerate kinase (3PGK) protein sequences into domains of life (Archaea, Bacteria, Eukaryota) based on phyla.

The proteins are decomposed into 20-element-codes using kernel non-negative matrix factorization. As one-vs-all classifiers trained to observe the characterization power of the latent semantic analysis representation, perfect separation in 20-D space is obtained (see Table 11 below). The classification accuracy may be worse when the entire similarity matrix is used for classification.

TABLE 11

Classification accuracy of dataset 1 into phyla. The entire data (i.e. similarity matrix) is used to classify using four different algorithms for the column labeled "Entire data." The column labeled "KNMF" represents the classification after latent semantic analysis characterization into 20 dictionary elements.

|  | Entire data | KNMF |
| --- | --- | --- |
| 1NN | 0.86 | 1 |
| SVM | 0.95 | 1 |
| ANN | 0.96 | 1 |
| RF | 0.88 | 1 |

Figure 19:
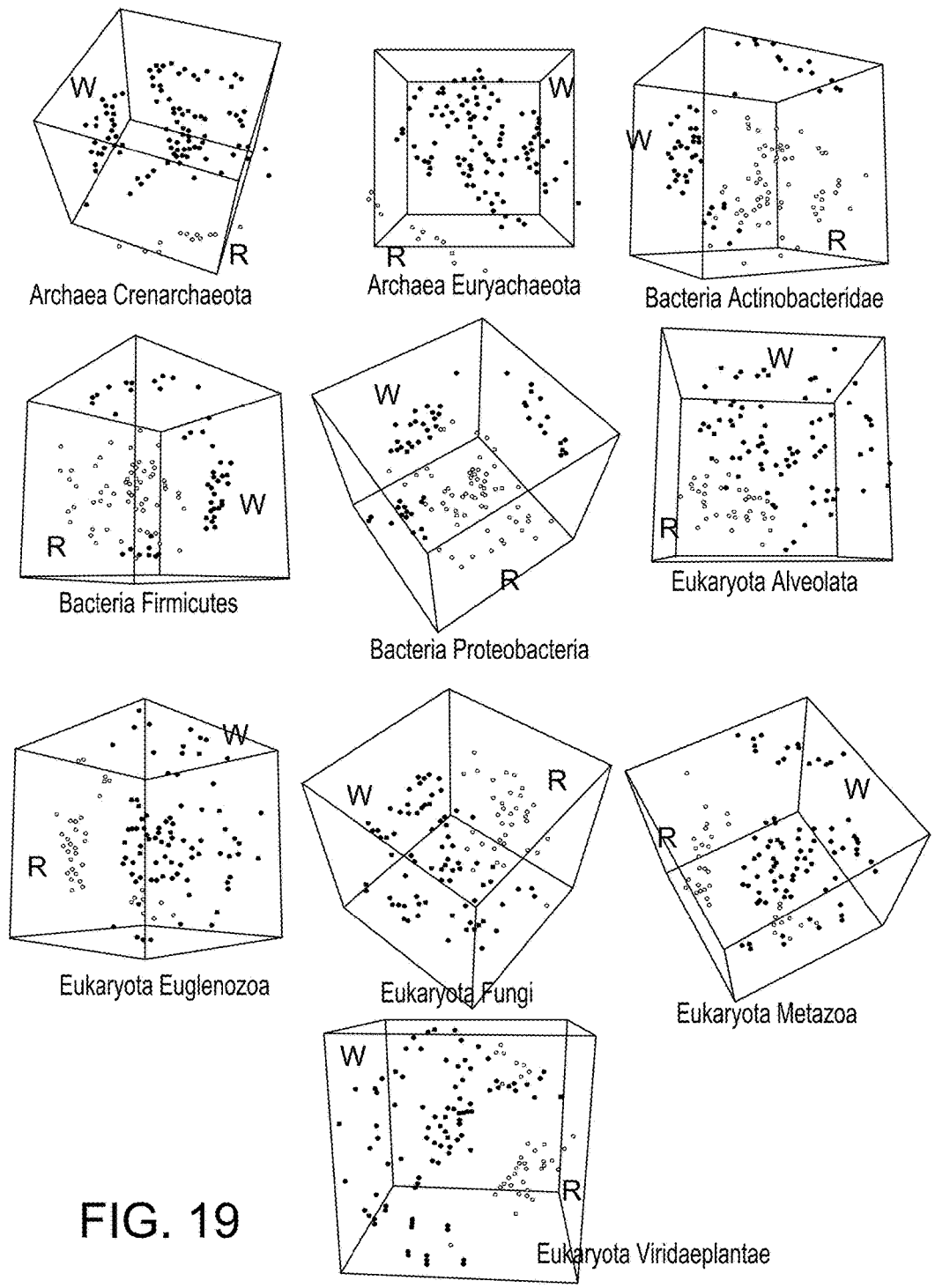
FIGS. 19-21 are graphs.

Referring to FIG. 19, a graph 340 shows 3D projection of latent semantic analysis coded 3PGK proteins. In FIG. 19, the red cubes represent the associated phylum, and the white cubes represent the rest of the data. In the figure, the labels "R" are placed next to the red cubes and the labels "W" are placed next to the white cubes. The graph 340 shows each one of the 10 phyla represented in 3D space using the nSpect tool. The graph 340 indicates that clear separation of 3PGK proteins into taxonomic groups is visible in lower dimensions (e.g., 3 dimensions in this visualization).

The following describes functional annotation of unicellular eukaryotic and prokaryotic protein sequences in the COG database The proteins were latent semantic analysis coded using kernel non-negative matrix factorization into 20 dictionaries. As one-vs-all classifiers trained to observe the characterization power of the latent semantic analysis representation, good separation in 20-D space is obtained (see Table 12).

TABLE 12

Classification accuracy of dataset 2 into functional groups. The entire data (i.e., similarity matrix) is used to classify using 3 different algorithms for the column labeled "Entire data." The column labeled "KNMF" represents the classification after latent semantic analysis characterization into 20 dictionary elements.

|     | Entire data | KNMF |
| --- | --- | --- |
| 1NN | 0.99 | 1 |
| SVM | 1 | 1 |
| RF  | 1 | 1 |

Figure 20A:
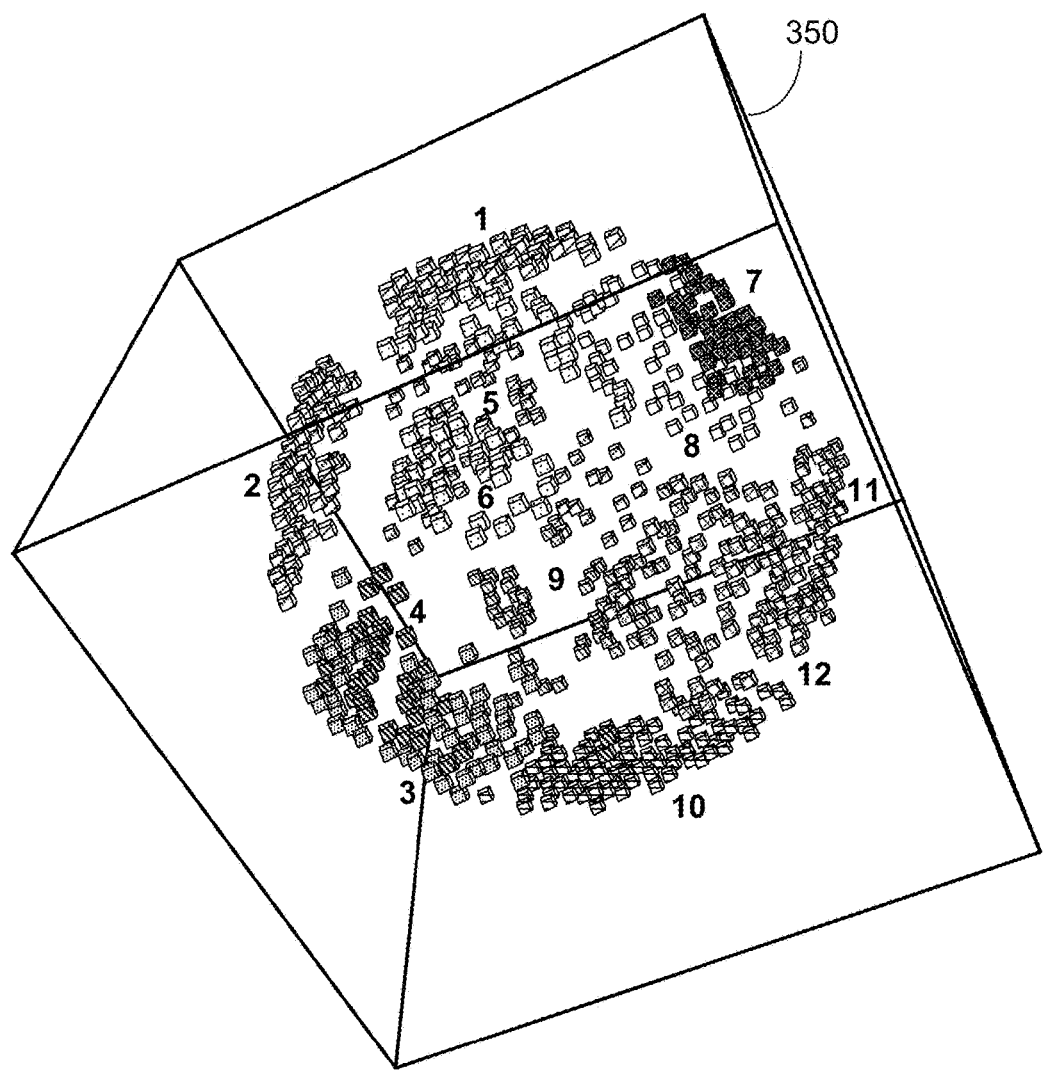
Figure 20B:
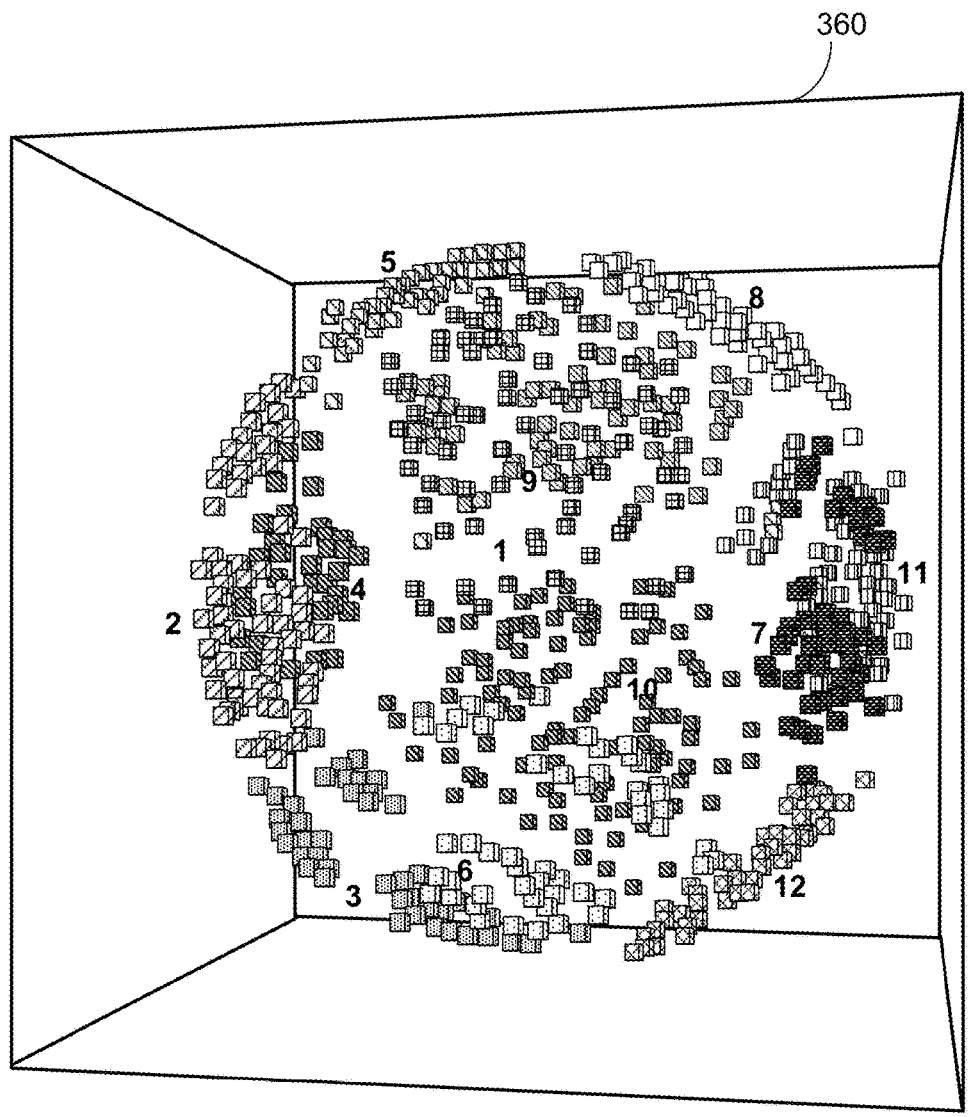
Figure 20C:
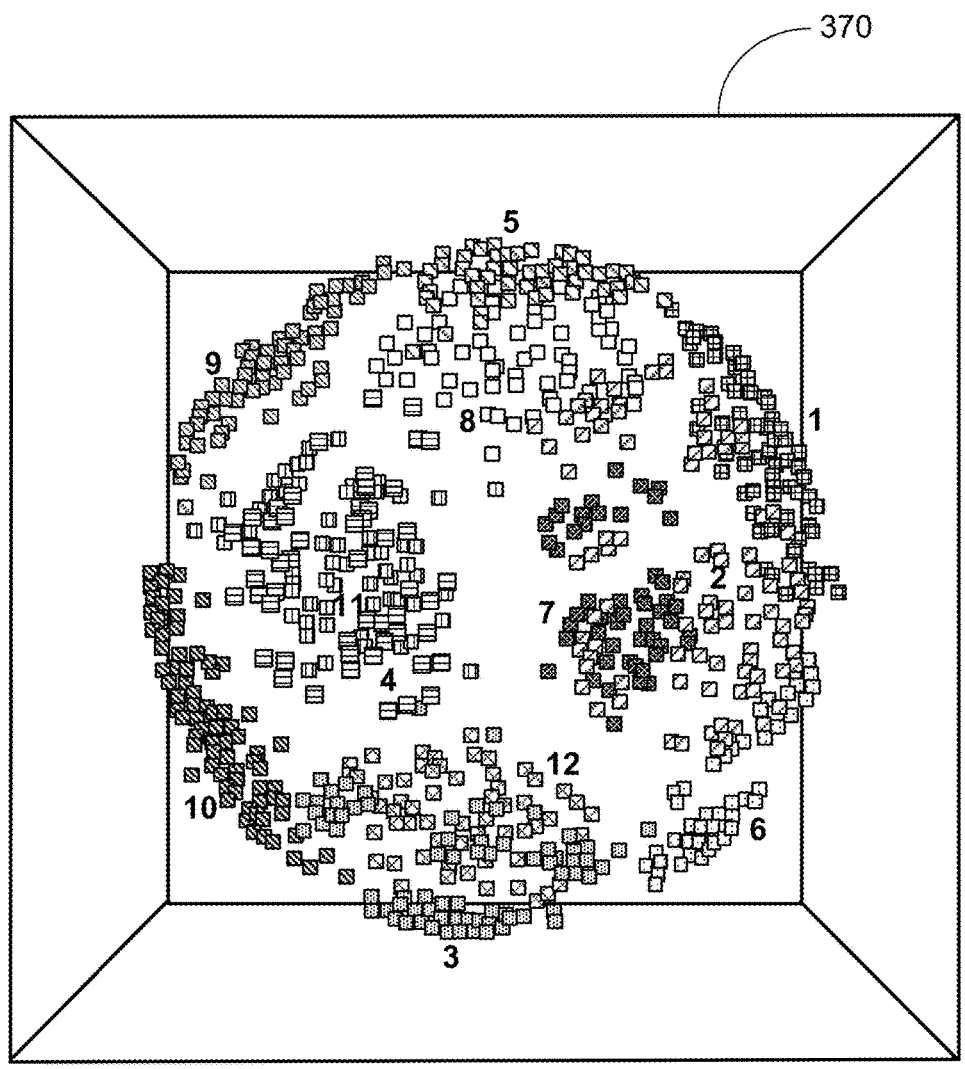

Referring to FIGS. 20A to 20C, graphs 350, 360, and 370 show functional groups represented in 3D space using the nSpect tool, in which various groups are represented with different colors from 3 different camera angles. The clusters formed by latent semantic analysis can be observed in 3 dimensional projections. In FIG. 20A, the graph 350 shows the 3D projection of latent semantic analysis coded proteins from a first camera angle. Each color represents a functional group. There are 12 groups, labeled from 1 to 12 in the figure. FIGS. 20B and 20C show the same information in the 3D space from second and third camera angles.

The following describes classification of protein domain sequences and structures into homology (H) groups, based on similarity (S) groups (CATH95 v.3.0.0)

The proteins were latent semantic analysis coded using kernel non-negative matrix factorization into 40 dictionaries. As one-vs-all classifiers trained to observe the characterization power of the latent semantic analysis representation, good separation in 40-D space is obtained (see Table 13).

TABLE 13

Classification accuracy of dataset 2 into homology groups. The entire data (i.e. similarity matrix) is used to classify using 2 different algorithms for the column labeled "Entire data". The column labeled "KNMF" represents the classification after latent semantic analysis characterization into 40 dictionary elements.

|     | Entire data | KNMF |
| --- | --- | --- |
| 1NN | 0.97 | 1 |
| SVM | 1 | 1 |

Figure 21:
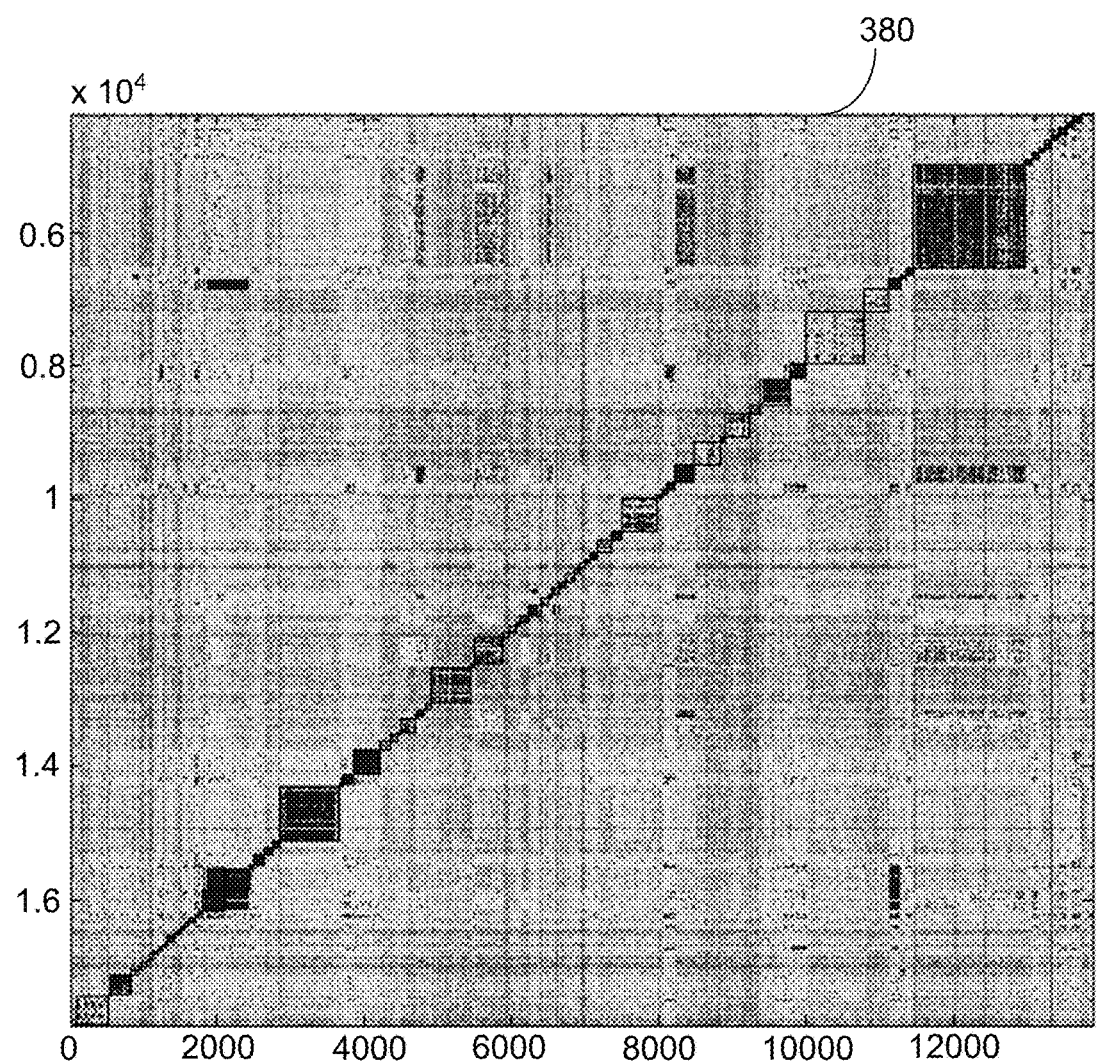

Referring to FIG. 21, a heat map 380 represents the relation of homology groups. Homologous proteins are sorted adjacently and the homology groups are shown in black boundaries along the diagonal. Warm colors represent greater similarity, and cold colors represent greater dissimilarity. The heat map 380 shows latent semantic analysis coded proteins. The heat map 380 allows a user to visualize the characterization ability of latent semantic analysis for homology.

Latent semantic analysis representation of protein sequences derived from relative complexity measurement provides a strong characterization. The examples above based on taxonomic information, functional annotation, and homology groups show that latent semantic analysis codings contain phylogenetic, functional, and homology signals.

Latent semantic analysis of protein sequences can serve several purposes. It provides a concise summary about several properties of a protein that can be employed large scale machine learning tasks. The compact representation provided by latent semantic analysis can label proteins in large databases efficiently. This enables low complexity engine-searches for various features (e.g. homology, functional annotation.)

Figure 22:
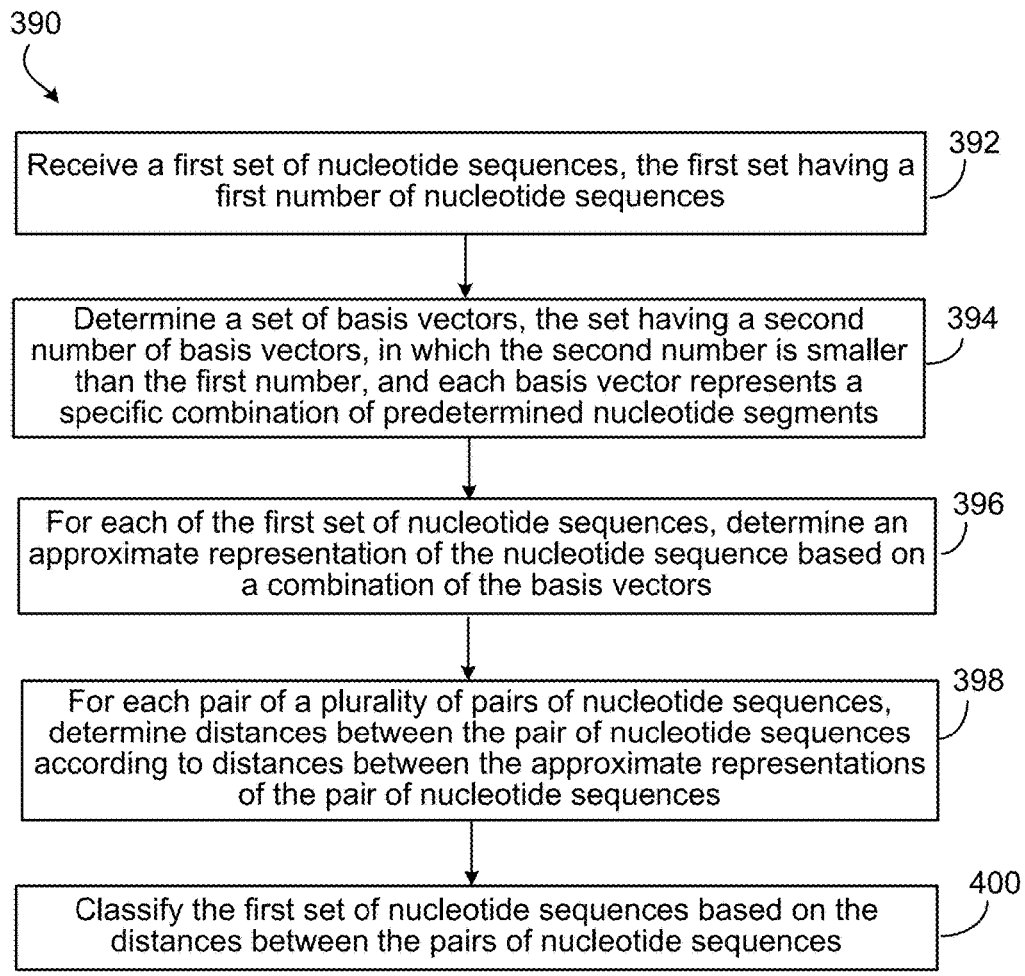
FIGS. 22-24 are flow diagrams of processes.

Referring to FIG. 22, a process 390 for analyzing nucleotide sequences using latent semantic analysis is provided. For example, the process 390 can be implemented by the system 100 of FIG. 1. The process 390 includes receiving a first set of nucleotide sequences, the first set having a first number of nucleotide sequences (392). The process 390 includes determining a set of basis vectors, the set having a second number of basis vectors, in which the second number is smaller than the first number, and each basis vector represents a specific combination of predetermined nucleotide segments (394). The process 390 includes for each of the first set of nucleotide sequences, determining an approximate representation of the nucleotide sequence based on a combination of the basis vectors (396). The process 390 includes for each pair of a plurality of pairs of nucleotide sequences, determining distances between the pair of nucleotide sequences according distances between the approximate representations of the pair of nucleotide sequences (398). The process 390 includes classifying the first set of nucleotide sequences based on the distances between the pairs of nucleotide sequences (400).

Figure 23:
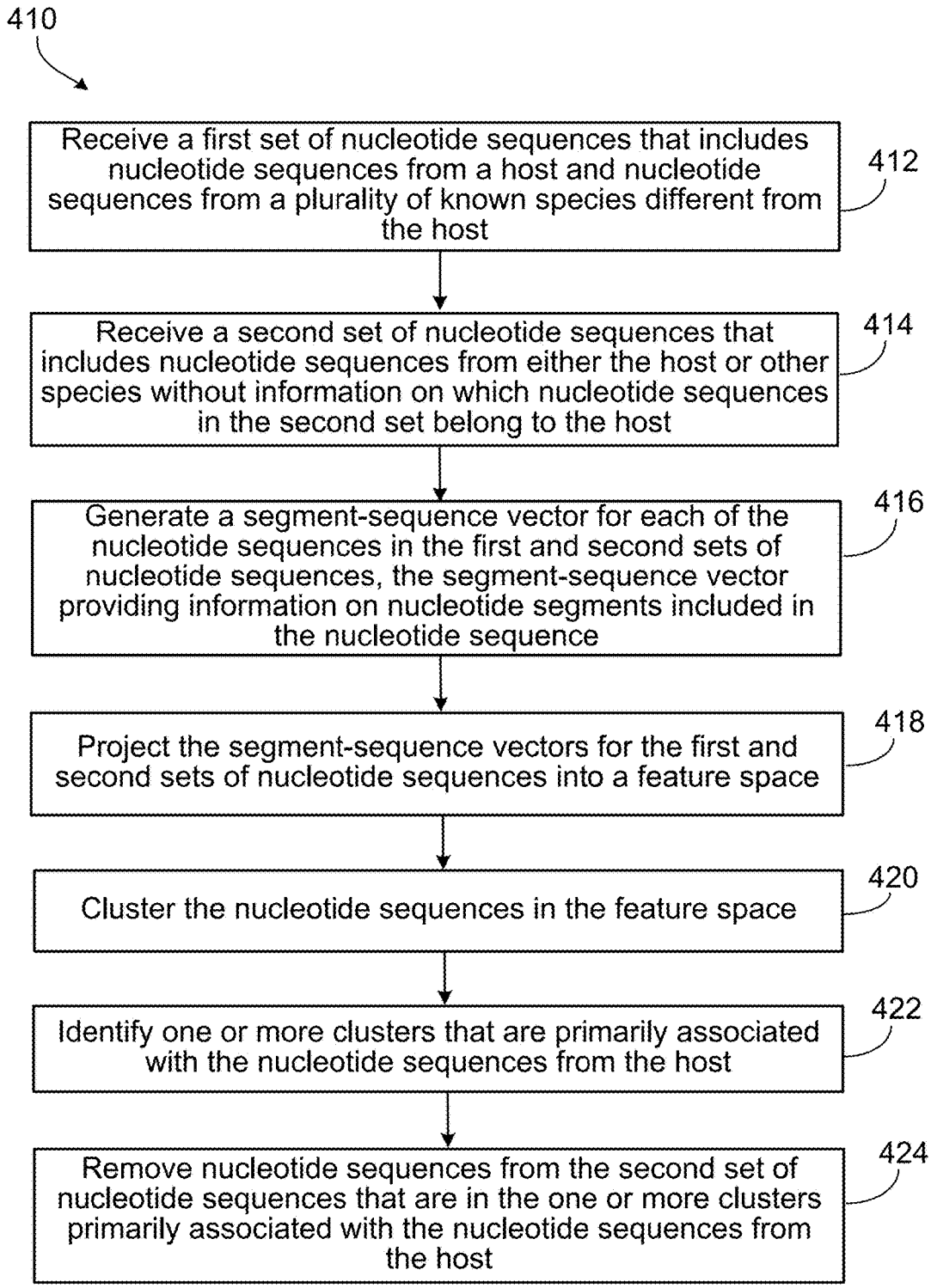

Referring to FIG. 23, a process 410 for analyzing nucleotide sequences taken from an environment using latent semantic analysis is provided. For example, the process 410 can be implemented by the system 120 of FIG. 2. The process 410 includes receiving a first set of nucleotide sequences that includes nucleotide sequences from a host and nucleotide sequences from a plurality of known species different from the host (412). The process 410 includes receiving a second set of nucleotide sequences that includes nucleotide sequences from either the host or other species without information on which nucleotide sequences in the second set belong to the host (414). The process 410 includes generating a segment-sequence vector for each of the nucleotide sequences in the first and second sets of nucleotide sequences, the segment-sequence vector providing information on nucleotide segments included in the nucleotide sequence (416). The process 410 includes projecting the segment-sequence vectors for the first and second sets of nucleotide sequences into a feature space (418); clustering the nucleotide sequences in the feature space (420); identifying one or more clusters that are primarily associated with the nucleotide sequences from the host (422); and removing nucleotide sequences from the second set of nucleotide sequences that are in the one or more clusters primarily associated with the nucleotide sequences from the host (424).

Figure 24:
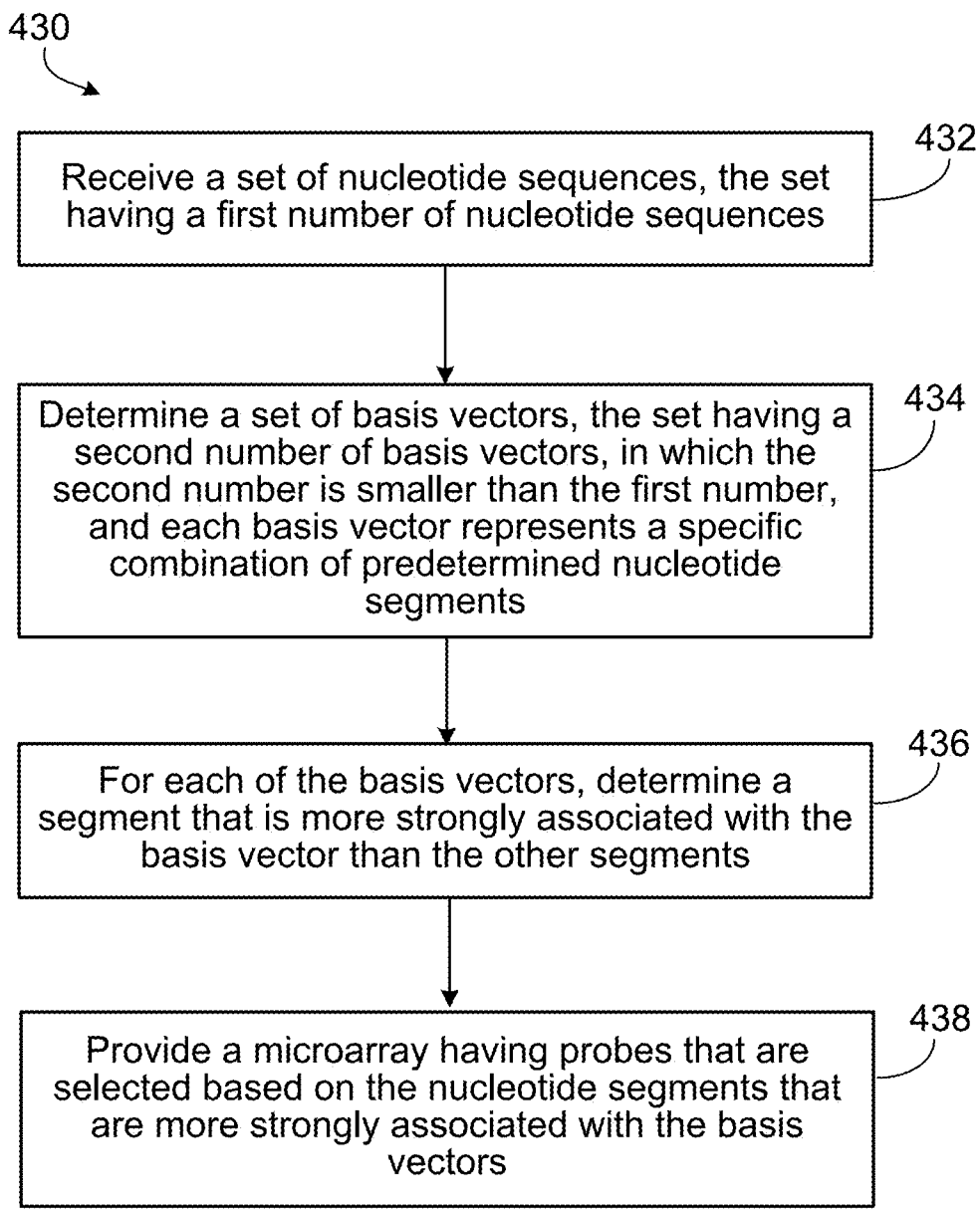

Referring to FIG. 24, a process 430 for designing microarray probes using latent semantic analysis is provided. For example, the process 430 can be implemented by the system 150 of FIG. 3. The process 430 includes receiving a set of nucleotide sequences, the set having a first number of nucleotide sequences (432); determining a set of basis vectors, the set having a second number of basis vectors, in which the second number is smaller than the first number, and each basis vector represents a specific combination of predetermined nucleotide segments (434); and for each of the basis vectors, determining a segment that is more strongly associated with the basis vector than the other segments (436). The process 430 includes providing a microarray having probes that are selected based on the nucleotide segments that are more strongly associated with the basis vectors (438).

The modules in the systems 100, 120, and 150 can be implemented by hardware or a combination of hardware and software. For example, the systems 100, 120, and 150 may include one or more processors and one or more computer-readable mediums (e.g., RAM, ROM, SDRAM, hard disk, optical disk, and flash memory). The one or more processors can execute instructions to implement the functions performed by the modules of systems 100, 120, and 150, such as segment-sequence matrix generation, dimension reduction, clustering, data visualization, feature space and projection matrix generation, clustering and projection, filtering, and feature vector and segment matching. The modules can also be implemented using application-specific integrated circuits (ASICs). The term "computer-readable medium" refers to a medium that participates in providing instructions to a processor for execution, including without limitation, non-volatile media (e.g., optical or magnetic disks), and volatile media (e.g., memory) and transmission media. Transmission media includes, without limitation, coaxial cables, copper wire and fiber optics.

The features described above can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., C, Java), including compiled or interpreted languages, and it can be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

Although some examples have been discussed above, other implementations and applications are also within the scope of the following claims. For example, instead of using k-mers as the words in the genetic language, where k is constant, we can use k-mers as the words in the genetic language, where k is variable. For example, a combination of 7-mers and 8-mers can be used as the words in the genetic language, and the k-mer-sequence matrix M can be replaced with a segment-sequence matrix, in which the segments refer to k-mers, k having two or more values. The systems 100, 120, and 150, and various processes described above can be used to analyzed nucleotide sequences, regardless of whether the sequences include genes or not.

What is claimed is:

1. A method comprising:
   receiving a first set of nucleotide sequences, the first set having a first number of nucleotide sequences, the first set of nucleotide sequences including a first portion and a second portion, the first portion including nucleotide sequences that belong to known species;
   determining, by a data processor, a set of basis vectors, the set having a second number of basis vectors, in which the second number is smaller than the first number, the second number is equal to or larger than two, and each basis vector represents a specific combination of predetermined nucleotide segments;
   for each of the first set of nucleotide sequences, determining an approximate representation of the nucleotide sequence based on a combination of the basis vectors;
   for each pair of a plurality of pairs of nucleotide sequences, determining distances between the pair of nucleotide sequences according to distances between the approximate representations of the pair of nucleotide sequences;
   classifying the first set of nucleotide sequences based on the distances between the pairs of nucleotide sequences;

for each nucleotide sequence in the second portion, determining whether the nucleotide sequence is associated with one of the known species based on the classification of the first set of nucleotide sequences; and generating, by the data processor, an output having information about, for each of those nucleotide sequences in the second portion that are associated with known species, which one of the known species is associated with the nucleotide sequence.

2. The method of claim 1 in which the first portion of the first set of nucleotide sequences belong to known species of at least one of prokaryotes, eukaryotes, or viruses, the second portion of the first set of nucleotide sequences are obtained from a patient, and the method comprises, for each nucleotide sequence in the second portion, determining whether the nucleotide sequence is associated with one of the known species of the at least one of prokaryotes, eukaryotes, or viruses based on the classification of the first set of nucleotide sequences.

3. The method of claim 2, comprising generating an output having information that indicates, for each nucleotide sequence in the second portion, which one of the known species of the at least one of prokaryotes, eukaryotes, or viruses, if any, is associated with the nucleotide sequence.

4. The method of claim 1 in which the predetermined nucleotide segments are k-mers each having k nucleobases, k being a positive integer, and each basis vector represents a specific combination of the k-mers.

5. The method of claim 4 in which determining a set of basis vectors comprises forming a k-mer-sequence matrix in which rows of the matrix represent the k-mers and columns of the matrix represent the nucleotide sequences, k being a positive integer, and each element in the matrix represents a repetition frequency of the segment represented by the corresponding row within the sequence represented by the corresponding column, and applying a dimension reduction process to the k-mer-sequence matrix to determine the basis vectors.

6. The method of claim 5 in which applying a dimension reduction process comprises applying at least one of non-negative matrix factorization or singular value decomposition to the segment-sequence matrix to determine the basis vectors.

7. The method of claim 1 in which determining a set of basis vectors comprises forming a segment-sequence matrix in which rows of the matrix represent the nucleotide segments and columns of the matrix represent the sequences, each element in the matrix representing a repetition frequency of the segment represented by the corresponding row within the sequence represented by the corresponding column, and applying a dimension reduction process to the segment-sequence matrix to determine the basis vectors.

8. The method of claim 7 in which applying a dimension reduction process comprises applying at least one of non-negative matrix factorization or singular value decomposition to the segment-sequence matrix to determine the basis vectors.

9. The method of claim 1 in which determining an approximate representation of the nucleotide sequence based on a combination of the basis vectors comprises determining an approximate representation of the nucleotide sequence based on a linear combination of the basis vectors.

10. The method of claim 1 in which determining an approximate representation of the nucleotide sequence comprises determining coefficients for a linear combination of the basis vectors that represents an approximation of the nucleotide sequence.

11. The method of claim 1 in which the distance between the approximate representations of the pair of nucleotide sequences is determined according to at least one of (i) Euclidean distance between the approximate representations of the pair of nucleotide sequences or (ii) correlation between the approximate representations of the pair of nucleotide sequences.

12. The method of claim 1, comprising determining the distance between every pair of nucleotide sequences, and classifying the first set of nucleotide sequences based on the distances between all of the pairs of nucleotide sequences.

13. The method of claim 1 in which species of the second portion of the first set of nucleotide sequences are initially unknown.

14. The method of claim 1, comprising generating a phylogenetic tree for the first set of nucleotide sequences based on the classification of the first set of nucleotide sequences.

15. The method of claim 1, comprising determining whether one or more of the first set of nucleotide sequences are associated with pathogenic species based on the classification of the first set of nucleotide sequences, and generating an output having information about which one or more of the first set of nucleotide sequences are associated with pathogenic species.

16. The method of claim 1, comprising determining which nucleotide sequences are associated with low risk species, and which nucleotide sequences are associated with high risk species, based on the classification of the first set of nucleotide sequences, and generating an output indicating which nucleotide sequences are associated with low risk species, and which nucleotide sequences are associated with high risk species.

17. The method of claim 1, comprising receiving a second set of nucleotide sequences that includes nucleotide sequences from a host and nucleotide sequences from a plurality of known species different from the host, classifying the second set of nucleotide sequences based on the distances between the pairs of nucleotide sequences, and identifying nucleotide sequences that are primarily associated with the host based on the classification of the first and second sets of nucleotide sequences.

18. The method of claim 17, comprising removing, from the second set of nucleotide sequences, nucleotide sequences that are primarily associated with the host.

19. The method of claim 18, comprising generating an output having information about the nucleotide sequences remaining in the second set of nucleotide sequences after the nucleotide sequences primarily associated with the host have been removed.

20. The method of claim 17 in which the second set of nucleotide sequences comprises a second set of 16S ribosomal RNA sequences.

21. The method of claim 1, comprising obtaining a sample from an animal or a human, and generating the first set of nucleotide sequences from the sample.

22. The method of claim 21, comprising obtaining the sample from a gut of the animal or the human.

23. The method of claim 22, comprising determining bacteria species in the sample obtained from the gut of the animal or the human based on the classification of the first set of nucleotide sequences.

24. The method of claim 23, comprising generating an output having information about the bacteria species in the sample obtained from the gut of the animal or the human.

25. The method of claim 1, comprising determining a projection matrix based on the basis vectors, and projecting segment-sequence vectors into a feature space based on the projection matrix.

26. The method of claim 25, comprising:
receiving a second set of nucleotide sequences that includes nucleotide sequences from a host and nucleotide sequences from a plurality of species different from the host;
projecting the second set of nucleotide sequences into the feature space;
clustering the projected sequences in the feature space; and
identifying one or more clusters that are primarily associated with the host.

27. The method of claim 25, comprising
receiving a second set of nucleotide sequences that includes nucleotide sequences from a host and nucleotide sequences from a plurality of known species different from the host;
receiving a third set of nucleotide sequences that includes nucleotide sequences from either the host or other species without information on which nucleotide sequences in the third set belong to the host;
projecting the second and third sets of nucleotide sequences into the feature space;
clustering the projected sequences in the feature space;
identifying one or more clusters that are primarily associated with the host; and
removing sequences from the third set that are in the one or more clusters primarily associated with the host.

28. The method of claim 27 in which the plurality of known species comprises known species of at least one of prokaryotes, eukaryotes, or viruses, and the third set of nucleotide sequences are obtained from the host.

29. The method of claim 1 in which determining an approximate representation of the nucleotide sequence based on a combination of the basis vectors comprises determining an approximate representation of the nucleotide sequence based on a linear combination of the basis vectors.

30. The method of claim 1 in which the predetermined nucleotide segments are kmers each having k nucleobases, k being a positive integer, and each basis vector represents a specific combination of the k-mers.

31. The method of claim 1 in which the first set of nucleotide sequences comprises a first set of 16S ribosomal RNA sequences.

32. An apparatus comprising:
a memory to store data representing a first set of nucleotide sequences, the first set having a first number of nucleotide sequences, the first set of nucleotide sequences including a first portion and a second portion, the first portion including nucleotide sequences that belong to known species; and
a data processor configured to process the data and
determine a set of basis vectors, the set having a second number of basis vectors, in which the second number is smaller than the first number, the second number is equal to or larger than two, and each basis vector represents a specific combination of predetermined nucleotide segments;
for each of the first set of nucleotide sequences, determine an approximate representation of the nucleotide sequence based on a combination of the basis vectors;
for each pair of a plurality of pairs of nucleotide sequences, determine a distance between the pair of nucleotide sequences according to a distance between the approximate representations of the pair of nucleotide sequences;
classify the first set of nucleotide sequences based on the distances between the pairs of nucleotide sequences;
for each nucleotide sequence in the second portion, determine whether the nucleotide sequence is associated with one of the known species based on the classification of the first set of nucleotide sequences; and
generate, by the data processor, an output having information about, for each of those nucleotide sequences in the second portion that are associated with known species, which one of the known species is associated with the nucleotide sequence.

33. The apparatus of claim 32 in which the first portion of the first set of nucleotide sequences belong to known species of at least one of prokaryotes, eukaryotes, or viruses, the second portion of the first set of nucleotide sequences are obtained from a patient, and
the data processor is further configured to, for each nucleotide sequence in the second portion, determine whether the nucleotide sequence is associated with one of the known species of the at least one of prokaryotes, eukaryotes, or viruses based on the classification of the first set of nucleotide sequences.

34. The apparatus of claim 33 in which the data processor is configured to generate an output having information that indicates, for each nucleotide sequence in the second portion, which one of the known species of the at least one of prokaryotes, eukaryotes, or viruses, if any, is associated with the nucleotide sequence.

35. The apparatus of claim 32 in which the predetermined nucleotide segments are kmers each having k nucleobases, k being a positive integer, and each basis vector represents a specific combination of the k-mers.

36. The apparatus of claim 35 in which determine a set of basis vectors comprises
form a k-mer-sequence matrix in which rows of the matrix represent the k-mers and columns of the matrix represent the nucleotide sequences, k being a positive integer, and each element in the matrix represents a repetition frequency of the segment represented by the corresponding row within the sequence represented by the corresponding column, and
apply at least one of non-negative matrix factorization or singular value decomposition to the k-mer-sequence matrix to determine the basis vectors.

37. The apparatus of claim 32 in which determine a set of basis vectors comprises
form a segment-sequence matrix in which rows of the matrix represent the nucleotide segments and columns of the matrix represent the sequences, each element in the matrix representing a repetition frequency of the segment represented by the corresponding row within the sequence represented by the corresponding column, and
apply at least one of non-negative matrix factorization or singular value decomposition to the segment-sequence matrix to determine the basis vectors.

38. The apparatus of claim 32 in which determine an approximate representation of the nucleotide sequence based on a combination of the basis vectors comprises determine an approximate representation of the nucleotide sequence based on a linear combination of the basis vectors.

39. The apparatus of claim 32 in which determine an approximate representation of the nucleotide sequence comprises determine coefficients for a linear combination of the basis vectors that represents an approximation of the nucleotide sequence.

40. The apparatus of claim 32 in which the distance between the approximate representations of the pair of nucleotide sequences is determined according to at least one of (i) Euclidean distance between the approximate representations of the pair of nucleotide sequences or (ii) correlation between the approximate representations of the pair of nucleotide sequences.

41. The apparatus of claim 32 in which the data processor is further configured to determine the distance between every pair of nucleotide sequences, and classify the first set of nucleotide sequences based on the distances between all of the pairs of nucleotide sequences.

42. The apparatus of claim 32 in which species of the second portion of the first set of nucleotide sequences are initially unknown.

43. The apparatus of claim 32, comprising a graphical user interface to provide a graphical presentation of classification of the first set of nucleotide sequences.

44. The apparatus of claim 32 in which generating the output comprises generating a phylogenetic tree for the first set of nucleotide sequences based on the classification of the first set of nucleotide sequences.

45. The apparatus of claim 32, comprising determining whether one or more of the first set of nucleotide sequences are associated with pathogenic species based on the classification of the first set of nucleotide sequences, and generating an output having information about which one or more of the first set of nucleotide sequences are associated with pathogenic species.

46. The apparatus of claim 32, comprising determining which nucleotide sequences are associated with low risk species, and which nucleotide sequences are associated with high risk species, based on the classification of the first set of nucleotide sequences, and generating an output indicating which nucleotide sequences are associated with low risk species, and which nucleotide sequences are associated with high risk species.

47. The apparatus of claim 32 in which the data processor is configured to receive a second set of nucleotide sequences that includes nucleotide sequences from a host and nucleotide sequences from a plurality of known species different from the host, classify the second set of nucleotide sequences based on the distances between the pairs of nucleotide sequences, and identify nucleotide sequences that are primarily associated with the host based on the classification of the first and second sets of nucleotide sequences.

48. The apparatus of claim 47 in which the data processor is configured to remove, from the second set of nucleotide sequences, nucleotide sequences that are primarily associated with the host.

49. The apparatus of claim 48 in which the data processor is configured to generate an output having information about the nucleotide sequences remaining in the second set of nucleotide sequences after the nucleotide sequences primarily associated with the host have been removed.

50. The apparatus of claim 47 in which the second set of nucleotide sequences comprises a second set of 16S ribosomal RNA sequences.

51. The apparatus of claim 32 in which the first set of nucleotide sequences is generated from a sample obtained from an animal or a human.

52. The apparatus of claim 51 in which the sample is obtained from a gut of the animal or the human.

53. The apparatus of claim 52 in which the data processor is configured to determine bacteria species in the sample obtained from the gut of the animal or the human based on the classification of the first set of nucleotide sequences.

54. The apparatus of claim 53 in which the data processor is configured to generate an output having information about the bacteria species in the sample obtained from the gut of the animal or the human.

55. The apparatus of claim 32 in which the data processor is configured to determine a projection matrix based on the basis vectors, and project segment-sequence vectors into a feature space based on the projection matrix.

56. The apparatus of claim 55 in which the memory stores data representing a second set of nucleotide sequences that includes nucleotide sequences from a host and nucleotide sequences from a plurality of species different from the host, and the data processor is configured to:
project the second set of nucleotide sequences into the feature space;
cluster the projected sequences in the feature space; and
identify one or more clusters that are primarily associated with the host.

57. The apparatus of claim 55 in which the memory stores data representing a second set of nucleotide sequences that includes nucleotide sequences from a host and nucleotide sequences from a plurality of known species different from the host;
the memory also stores data representing a third set of nucleotide sequences that includes nucleotide sequences from either the host or other species without information on which nucleotide sequences in the third set belong to the host;
wherein the data processor is configured to:
project the second and third sets of nucleotide sequences into the feature space;
cluster the projected sequences in the feature space;
identify one or more clusters that are primarily associated with the host; and
remove sequences from the third set that are in the one or more clusters primarily associated with the host.

58. The apparatus of claim 57 in which the plurality of known species comprises known species of at least one of prokaryotes, eukaryotes, or viruses, and the third set of nucleotide sequences are obtained from the host.

59. The apparatus of claim 32 in which determining an approximate representation of the nucleotide sequence based on a combination of the basis vectors comprises determining an approximate representation of the nucleotide sequence based on a linear combination of the basis vectors.

60. The apparatus of claim 32 in which the predetermined nucleotide segments are kmers each having k nucleobases, k being a positive integer, and each basis vector represents a specific combination of the k-mers.

61. The apparatus of claim 32 in which the first set of nucleotide sequences comprises a first set of 16S ribosomal RNA sequences.

* * * * *

UNITED STATES PATENT AND TRADEMARK OFFICE
CERTIFICATE OF CORRECTION

PATENT NO. : 9,659,145 B2
APPLICATION NO. : 13/954925
DATED : May 23, 2017
INVENTOR(S) : Khalid Sayood et al.

It is certified that error appears in the above-identified patent and that said Letters Patent is hereby corrected as shown below:

In the Specification

In Column 2, Line 11, please delete "semi-normegative" and insert -- Semi-nonnegative --, therefor.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*